United States Patent
Samuelsson et al.

(10) Patent No.: US 11,680,082 B2
(45) Date of Patent: Jun. 20, 2023

(54) CONJUGATES OF MONTELUKAST AND PEPTIDES

(71) Applicant: ENLITISA (SHANGHAI) PHARMACEUTICAL CO., LTD, Shanghai (CN)

(72) Inventors: Bengt Ingemar Samuelsson, Stockholm (SE); Ming Gu, Tiangyin (CN)

(73) Assignee: ENLITISA (SHANGHAI) PHARMACEUTICAL CO., LTD., Shanghai (CN)

( * ) Notice: Subject to any disclaimer, the term of this patent is extended or adjusted under 35 U.S.C. 154(b) by 0 days.

(21) Appl. No.: 16/645,355

(22) PCT Filed: Sep. 14, 2019

(86) PCT No.: PCT/CN2019/105832
§ 371 (c)(1),
(2) Date: Mar. 6, 2020

(87) PCT Pub. No.: WO2020/052677
PCT Pub. Date: Mar. 19, 2020

(65) Prior Publication Data
US 2021/0309696 A1    Oct. 7, 2021

(30) Foreign Application Priority Data

Sep. 14, 2018 (WO) ................ PCT/CN2018/105703
Dec. 4, 2018 (WO) ................ PCT/CN2018/119072

(51) Int. Cl.
*A61K 47/64* (2017.01)
*A61P 17/00* (2006.01)
(Continued)

(52) U.S. Cl.
CPC .............. *C07K 7/06* (2013.01); *A61K 9/1676* (2013.01); *A61K 31/47* (2013.01); *A61P 29/00* (2018.01); *A61K 38/00* (2013.01)

(58) Field of Classification Search
CPC combination set(s) only.
See application file for complete search history.

(56) References Cited

U.S. PATENT DOCUMENTS

| 2005/0002934 A1* | 1/2005 | Reed .............. A61P 11/00 424/145.1 |
| 2005/0107612 A1 | 5/2005 | Reguri et al. |

(Continued)

FOREIGN PATENT DOCUMENTS

| CN | 102068432 A | 5/2011 |
| WO | 2002/034237 A1 | 5/2002 |

(Continued)

OTHER PUBLICATIONS

UniProtKB accession No. Q27409, an adhesive plaque matrix protein from Mytilus galloprovincialis accessed Apr. 9, 2022 at URL uniprot.org/uniprot/Q27409 (Year: 2022).*
(Continued)

*Primary Examiner* — Julie Ha
*Assistant Examiner* — Kristina M Hellman
(74) *Attorney, Agent, or Firm* — Troutman Pepper Hamilton Sanders LLP (Rochester)

(57) ABSTRACT

There is provided a peptide-containing compound that comprises a peptide component which is an amino acid sequence of from 2 to 45 (e.g. from 6 to 15) amino acids, which peptide component is covalently bonded to one or more compounds of formula I:

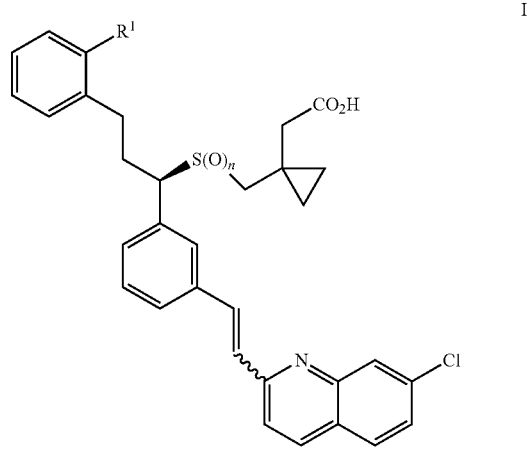

wherein:
$R^1$ is selected from the group consisting of —C(CH$_3$)$_2$OH, —COCH$_3$, —C(CH$_3$)=CH$_2$ and —C(CH$_3$)$_2$H; and
n is 0, 1 or 2, as well as regioisomers, stereoisomers, and pharmaceutically- or cosmetically-acceptable salts of said peptide-containing compound. The compound of formula I is preferably montelukast, montelukast styrene or hydrogenated montelukast styrene. The peptide-containing compound is particularly useful in the treatment of conditions characterised by inflammation, including wounds, hemorrhoids, burns, psoriasis, acne, atopic dermatitis, allergic rhinitis, allergic conjunctivitis, chronic obstructive pulmonary disease, inflammatory bowel disease (such as ulcerative colitis). Compounds of the invention are also useful in the treatment of idiopathic pulmonary fibrosis.

40 Claims, 9 Drawing Sheets
Specification includes a Sequence Listing.

(51) Int. Cl.
    A61P 29/00      (2006.01)
    C07K 2/00       (2006.01)
    C07K 7/06       (2006.01)
    A61K 9/16       (2006.01)
    A61K 31/47      (2006.01)
    A61K 38/00      (2006.01)

(56) References Cited

U.S. PATENT DOCUMENTS

2009/0186038 A1* 7/2009 Reed .................. A61K 31/381
                                                    424/158.1
2018/0228873 A1   8/2018 Samuelsson et al.

FOREIGN PATENT DOCUMENTS

| WO | 2002/067917 A1 | 9/2002 |
| WO | 2002/069930 A1 | 9/2002 |
| WO | 2003/020200 A2 | 3/2003 |
| WO | 2004/005309 A2 | 1/2004 |
| WO | 2005/046575 A2 | 5/2005 |
| WO | 2006/046123 A2 | 5/2006 |
| WO | 2007/089745 A2 | 8/2007 |
| WO | 2012/112690 A2 | 8/2012 |
| WO | 2013/170655 A1 | 11/2013 |
| WO | 2017/011982 A1 | 1/2017 |
| WO | 2018/213928 A1 | 11/2018 |
| WO | 2019/007355 A1 | 1/2019 |
| WO | 2019/007356 A1 | 1/2019 |

OTHER PUBLICATIONS

UniProtKB accession No. A0A4Y8QDT9, Potra domain-containing protein from Shinella sumterensis accessed Apr. 9, 2022 at URL uniprot.org/uniprot/A0A4Y8QDT9 (Year: 2022).*

UniProtKB accession No. A0A177E2R0, an uncharacterized protein from Alternaria alternata accessed Apr. 9, 2022 at URL uniprot.org/uniprot/A0A177E2R0 (Year: 2022).*

UniProtKB accession No. Q25460, an adhesive plaque matrix protein from Mytilus edulis accessed Apr. 9, 2022 at URL uniprot.org/uniprot/Q25460 (Year: 2022).*

Beller et al., "Cysteinyl Leukotriene 1 Receptor Controls the Severity of Chronic Pulmonary Inflammation and Fibrosis," PNAS 101(9):3047-3052 (2004).

Dalsin et al., "Mussel Adhesive Protein Mimetic Polymers for the Preparation of Nonfouling Surfaces," J Am. Chem. Soc. 125:4253-4258 (2003).

Gao et al., "Review on Mussel Adhesive Protein," Journal of Anhui Agr. Sci. 39(32):19860-19862 (2011).

Hon et al., "Clinical Effectiveness and Safety of Montelukast in Ashma. What are the Conclusions from Clinical Trials and Meta-Analyses?," Drug Design, Development and Therapy 8:839-850 (2014).

Sener et al., "Leukotriene Receptor Blocker Montelukast Protects Against Burn-Induced Oxidative Injury of the Skin and Remote Organs," Burns 31:587-596 (2005).

Waite J. H., "Nature's Underwater Adhesive Specialist," Int. J. Adhesion and Adhesives 7(1)9-14 (1987).

Yamamoto et al., "Synthesis and Adhesive Studies of Marine Polypeptides," J Chem. Soc., Perkin Trans. 1:613-618 (1987).

Zhu et al., "Composition, Working Mechanism and Application of Mussel Adhesive Protein," Advances in Marine Science 32(4):560-570 (2014) (English Translation).

International Search Report and Written Opinion for Application No. PCT/CN2018/105703 (dated Jun. 6, 2019).

Ahn et al., "Mussel Adhesive Protein-conjugated Vitronectin (fp-151-VT) Induces Anti-inflammatory Activity on LPS-stimulated Macrophages and UVB-irradiated Keratinocytes," Immunological Investigations 48(3):242-254(2018).

Yang et al., "Mussel Adhesive Protein Fused with VE-cadherin Domain Specifically Triggers Endothelial Cell Adhesion," Journal of Materials Chemistry 6(24):4151-4163 (2018).

* cited by examiner

CONJUGATES OF MONTELUKAST AND PEPTIDES

This application is a national stage application under 35 U.S.C. § 371 of PCT Application No. PCT/CN2019/105832, filed Sep. 14, 2019, which claims the priority benefit of PCT Application No. PCT/CN2018/119072, filed Dec. 4, 2018, and PCT Application No. PCT/CN2018/105703, filed Sep. 14, 2018.

FIELD OF THE INVENTION

This invention relates to new conjugates of a known anti-inflammatory compound covalently linked to specific peptide sequences, the use of such new conjugates in human medicine, and to pharmaceutical compositions comprising them. In particular, the invention relates to the use of those conjugates and compositions in the treatment of inflammation.

BACKGROUND AND PRIOR ART

Inflammation is typically characterised as a localised tissue response to e.g. invasion of microorganisms, certain antigens, damaged cells or physical and/or chemical factors. The inflammatory response is normally a protective mechanism which serves to destroy, dilute or sequester both the injurious agent and the injured tissue, as well as to initiate tissue healing.

Inflammation may result from physical trauma, infection, some chronic diseases (e.g. psoriasis and autoimmune diseases, such as rheumatoid arthritis) and/or chemical and/or physiological reactions to external stimuli (e.g. as part of an allergic response). A complex series of events may be involved, in which inflammatory mediators increase blood flow and dilation of local blood vessels, resulting in redness and heat, the exudation of fluids, often resulting in localised swelling, leukocytic migration into the inflamed area, and pain.

Many conditions/disorders are characterized by, and/or are caused by, abnormal, tissue-damaging inflammation. Such conditions are typically characterized by activation of immune defence mechanisms, resulting in an effect that is more harmful than beneficial to the host, and are generally associated with varying degrees of tissue redness or hyperemia, swelling, hyperthermia, pain, itching, cell death, tissue destruction, cell proliferation and/or loss of function. Examples include inflammatory bowel diseases, rheumatoid arthritis, multiple sclerosis, psoriasis, glomerulonephritis and transplant rejection.

Typically, a complex series of events results in inflammatory changes such as increased blood flow through dilation of local blood vessels, resulting in redness and heat, the extravasation of leukocytes and plasma, often resulting in localised swelling, activation of sensory nerves (resulting in pain in some tissues) and loss of function. These inflammatory changes are triggered by a cascade of cellular and biochemical events involving cells like neutrophils, monocytes, macrophages and lymphocytes together with inflammatory mediators such as vasoactive amines, cytokines, complement factors and reactive oxygen species.

Amongst other things, inflammation plays a key role in the wound healing process. Wounds and burns can therefore be classified as conditions with which inflammation is associated. Traditional thinking in the art is that antiinflammatory drugs should not be applied directly to open wounds, as this would be detrimental to the progress of wound healing.

Montelukast is an orally-active non-steroidal immunomodulating compound that is administered perorally to the gastrointestinal tract for the maintenance treatment and prevention of symptoms of seasonal allergies (see e.g. Hon et al, *Drug Design, Development and Therapy*, 8, 839 (2014)). It acts by blocking the action of, primarily, leukotriene D4 (as well as leukotrienes C4 and E4) on the cysteinal leukotriene receptor CysLT1 in the airways.

International patent applications WO 02/34237 and WO 2003/020200 disclose active agents covalently attached to polypeptides, more specifically homo- and heteropolymers of naturally occurring and/or synthetic amino acids.

We have previously found, unexpectedly, that montelukast displays an antiinflammatory effect when administered locally, e.g. topically, for example to the skin (see unpublished international patent application PCT/CN2018/094441). We have now found that montelukast coupled covalently to certain amino acid sequences gives rise to new compounds that are of potential use in the various conditions including the topical treatment of skin conditions such as inflammation and wounds.

DISCLOSURE OF THE INVENTION

According to a first aspect of the invention, there is provided a peptide-containing compound that comprises a peptide component which is an amino acid sequence of from 2 to 45 amino acids, which peptide component is covalently bonded to one or more compounds of the formula I:

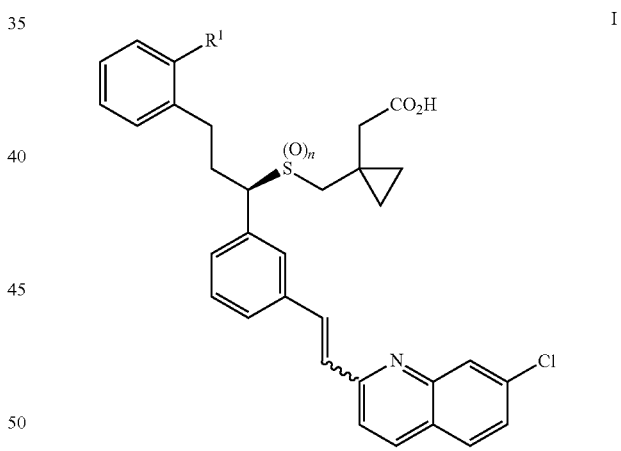

wherein:
$R^1$ is selected from the group consisting of —C(CH$_3$)$_2$OH, —COCH$_3$, —C(CH$_3$)=CH$_2$ and —C(CH$_3$)$_2$H; and
n is 0, 1 or 2,
as well as regioisomers, stereoisomers, and pharmaceutically- or cosmetically-acceptable salts of said peptide-containing compound,
which peptide-containing compounds, regioisomers, stereoisomers and salts are referred to together hereinafter as "the compounds of the invention".

Compounds of the invention contain at least one primary amide linkage through which the one or more compounds of formula I is/are coupled to the peptide component. The amide linkage is formed by way of reaction of the carboxylic acid group(s) in the one or more compounds of formula I with one or more free —NH$_2$ groups in the peptide component. The amide linkage may be formed at the N-terminal —NH$_2$ group and/or through one or more other free —NH$_2$ groups in the amino acids that are present in the peptide sequence.

It is accordingly preferred that at least one of the amino acids in the peptide component in a compound of the invention comprises a positively charged group (i.e. a free —NH$_2$ group) that is not the N-terminal. The amino acids in the peptide component of compounds of the invention may be naturally occurring (but not necessarily proteinogenic) amino acids and/or synthetic amino acids. Preferably, the amino acids in the peptide component are naturally occurring amino acids.

For example, at least one of the amino acids that is not present at the N-terminal of the peptide component may comprise asparagine (Asn), more preferably arginine (Arg), and even more preferably lysine (Lys).

In this respect, it is preferred that at least about 5%, more preferably at least about 10%, such as at least about 15%, including at least about 20% (by number and/or by weight) of the amino acids that are present in the peptide component comprise such amino acids (i.e. Asn, Arg and/or Lys).

The peptide component of the compounds of the invention may be a homopolymer of an amino acid. Alternatively, the peptide component of the compounds of the invention may be a heteropolymer of two or more different amino acids. Preferably, the peptide component of the compounds of the invention is a heteropolymer of two or more different naturally occurring amino acids (e.g. at least three different amino acids, preferably four different amino acids, most preferably at least five different amino acids).

Peptide components that may be coupled to compounds of formula I include peptides that have known anti-microbial and/or anti-inflammatory properties, or fragments, or minor variants, thereof.

Fragments of such peptides include "parts" of the full amino acid sequence that may display such anti-microbial and/or anti-inflammatory properties.

Also included are amino acid sequences that are (e.g. minor) variants of, such full amino acid sequences, or fragments thereof, which may be synthesized by chemical and/or biological processes (e.g. chemical modifications of naturally-occurring peptides, or by direct synthesis). By "(e.g. minor) variants of full amino acid sequences, or fragments thereof", we mean variations in those respective sequences that do not negatively affect the requisite properties of the relevant full peptide or fragment thereof to a measurable degree.

Antimicrobial peptides that may be mentioned in this regard include a cecropin, such as cecropin A:

(SEQ ID No: 1)
H-Lys-Trp-Lys-Leu-Phe-Lys-Lys-Ile-Glu-Lys-Val-Gly-

Gln-Asn-Ile-Arg-Asp-Gly-Ile-Ile-Lys-Ala-Gly-Pro-

Ala-Val-Ala-Val-Val-Gly-Gln-Ala-Thr-Gln-Ile-Ala-

Lys-NH$_2$;

cecropin B:
(SEQ ID No: 2)
H-Lys-Trp-Lys-Val-Phe-Lys-Lys-Ile-Glu-Lys-Met-Gly-

Arg-Asn-Ile-Arg-Asn-Gly-Ile-Val-Lys-Ala-Gly-Pro-

Ala-Ile-Ala-Val-Leu-Gly-Glu-Ala-Lys-Ala-Leu-NH$_2$
and/or

LL-37:
(SEQ ID No: 3)
H-Leu-Leu-Gly-Asp-Phe-Phe-Arg-Lys-Ser-Lys-Glu-Lys-

Ile-Gly-Lys-Glu-Phe-Lys-Arg-Ile-Val-Gln-Arg-Ile-

Lys-Asp-Phe-Leu-Arg-Asn-Leu-Val-Pro-Arg-Thr-Glu-

Ser-NH$_2$.

Antiinflammatory peptides that may be mentioned include amino acid sequences that are fragments of mussel adhesive protein (MAP), also known as *Mytilus edulis* foot protein (mefp), which is a protein secreted by marine shellfish species, such as *Mytilus edulis, Mytilus coruscus* and *Perna viridis*, including the eleven identified separate adhesive protein subtypes that have been derived from mussels, including the collagens pre-COL-P, pre-COL-D and pre-COL-NG; the mussel feet matrix proteins PTMP (proximal thread matrix protein) and DTMP (distal proximal thread matrix protein); and mfp proteins mfp-2 (sometimes referred to as "mefp-2", hereinafter used interchangeably), mfp-3/mefp-3, mfp-4/mefp-4, mfp-5/mefp-5, mfp-6/mefp-6 and, most preferably mfp-1/mefp-1 (see, for example, Zhu et al, *Advances in Marine Science*, 32, 560 (2014) and Gao et al, *Journal of Anhui Agr. Sci.*, 39, 19860 (2011)).

A significant portion of mefp-1 consists of 70 to 90 tandem repeats of the decapeptide: Ala-Lys-Pro-Ser-Tyr-Hyp-Hyp-Thr-DOPA-Lys (SEQ ID No: 4; see Waite, *Int. J. Adhesion and Adhesives*, 7, 9 (1987)). This decapeptide sequence may be isolated as a low molecular weight derivative of naturally-occurring MAPs, or may be synthesized, for example as described by Yamamoto in *J. Chem. Soc., Perkin Trans.* 1, 613 (1987). See also Dalsin et al, *J. Am. Chem. Soc.*, 125, 4253 (2003).

In this respect, the peptide component that may be employed in compounds of the invention include one to four (preferably three and more preferably two) repeat units of the above-mentioned decapeptide sequence, or most preferably one of the above-mentioned decapeptide sequences, or variants (as hereinbefore defined) of any of these options.

There is further provided a peptide-containing compound as hereinbefore defined in which at least about 5%, such at least about 10% (by number) of the amino acids in the peptide component contain aromatic groups, such as tyrosine and/or 3,4-dihydroxyphenylalanine (DOPA). Alternatively, none of the amino acids in the peptide chain contain aromatic groups, i.e. none of the amino acids are tyrosine and/or DOPA.

It is further preferred that the peptide component within a compound of the invention comprises between 5 and 30 amino acids, such as between 6 and 20 amino acids, including between 7 and 15 (e.g. up to 12, such as 10) amino acids in the amino acid sequence.

Compounds of the invention that may be mentioned in this regard include those in which the peptide component is of the amino acid sequence:

(SEQ ID No: 5)
X-Pro-Y-Z, wherein:
X represents a chain of 1 to 2 amino acid residues each independently selected from the group consisting of Ala and Lys;
Y is selected from the group consisting of Ser and pSer;

Z represents a chain of 1 (e.g. 2, such as 3) to 7 amino acid residues each independently selected from the group consisting of Tyr, pTyr, Hyp (i.e. 3Hyp or 4Hyp), Thr, pThr, DOPA and Lys; and at least one of the Ala and/or Lys residues is bonded to one or more compounds of formula I, as hereinbefore defined.

A particular amino acid sequence that may be mentioned is (SEQ ID No: 6)
Ala-Pro-Ser-Hyp-Hyp-Thr Preferred compounds of the invention that may be mentioned include those in which the peptide component is of the amino acid sequence:

(SEQ ID No: 7)
$G^1$-Lys-Pro-$G^2$-T-Hyp-$G^3$-Lys, wherein:
$G^1$ is absent or represents Ala;
$G^2$ is selected from the group consisting of Ser and pSer;
T is selected from the group consisting of DOPA or, more preferably, Tyr and pTyr;
Hyp is selected from the group consisting of 3Hyp and 4Hyp;
$G^3$ represents a chain of 1 to 4 (e.g. 1 to 3) amino acid residues each independently selected from the group consisting of Tyr, pTyr, 3Hyp, 4Hyp, Thr, pThr and DOPA; and
at least one of the Lys residues, and/or, where present, the Ala residue, is bonded to one or more compounds of formula I, as hereinbefore defined.

Peptide components that may be mentioned include those of the amino acid sequence:

(SEQ ID No: 8)
Lys-Pro-$G^2$-T-Hyp-$G^3$-Lys, wherein $G^2$, T, Hyp and $G^3$ are defined above, with $G^2$ being more preferably Ser and $G^3$ being more preferably Tyr or, especially, DOPA.

However, it is further preferred that:
$G^1$ represents Ala;
$G^2$ represents Ser;
T represents Tyr;
$G^3$ represents 1 to 4 (e.g. 1 to 3) amino acid residues each independently selected from the group consisting of Tyr, 3Hyp, 4Hyp and Thr, such as the chain of amino acids is represented by -$V^1$-Thr-Tyr-$V^2$—, wherein $V^1$ is bonded to Hyp and $V^2$ is bonded to Lys, and $V^1$ and $V^2$ are, independently, either absent or represent one or two Hyp groups.

In this respect the sequence -$V^1$-Thr-Tyr-$V^2$ may be represented, in increasing order of preference by the part-sequences:

-Hyp-Thr-Tyr-

-Hyp-Thr-Tyr-Hyp-
or,

-Thr-Tyr-Hyp-.

Thus, preferred peptide components include those of the amino acid sequence:

(SEQ ID No: 9)
Ala-Lys-Pro-$G^2$-T-Hyp-Hyp-Thr-$G^4$-Lys, wherein $G^2$, T, and Hyp are defined above and $G^4$ is selected from the group consisting of Tyr, pTyr, 3Hyp, 4Hyp, Thr, pThr and DOPA, with $G^2$ being more preferably Ser, T being more preferably Tyr and $G^4$ being more preferably Tyr or DOPA.

Preferred peptide components further include those of the amino acid sequence:

(SEQ ID No: 10)
Ala-Lys-Pro-G2-T-Hyp-Thr-$G^4$-Hyp-Lys, wherein $G^2$, T, Hyp and $G^4$ are defined above, with and $G^4$ is being more preferably DOPA or, especially, Tyr.

Preferred peptide components include those of the amino acid sequence:

(SEQ ID No: 4)
Ala-Lys-Pro-Ser-Tyr-Hyp-Hyp-Thr-DOPA-Lys;

(SEQ ID No: 11)
Ala-Lys-Pro-pSer-Tyr-Hyp-Hyp-Thr-DOPA-Lys;

(SEQ ID No: 12)
Ala-Lys-Pro-Ser-Tyr-Hyp-Hyp-Thr-Tyr-Lys;

(SEQ ID No: 13)
Ala-Lys-Pro-pSer-Tyr-Hyp-Hyp-Thr-Tyr-Lys;

(SEQ ID No: 14)
Lys-Pro-Ser-Tyr-Hyp-DOPA-Lys;
and (SEQ ID No: 15)
Lys-Pro-Ser-pTyr-Hyp-DOPA-Lys.

In the above list of amino acid sequences, (SEQ ID No: 12)
Ala-Lys-Pro-Ser-Tyr-Hyp-Hyp-Thr-Tyr-Lys is most preferred.

Further preferred peptide components include those of the amino acid sequence:

(SEQ ID No: 16)
Ala-Lys-Pro-Ser-Tyr-Hyp-Hyp-pThr-DOPA-Lys
and (SEQ ID No: 17)
Ala-Lys-Pro-Ser-Tyr-Hyp-Hyp-pThr-Tyr-Lys.

Further preferred peptide components include those of the amino acid sequence:

(SEQ ID No: 18)
Ala-Lys-Pro-Ser-Tyr-Hyp-Hyp-Thr-DOPA-Hyp-Lys;

(SEQ ID No: 19)
Ala-Lys-Pro-pSer-Tyr-Hyp-Hyp-Thr-DOPA-Hyp-Lys;

(SEQ ID No: 20)
Ala-Lys-Pro-Ser-Tyr-Hyp-Hyp-Thr-Tyr-Hyp-Lys;

(SEQ ID No: 21)
Ala-Lys-Pro-pSer-Tyr-Hyp-Hyp-Thr-Tyr-Hyp-Lys;

(SEQ ID No: 22)
Ala-Lys-Pro-Ser-Tyr-Hyp-Thr-DOPA-Hyp-Lys,

```
                                            (SEQ ID No: 23)
Ala-Lys-Pro-pSer-Tyr-Hyp-Thr-DOPA-Hyp-Lys;

(SEQ ID No: 24)
Ala-Lys-Pro-Ser-Tyr-Hyp-Thr-Tyr-Hyp-Lys;

(SEQ ID No: 25)
Ala-Lys-Pro-pSer-Tyr-Hyp-Thr-Tyr-Hyp-Lys;

(SEQ ID No: 26)
Ala-Lys-Pro-Ser-Tyr-Hyp-Hyp-pThr-DOPA-Hyp-Lys;
and (SEQ ID No: 27)
Ala-Lys-Pro-Ser-Tyr-Hyp-Hyp-pThr-Tyr-Hyp-Lys.
```

In the above list of amino acid sequences,

```
                                            (SEQ ID No: 24)
    Ala-Lys-Pro-Ser-Tyr-Hyp-Thr-Tyr-Hyp-Lys
``` is most preferred.

Further preferred peptide components include those of the amino acid sequence:

```
                                            (SEQ ID No: 28)
Ala-Lys-Pro-Ser-Tyr-Hyp-Hyp-Thr-DOPA;

(SEQ ID No: 29)
Ala-Lys-Pro-pSer-Tyr-Hyp-Hyp-Thr-DOPA;

(SEQ ID No: 30)
Ala-Lys-Pro-Ser-Tyr-Hyp-Hyp-Thr-Tyr;

(SEQ ID No: 31)
Ala-Lys-Pro-pSer-Tyr-Hyp-Hyp-Thr-Tyr;

(SEQ ID No: 32)
Lys-Pro-Ser-Tyr-Hyp-DOPA;

(SEQ ID No: 33)
Lys-Pro-Ser-pTyr-Hyp-DOPA;

(SEQ ID No: 34)
Ala-Lys-Pro-Ser-Tyr-Hyp-Hyp-pThr-DOPA;

(SEQ ID No: 35)
Ala-Lys-Pro-Ser-Tyr-Hyp-Hyp-pThr-Tyr;

(SEQ ID No: 36)
Ala-Lys-Pro-Ser-Tyr-Hyp-Hyp-Thr-DOPA-Hyp;

(SEQ ID No: 37)
Ala-Lys-Pro-pSer-Tyr-Hyp-Hyp-Thr-DOPA-Hyp;

(SEQ ID No: 38)
Ala-Lys-Pro-Ser-Tyr-Hyp-Hyp-Thr-Tyr-Hyp;

(SEQ ID No: 39)
Ala-Lys-Pro-pSer-Tyr-Hyp-Hyp-Thr-Tyr-Hyp;

(SEQ ID No: 40)
Ala-Lys-Pro-Ser-Tyr-Hyp-Thr-DOPA-Hyp, (SEQ ID No: 41)
Ala-Lys-Pro-pSer-Tyr-Hyp-Thr-DOPA-Hyp;

(SEQ ID No: 42)
Ala-Lys-Pro-Ser-Tyr-Hyp-Thr-Tyr-Hyp;

(SEQ ID No: 43)
Ala-Lys-Pro-pSer-Tyr-Hyp-Thr-Tyr-Hyp;

(SEQ ID No: 44)
Ala-Lys-Pro-Ser-Tyr-Hyp-Hyp-pThr-DOPA-Hyp;

(SEQ ID No: 45)
Ala-Lys-Pro-Ser-Tyr-Hyp-Hyp-pThr-Tyr-Hyp (SEQ ID No: 46)
Ala-Lys-Pro-Ser-Tyr-Hyp-Hyp;
and (SEQ ID No: 47)
Ala-Lys-Pro-Ser-Tyr-Hyp.
```

The skilled person will appreciate that metabolites of compounds of the invention that may be formed following administration are included within the scope of the invention.

In particular, compounds of the invention comprising peptide components with amino acid sequences SEQ ID No: 28 to SEQ ID No: 47 may be formed as metabolites of corresponding compounds of the invention comprising relevant amino acids at the C-terminus, which may be cleaved from other compounds of the invention following administration.

For example, compounds of the invention comprising peptide components with amino acid sequences SEQ ID No: 30, SEQ ID No: 46 and SEQ ID No: 47 may be formed as metabolites of compounds of the invention comprising peptide components with the amino acid sequence SEQ ID No: 12. Similarly, compounds of the invention comprising peptide components with amino acid sequence SEQ ID No: 42 and SEQ ID No: 47 may be formed as metabolites of compounds of the invention comprising peptide components with the amino acid sequence SEQ ID No: 24.

Nevertheless, compounds of the invention comprising peptide components with amino acid sequences SEQ ID No: 28 to SEQ ID No: 47 are also compounds of the invention in their own right and may be made, formulated and administered to patients in exactly the same fashion as other compounds of the invention that are described herein and/or exemplified below.

For the avoidance of doubt, as used herein, Pro represents proline, Ala represents alanine, Ser represents serine and pSer represents phosphoserine, Tyr represents tyrosine, pTyr represents phosphotyrosine, Hyp represents hydroxyproline (3Hyp represents 3-hydroxyproline and 4Hyp represents 4-hydroxyproline). Thr represents threonine, pThr represents phosphothreonine (or phosphonothreonine). and Lys, Ala and DOPA are as hereinbefore defined. Phosphonated derivatives of amino acids that comprise a free hydroxy group (e.g. Ser, Tyr and Thr) comprises the group —OP(=O)(OH)$_2$ instead of —OH.

One or more compounds of formula I may be linked to the aforementioned peptide component through one or more e.g. Ala or Lys moieties, including through an N-terminal Ala or Lys moiety and/or a C-terminal Lys moiety.

Three compounds of formula I, preferably two compounds of formula I, and more preferably one compound of formula I may be covalently bonded to the aforementioned peptide component in a compound of the invention.

It is advantageous that the peptide component of compounds of the invention comprises at least one amino acid residue that contains at least one free —NH$_2$ group. Particular amino acid residues that contain at least one free —NH$_2$ group include Asn, Gln, preferably Arg and most preferably Lys. For example, when the peptide component is a sequence of (SEQ ID No: 7)
G¹-Lys-Pro-G²-T-Hyp-G₃-Lys at least one of the Lys residues has a free —NH₂ group (i.e. least one of the Lys residues is not covalently bonded to a compound of formula I group).

In examples of compounds of the invention where two or more (e.g. three, preferably two) compounds of formula I are covalently bonded to the peptide component, it is preferred that the peptide component comprises at least one amino acid residue that that contains at least one free —NH₂ group. For example, the peptide component comprises at least one Lys residue that is not covalently bonded to a compound of formula I.

Without wishing to be bound by theory, it is believed that the presence of free —NH₂ groups in the peptide component (e.g. when one or more of the Lys residues that may be present are not covalently bonded to a compound of formula I) is beneficial to the (e.g. aqueous) solubility of the compounds of the invention.

Compounds of formula I contain a double bond and may thus exist as E (entgegen) and Z (zusammen) geometric isomers about the double bond. All such isomers and mixtures thereof are included within the scope of the invention. For the avoidance of doubt, ⁓ in compounds of formula I indicate that the 7-chloroquinoline ring may be located either cis (as the Z geometric isomer) or trans (as the E geometric isomer) across the double bond to the central 1,3-disubstituted phenyl ring. Preferably the 7-chloroquinoline ring is located trans across the double bond to the central 1,3-disubstituted phenyl ring i.e. the E geometric isomer.

Particular compounds of formula I that may be mentioned include those in which R¹ is selected from the group consisting of —C(CH₃)₂OH, —COCH₃ and —C(CH₃)=CH₂.

Preferred compound of formula I include those in which R¹ is —C(CH₃)₂OH and/or n is 0 (e.g. montelukast).

For the avoidance of doubt, montelukast has the following chemical structure:

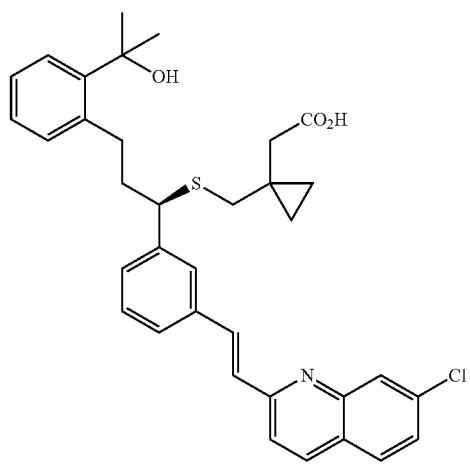 [SMILES: CC(C)(O)c1ccccc1CC[C@@H](SCC1(CC(=O)O)CC1)c1cccc(/C=C/c2ccc3ccc(Cl)cc3n2)c1]

Other compounds of formula I include those in which R¹ is —C(CH₃)=CH₂ and/or n is 0 (e.g. montelukast styrene).

For the avoidance of doubt, montelukast styrene has the following chemical structure:

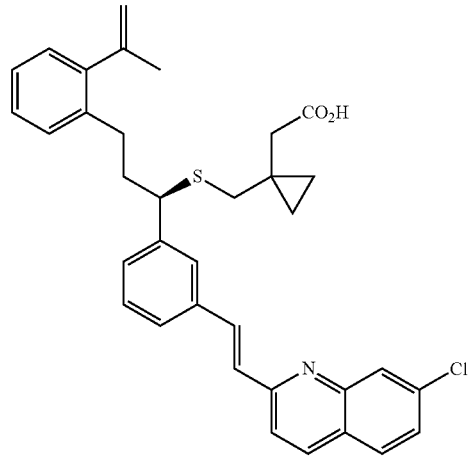 [SMILES: C=C(C)c1ccccc1CC[C@@H](SCC1(CC(=O)O)CC1)c1cccc(/C=C/c2ccc3ccc(Cl)cc3n2)c1]

Other compounds of formula I that may be mentioned include those in which R¹ is —C(CH₃)₂H and/or n is 0 (e.g. hydrogenated montelukast styrene).

For the avoidance of doubt, hydrogenated montelukast styrene has the following chemical structure:

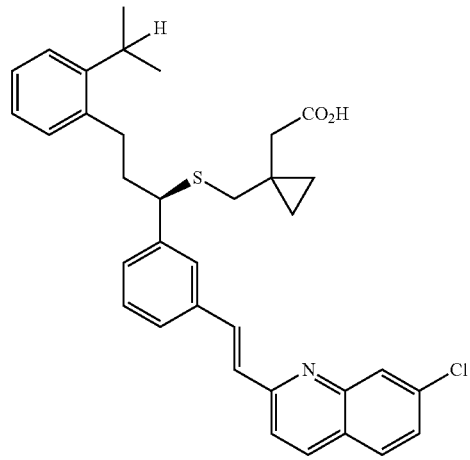 [SMILES: CC(C)c1ccccc1CC[C@@H](SCC1(CC(=O)O)CC1)c1cccc(/C=C/c2ccc3ccc(Cl)cc3n2)c1]

Compounds of the invention, whether in the form of salts or otherwise, include regioisomers within amino acids of the peptide component (for example Hyp and Tyr moieties), as well as mixtures of such regioisomers. For example, included within the definition of Tyr are, not only tyrosine (4-hydroxyphenylalanine), but also 2- and 3-hydroxyphenylalanine, and included within the definition of Hyp are 4-hydroxyproline (4Hyp), 3-hydroxyproline (3Hyp) and 5-hydroxyproline (5Hyp). It is more preferred that Hyp residues are 4-hydroxyproline.

Also, in addition to the standard central carbon atom of the amino acids in the peptide component of compounds of the invention (which are normally but not exclusively in the L-configuration), certain amino acids in the sequence comprise further chiral carbon atoms. All such stereoisomers and mixtures (including racemic mixtures) thereof are included within the scope of the invention. In respect, included within the definition of Hyp are trans-4-hydroxy-L-proline, cis-4-hydroxy-L-proline, trans-3-hydroxy-L-proline, cis-3-hydroxy-L-proline trans-5-hydroxy-L-proline and cis-5-hydroxy-L-proline, however we prefer that the Hyp that is employed in compounds of the invention is 4-hydroxy-L-proline. Similarly, individual enantiomers of compounds of formula I that may form part of a compound of the invention are included within the scope of the invention.

Compounds of the invention may be in the form of salts. Salts that may be mentioned include pharmaceutically-acceptable and/or cosmetically-acceptable salts, such as pharmaceutically- and/or cosmetically-acceptable acid addition salts and base addition salts. Such salts may be formed by conventional means, for example by reaction of a compound of the invention with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of active ingredient in the form of a salt with another counter-ion, for example using a suitable ion exchange resin.

Preferred salts include, for example, acetate, hydrochloride, bisulfate, maleate, mesylate, tosylate, alkaline earth metal salts, such as calcium and magnesium, or alkali metal salts, such as sodium and potassium salts. Most preferably, compounds of the invention may be in the form of acetate salts.

Compounds of the invention may be prepared by way of conventional techniques. For example, a compound of the invention may be made by coupling one or more compounds of formula I to the peptide component, for example as described hereinafter. Compounds of the invention (and peptide components thereof) may be synthesized from available starting materials using appropriate reagents and reaction conditions. In this respect, the skilled person may refer to inter alia "*Comprehensive Organic Synthesis*" by B. M. Trost and I. Fleming, Pergamon Press, 1991. Further references that may be employed include "*Heterocyclic Chemistry*" by J. A. Joule, K. Mills and G. F. Smith, 3$^{rd}$ edition, published by Chapman & Hall, "*Comprehensive Heterocyclic Chemistry II*" by A. R. Katritzky, C. W. Rees and E. F. V. Scriven, Pergamon Press, 1996 and "*Science of Synthesis*", Volumes 9-17 (Hetarenes and Related Ring Systems), Georg Thieme Verlag, 2006.

The peptide component of component of the invention may, if necessary, be made by standard peptide synthesis techniques, using standard amino acid coupling techniques, and standard coupling reagents and solvents, for example as described hereinafter.

The skilled person will understand that the substituents as defined herein, and substituents thereon, may be modified one or more times, after or during the processes described above for the preparation of compounds of the invention by way of methods that are well known to those skilled in the art. Examples of such methods include substitutions, reductions, oxidations, dehydrogenations, alkylations, dealkylations, acylations, hydrolyses, esterifications, etherifications, halogenations and nitrations. Precursor groups may be changed to a different such group, or to the groups defined in a compound of the invention, at any time during the reaction sequence. The skilled person may also refer to "*Comprehensive Organic Functional Group Transformations*" by A. R. Katritzky, O. Meth-Cohn and C. W. Rees, Pergamon Press, 1995 and/or "*Comprehensive Organic Transformations*" by R. C. Larock, Wiley-VCH, 1999.

Compounds of the invention may be isolated from their reaction mixtures and, if necessary, purified using conventional techniques as known to those skilled in the art. Thus, processes for preparation of compounds of the invention as described herein may include, as a final step, isolation and optionally purification of the compound of the invention.

It will be appreciated by those skilled in the art that, in the processes described above and hereinafter, the functional groups of intermediate compounds may need to be protected by protecting groups. The protection and deprotection of functional groups may take place before or after a reaction in the above-mentioned schemes.

Protecting groups may be applied and removed in accordance with techniques that are well-known to those skilled in the art and as described hereinafter. For example, protected compounds/intermediates described herein may be converted chemically to unprotected compounds using standard deprotection techniques. The type of chemistry involved will dictate the need, and type, of protecting groups as well as the sequence for accomplishing the synthesis. The use of protecting groups is fully described in "*Protective Groups in Organic Synthesis*", 3rd edition, T. W. Greene & P. G. M. Wutz, Wiley-Interscience (1999), the contents of which are incorporated herein by reference.

Compounds of the invention are useful because they possess pharmacological activity. Thus, the compounds of the invention are useful as human and animal medicine. They are therefore indicated as pharmaceuticals (and/or in veterinary science), although they may also be used as cosmetics and/or as part of a medical device.

Although compounds of the invention may possess pharmacological activity as such, certain pharmaceutically-acceptable (e.g. "protected") derivatives of compounds of the invention may exist or may be prepared which may not possess such activity, but which may be administered and thereafter be metabolised or chemically transformed to form compounds of the invention. Such compounds (which may possess some pharmacological activity, provided that such activity is appreciably lower than that of the active compounds to which they are metabolised/transformed) may therefore be described as "prodrugs" of compounds of the invention.

As used herein, references to prodrugs will include compounds that form a compound of the invention, in an experimentally-detectable amount, within a predetermined time, following administration. All prodrugs of the compounds of the invention are included within the scope of the invention.

Compounds of the invention are particularly useful in the treatment of inflammation.

The "treatment of inflammation" includes the treatment of inflammation in any organ of the body (including soft tissue, joints, nerves, the vascular system, internal organs, especially mucosal surfaces, and particularly the skin), irrespective of the cause, and also includes all such inflammatory disorders or conditions, and/or disorders or conditions characterized by inflammation (e.g. as a symptom).

Inflammatory conditions may be (and are typically) characterized by activation of immune defence mechanisms, resulting in an effect that is more harmful than beneficial to the host. Such conditions are generally associated with varying degrees of tissue redness or hyperemia, swelling, edema, hyperthermia, pain (including aching), exudation of body fluids, itching (pruritis), cell death and tissue destruction, cell proliferation, and/or loss of function.

Inflammatory conditions that may be mentioned include arteritis, diabetes mellitus, metabolic syndrome, rosacea, asthma and allergy, ankylosing spondylitis, chronic obstructive pulmonary disease, gouty arthritis, inflammatory bowel disease (such as Crohn's disease and ulcerative colitis), multiple sclerosis, osteoarthritis, pancreatitis, prostatitis, psoriatic arthritis, rheumatoid arthritis, tendinitis, bursitis, Sjogren's syndrome, systemic lupus erythematosus, uveitis, urticaria, vasculitis, mastocytosis, diabetic vascular complications, migraine, atherosclerosis and associated cardiovascular disorders. A disease state characterised by inflammation that may be mentioned is chronic obstructive pulmonary disease (COPD). A further disease state characterised by inflammation that may be mentioned is inflammatory bowel diseases including Crohn's disease and, especially, ulcerative colitis.

Inflammatory conditions that may be more especially mentioned include inflammations of the skin or mucosa (including the oral, nasal, ocular, vaginal, cervical and/or anorectal mucosae, more particularly the oral or nasal mucosae), such as inflammation resulting from infections (such as viral and/or bacterial infections), or allergic/atopic conditions (such as rhinitis (e.g. allergic rhinitis), pharyngitis, periodontitis, gingivitis, xerophthalmia, conjunctivitis (e.g. allergic conjunctivitis), dermatitis, urticaria (hives) and food allergy); and other inflammatory conditions, such as herpes, drug eruptions, polymorphous light eruptions, sunburn, early manifestations of skin cancers (erythema-like skin lesions), pathological hair loss (including following skin grafting), chemo rash, psoriasis, erythema multiforme, folliculitis, eczema and external otitis. A disease state that may be mentioned is polymorphous light eruptions.

More particularly, compounds may be used to treat certain conditions characterized by inflammation, and/or with which inflammation is associated. Such conditions may include wounds (including abrasions (scratches), incisions (including operative incisions), lacerations, punctures, avulsions, bruising and scarring), and burns (including inflammation resulting from surgery following burns, such as skin grafting) and other conditions, such as hemorrhoids. Wounds may be acute or chronic, and/or may result from one or more inflammatory disorders as defined herein.

Wounds of the skin or mucosa may arise from internal or external physical injury to the membrane surface, or may be caused by (i.e. be a symptom of) an underlying physiological disorder.

Physical (e.g. "open") wounds may be caused by sharp objects (cuts, incisions, punctures) or blunt objects/mechanical forces (lacerations, abrasions, avulsions), physical blows (bruises), heat or chemicals (burns and blisters), UV light (sunburn), cold (chilblains or frostbite). Wounds may be superficial (damage only to the epidermis and/or dermis) or may be full thickness wounds (damage below the epidermis and/or dermis). In serious cases, subcutaneous and/or submucosal tissues, such as muscles, bones, joints, and even internal organs, may be damaged.

Compounds of the invention may be used to relieve the pain (including aching) associated with inflammation and/or wounding. In particular, compounds of the invention may be used to relieve procedural pain and/or non-procedural pain. The skilled person will understand that the term "procedural pain" (i.e. operation pain) refers to acute pain that is associated with medical investigations and treatments conducted for the purpose of healthcare. The term "non-procedural" refers to general pain that is associated with inflammation and/or wounding (e.g. pain associated with dental ulcers, burns and/or scars), and is not a consequence of a particular medical intervention.

Compounds of the invention may be used to treat not only the inflammation, pain (including aching) and/or pruritis (itching) associated with the wound itself and the healing process, but also they may be used to prevent the exudation of body fluids from wounds, the risk of infection, and also the prevention of physiological reactions that result from inflammation and/or wound healing processes, such as scarring and melanin pigmentation.

Scarring is a consequence of inflammation and/or wound healing and is a general term for the formation of fibrotic tissue that is a consequence of such inflammation/healing.

Compounds of the invention may also be useful in the suppression of the production of melanin pigmentation, which may or may not result from inflammation and/or wound healing. Compounds of the invention may also be useful in the suppression of disorders associated with melanin pigmentation, such as chloasma, freckles, melanosis, malar rash and other chromatosis, skin cancers with melanoma, and chromatosis that is caused by exposure to the sun or skin diseases like acne.

Wounds may also arise as a consequence of (e.g. inflammatory) diseases or disorders. Such wounds may include blistering and/or ulcers of the skin and mucosa. These are common conditions that are often long-lasting and difficult to treat. Skin tissues can often be damaged, removed, liquefied, infected and/or necrotic. Ulcers can lead to secondary consequences to health particularly if they become infected, are hard to heal and are costly to treat. They can also cause significant psychological stress and economic loss to patients, affecting both general well-being and quality of life.

In the alternative, inflammatory skin conditions or diseases in which compounds of the invention find particular utility include psoriasis, acne, eczema and dermatitis, especially allergic/atopic dermatitis, as well as in the treatment of mucosal inflammation as characterized by rhinitis, especially allergic rhinitis, hemorrhoids, chronic obstructive pulmonary disease and ulcerative colitis, for example.

Psoriasis is a chronic, inflammatory skin disease with a tendency to recur (some patients never heal during their entire life). Clinical manifestations of psoriasis mainly include erythema and scales. It can occur over the whole body, but is more commonly observed on the scalp and limbs.

Acne is a follicular (pilosebaceous unit) chronic, inflammatory skin disease, the occurrence of which is closely related to main factors like hypersteatosis, blocked pilosebaceous ducts (including closed and open comedones), bacterial infection and inflammatory reactions, that tends to occur during youth, characterised by multiform skin lesions on the face. The term acne thus includes regular acne and acne rosacea (i.e. copper nose).

Eczema is a skin inflammatory reaction with strong itching caused by a variety of internal and external factors. It has three phases, acute, sub-acute, and chronic. In the acute phase, there is a tendency for the production of exudates, while the chronic phase includes infiltration and hypertrophy. Skin lesions are often itchy and recur easily.

Dermatitis is a common skin disease characterised by coarseness, redness, itching, eczema, and dryness. Small lumps, refractory ulcers, and pigmented spots caused by dermatitis may, if not treated promptly, develop to basal cell carcinoma, squamous cell carcinoma, and malignant melanoma. Dermatitis may be caused by various internal and external infectious or non-infectious factors, including substances (contact dermatitis) or allergy (allergic/atopic dermatitis). Also included is seborrheic dermatitis (seborrheic eczema) and all forms of steroid-dependent dermatitis (including light-sensitive seborrheid, perioral dermatitis, rosacea-like dermatitis, steroid-rosacea, steroid-induced rosacea, iatrosacea, steroid dermatitis resembling rosacea, topical corticosteroid-induced rosacea-like dermatitis and, more particularly, facial corticosteroid addictive dermatitis (FCAD) or facial corticosteroid-dependent dermatitis (FCDD), as characterised by flushing, erythema, telangiectasia, atrophy, papules and/or pustules in the facial area after long-term treatment with (including uncontrolled use, abuse or misuse of) topical corticosteroids; see, for example, Xiao et al, *J. Dermatol.*, 42, 697 (2015) and Lu et al, *Clin. Exp. Dermatol.*, 35, 618 (2009)).

Rhinitis is irritation and inflammation of the mucous membrane inside the nose. Common symptoms of rhinitis include a stuffy nose, runny nose, sneezing and post-nasal drip. The most common kind of rhinitis is allergic rhinitis, caused by an allergen, such as pollen, dust, mould, or flakes of skin from certain animals. It has been surprisingly found that patients with allergic rhinitis who were treated compounds of the invention experienced relief of eye itchiness, even when compounds of the invention were administered nasally (i.e. to the nasal mucosa).

Hemorrhoids are swellings caused by inflammation of the hemorrhoidal blood vessels found inside or around the rectum and anus. Symptoms include bleeding (i.e. wounding) after the passage of a stool, prolapse of the hemorrhoid, mucus discharge and itchiness, soreness, redness and swelling in the area of the anus. Hemorrhoids are believed to be a consequence of an increase of pressure in the abdomen, for example, as a result of constipation or diarrhea.

Chronic obstructive pulmonary disease (COPD) is the name for a group of lung conditions that cause breathing difficulties, including emphysema (damage to the alveoli) and chronic bronchitis (long-term inflammation of the airways). COPD occurs when the lungs become inflamed, damaged and narrowed. The damage to the lungs is usually irreversible and results in an impairment of the flow of air into and out of the lungs. Symptoms of COPD include breathlessness, productive cough, frequent chest infections and persistent wheezing. The most common cause of the disease is smoking, although other risk factors include high levels of air pollution and occupational exposure to dust, chemicals and fumes.

Compounds of the invention may have positive effects in mitigating erythema, redness and swelling, edema, blisters, and bullous pemphigoid caused by various conditions including those mentioned generally and specifically herein, and may inhibit exudation of subcutaneous tissue fluid, and suppressing itching and pain caused by such inflammatory conditions.

Other inflammatory conditions that may be mentioned include:

(a) Mucosal inflammation, such as oral mucositis, aphthous ulcers, otitis media, laryngitis, tracheitis, esophagitis, gastritis, enteritis and enterocolitis (including bacillary dysentery, chronic amoebic dysentery, schistosomiasis, nonspecific ulcerative colitis and regional enteritis), cervicitis and endocervicitis, endometritis, inflammation caused by inhalation injury and the like, as well as mucosal inflammation associated with cancers, and infections (e.g. viral infections, such as the common cold or influenza), that affect mucosal surfaces, such as those in the oral cavity, the nasopharynx, the ear, the throat, the trachea, the gastrointestinal tract, the cervix, etc.

(b) Orthopedic inflammation associated with, for example bone fractures, pyogenic infection of bones and joints, inflammation caused by rheumatic bone diseases, as well as pyogenic osteomyelitis (acute, chronic, localized, sclerotic, post-traumatic), pyogenic arthritis; bone tumors (osteoma, osteoid osteoma, chondroma), bone cysts, osteoclastoma, primary bone sarcoma (osteosarcoma, chondrosarcoma, osteofibrosarcoma, Ewing's sarcoma, non-Hodgkin's lymphoma, myeloma, chordoma), metastatic bone tumors, tumor-like lesions of bone (bone cyst, aneurysmal bone cyst, eosinophilic granuloma, fibrous dysplasia); and rheumatic arthritis.

(c) Nerve inflammation, such as peripheral polyneuritis, facial neuritis, peripheral neuritis, subcutaneous neuritis, ulnar neuritis, intercostal neuritis, etc.

(d) Subcutaneous and submucosal soft tissue inflammation, such as myositis, ligamentitis, tendonitis, panniculitis capsulitis, lymphadenitis, bubonadenitis, tonsillitis, synovitis, fasciitis, and soft tissue inflammation caused by injuries, contusion or laceration of muscles, ligaments, fascia, tendons, membrana synovialis, fat, articular capsules, and lymphoid tissue.

(e) Vascular inflammation, such as allergic leukocytoclastic vasculitis, allergic cutaneous vasculitis, polyarteritis nodosa, thrombotic vasculitis, granulomatous vasculitis, lymphocytic vasculitis, vasculitis with abnormalities in blood composition, and rheumatic vasculitis, as well as vascular inflammation associated with vascular cancers caused by allergic leukocytoclastic vasculitis, polyarteritis nodosa, thrombotic vasculitis, granulomatous vasculitis, lymphocytic vasculitis, vasculitis with abnormalities in blood composition, and rheumatic vasculitis.

(f) Inflammation of the internal organs, such as the heart, stomach, intestine, lung, liver, spleen, kidney, pancreas, bladder, ovary, and prostate, including but not limited to pericarditis, myocarditis, endocarditis, pneumonia, hepatitis, splenitis, nephritis pancreatitis, cystitis, oophoritis, prostatitis and treatment of gastric ulcer.

(g) Inflammation of the eye and surrounding area, such as conjunctivitis, keratitis (e.g. acute epithelial keratitis, nummular keratitis, interstitial keratitis, disciform keratitis, neurotrophic keratitis, mucous plaque keratitis, herpes simplex keratitis, herpes zoster keratitis, bacterial keratitis, fungal keratitis acanthamoebic keratitis, onchocercal keratitis, superficial punctate keratitis, ulcerative keratitis, exposure keratitis photokeratitis and contact lens acute red eye), optic neuritis, etc.

(h) Inflammation of the gums and the oral cavity, such as periodontitis, gingivitis, dental ulcers, etc.

(i) Inflammation associated with rheumatism, such as rheumatic vasculitis, rheumatoid arthritis, rheumatic bone diseases, ankylosing spondylitis, bursitis, Crohn's disease, gout, infectious arthritis, juvenile idiopathic arthritis, osteoarthritis, osteoporosis, polymyalgia rheumatica, polymyositis, psoriatic arthritis, scleroderma, Sjogren's syndrome, spondyloarthropathies, systemic lupus erythematosus, tendinitis, etc.

Compounds of the invention may also be used in the treatment of certain specific diseases of the respiratory system, such as pulmonary cystic fibrosis, usual interstitial pneumonia, allergic pneumonia, asbestosis, emphysema, pulmonary heart disease, pulmonary embolism, etc. A specific disease state that may be mentioned in idiopathic pulmonary fibrosis.

Idiopathic pulmonary fibrosis is a diffuse and fatal pulmonary interstitial disease with pathological features including alveolar epithelial damage, massive proliferation of lung fibroblasts, excessive deposition of extracellular matrix, ultimately leading to irreversible lung tissue damage. In the latter stages of the disease, subjects with idiopathic pulmonary fibrosis experience respiratory failure and death. It has been found that compounds of the invention may find utility in the treatment of idiopathic pulmonary fibrosis and/or alleviation of the symptoms associated with the disease.

Compounds of the invention are particularly useful in the treatment of the following lung and/or fibrotic conditions (whether otherwise mentioned herein or not): lung fibrosis, renal fibrosis, liver fibrosis, silicosis, acute bronchitis, chronic bronchitis, tracheobronchitis, bronchial asthma, status asthmatics, bronchiectasis, upper respiratory tract infections, including the common cold and influenza), allergic airway inflammation, bacterial pneumonia, viral pneumonia, mycoplasma pneumonia, reckettsia, radiaton pneumonia, pneumococcal (including staphylococcal, streptococcal and gram-negative bacillus) pneumonia, pulmonary candidiasis (including aspergillosis, mucormycosis, histoplasmosis, actinomycosis and nocardiosis), pulmonary mycosis, cryptococcosis, lung abscesses, anaphylactic pneumonia (Leoffer's syndrome), extrinsic allergic alveolitis, pulmonary eosinophia (eosinophilosis), obstructive pulmonary emphysema, pulmonary edema, pulmonary tuberculosis, respiratory alkalosis (acidosis), acute lung injury, interstitial lung disease, empyema, lung fibroma and cor pulmonale.

Particular mucosal disorders and disease in which compounds of the invention find utility include anorectal diseases, such as diarrhea, hemorrhoids, abscesses, fistula, fissures, anal itching, anal sinusitis, warts and rectal prolapse; inflammatory bowel disease, including Crohn's disease and, particularly, ulcerative colitis; gynaecological diseases, such as cervicitis, vaginitis, pelvic pain and disorders; and dental diseases, such as paradentitis, for example.

Compounds of the invention may further possess an antioxidation effect, by increasing SOD (superoxide dismutase) production and reducing lipid oxidation. Compounds of the invention may therefore be considered have antioxidant properties.

Compounds of the invention may also possess antipyretic properties that allow for the treatment of a fever and/or alleviate the symptoms thereof; for example, by reducing a subject's body temperature, which results in a reduction of fever. Compounds of the invention and formulations including them may therefore be considered to be antipyretics.

According to a further aspect of the invention there is provided a method of treatment of inflammation, of an inflammatory disorder, and/or of a disorder/condition characterised by inflammation (for example as a symptom), which method comprises the administration of a compound of the invention to a patient in need of such treatment.

For the avoidance of doubt, in the context of the present invention, the terms "treatment", "therapy" and "therapy method" include the therapeutic, or palliative, treatment of patients in need of, as well as the prophylactic treatment and/or diagnosis of patients which are susceptible to, inflammation and/or inflammatory disorders.

Compounds of the invention may further possess antiviral properties that may allow for the treatment of a viral infection per se, that is treatment of a viral infection, or a viral disease, by interfering with the replication of the virus within a host, as opposed to the treatment of any symptoms of any viral infection or disease, such as pain and/or inflammation. Such antiviral properties may also allow for the prevention of the onset of such an infection or disease, the protection of cells in a host from (e.g. further) viral infection, prevention or arrest of the spread of viral infection or disease (within a single host, or from one host to a new host), or for the prevention of reactivation of a virus after latency in a host.

According to a further aspect of the invention there is provided a method of treatment of a viral infection, which method comprises the administration of a compound of the invention or a salt thereof to a patient in need of such treatment.

Viral infections that may be mentioned include those caused by viruses in the following families: adenoviridae (e.g. adenovirus), papillomaviridae (e.g. human papillomavirus), polyomaviridae (e.g. BK virus; JC virus), herpesviridae (e.g. herpes simplex, type 1; herpes simplex, type 2; varicella-zoster virus; Epstein-Barr virus; human cytomegalovirus; human herpes virus, type 8), poxviridae (e.g. smallpox), hepadnaviridae (e.g. hepatitis B virus), parvoviridae (e.g. parvovirus B19), astroviridae (e.g. human astrovirus), caliciviridae (e.g. norovirus; Norwalk virus), picornaviridae (e.g. coxsackievirus, hepatitis A virus; poliovirus; rhinovirus), coronoviridae (e.g. severe acute respiratory syndrome virus), flaviviridae (e.g. hepatitis C virus; yellow fever virus; dengue virus; West Nile virus; tick-borne encephalitis virus), retroviridae (e.g. human immunodeficiency virus; HIV), togaviridae (e.g. rubella virus), arenaviridae (e.g. Lassa virus), bunyaviridae (e.g. hantavirus; Crimean-Congo hemorrhagic fever virus; Hantaan virus), filoviridae (e.g. Ebola virus; Marburg virus; Ravn virus), orthomyxoviridae (e.g. influenza viruses, including influenza A virus (e.g. H1N1 and H3N2 viruses), influenza B virus or influenza C virus), paramyxoviridae (e.g. measles virus; mumps virus; parainfluenza virus, respiratory syncytial virus), rhabdoviridae (e.g. rabies virus), hepeviridae (e.g. hepatitis E virus), reoviridae (e.g. rotavirus; orbivirus; coltivirus; Banna virus), as well as viruses not assigned to families, such as hepatitis D virus.

Viruses that may be more specifically mentioned include herpes simplex, type 1 and herpes simplex, type 2 viruses, human papillomavirus, influenza virus and parainfluenza virus.

Compounds of the invention may further possess antibacterial and/or bacteriostatic properties that may allow for the treatment of a bacterial infection per se, that is treatment of a bacterial infection, or a bacterial disease, by interfering with bacterial growth or proliferation in a host, as opposed to the treatment of any symptoms of any bacterial infection or disease, such as pain and/or inflammation. Compounds of the invention may therefore be considered to be bacteriocides and/or, preferably, bacteriostatic agents.

Such antibacterial properties may also allow for the prevention of the onset of such an infection or disease, the protection of cells in a host from (e.g. further) bacterial infection, prevention or arrest of the spread of bacterial infection or disease (within a single host, or from one host to a new host), or for the prevention of reactivation of a bacterium after latency in a host.

According to a further aspect of the invention there is provided a method of treatment of a bacterial infection, which method comprises the administration of a compound of the invention or a salt thereof to a patient in need of such treatment.

As disclosed herein, compounds of the invention may further possess anticancer properties that may allow for the treatment of a cancer per se, that is treatment of a cancer by interfering with the cancer as opposed to the treatment of any symptoms of the cancer, such as pain and/or inflammation. Such anticancer properties may also include the prevention of the onset of such a disease e.g. by treating inflammation and thereby preventing such onset.

According to another aspect of the invention, there is provided a method of treatment of cancer, which method comprises the administration of a compound of the invention or a salt thereof to a patient in need of such treatment.

Particular cancers that may be mentioned include oral cancer, a nasopharynx cancer, a middle ear cancer, a conjunctival cancer, a throat cancer, a tracheal cancer, an esophageal cancer, a gastric cancer, an intestinal cancer, a cervical cancer, an endometrial cancer, skin cancer and the like caused by oral mucositis, rhinitis, otitis media, conjunctivitis, pharyngitis, laryngitis, tracheitis, esophagitis, gastritis, enterocolitis, cervicitis, endometritis, erythema-like skin lesions and the like. A particular skin cancer that may be mentioned is basal cell carcinoma.

"Patients" include reptilian, avian and, preferably, mammalian (particularly human) patients.

In accordance with the invention, compounds of the invention are preferably administered locally or systemically, for example orally, intravenously or intraarterially (including by intravascular and other perivascular devices/dosage forms (e.g. stents)), intramuscularly, cutaneously, subcutaneously, transmucosally (e.g. sublingually or buccally), rectally, intravaginally, transdermally, nasally, pulmonarily (e.g. tracheally or bronchially), preferably topically, or by any other parenteral route, in the form of a pharmaceutical preparation comprising the compound(s) in pharmaceutically acceptable dosage form(s).

Administration by inhalation (e.g. nasally) is particularly useful when the condition to be treated is rhinitis or inflammation resulting from viral infections of the airways (e.g. upper respiratory tract infections such as the common cold and influenza).

Pulmonary administration is particularly useful when the condition to be treated is COPD or IPF. Topical forms of administration may be enhanced by creating a spray comprising active ingredients, e.g. by using a powder aerosol or by way of an aqueous mist using an appropriate atomisation technique or apparatus, such as a nebulizer.

Anorectal administration is particularly useful when the condition to be treated is hemorrhoids or ulcerative colitis, using an appropriate delivery means, such as a solution of foam to be injected or a suppository.

Administration to the lower gastrointestinal tract may also be achieved by parenteral, and particularly by peroral, delivery, by means of standard delayed- or extended-release coating techniques known to those skilled in the art. In particular, distinct parts of the upper or lower intestine may be targeted. For example, colonic administration can also be achieved by way of colon-targeted drug delivery means that are initially administered perorally or parenterally.

Preferred modes of delivery of compounds of the invention include topically to the site of inflammation (e.g. the mucosa, including the oral and/or nasal mucosa, the lung, the anorectal area and/or the colon) or, more preferably, the skin) in an appropriate (for example pharmaceutically- and topically-acceptable) vehicle suitable for application to the skin and/or the appropriate mucosal surface, and/or a commercially-available formulation, but may also include oral, intravenous, cutaneous or subcutaneous, nasal, intramuscular, intraperitoneal, or pulmonary delivery.

Compounds of the invention will generally be administered in the form of one or more for example pharmaceutical formulations in admixture with a (e.g. pharmaceutically acceptable) adjuvant, diluent or carrier, which may be selected with due regard to the intended route of administration (e.g. topical to the relevant mucosa (including the lung) or, preferably, the skin) and standard pharmaceutical or other (e.g. cosmetic) practice. Such pharmaceutically acceptable carriers may be chemically inert to the active compounds and may have no detrimental side effects or toxicity under the conditions of use. Such pharmaceutically acceptable carriers may also impart an immediate, or a modified, release of the active ingredient.

Suitable pharmaceutical formulations may be commercially available or otherwise prepared according to techniques that are described in the literature, for example, Remington *The Science and Practice of Pharmacy*, 22$^{nd}$ edition, Pharmaceutical Press (2012) and *Martindale—The Complete Drug Reference*, 38$^{th}$ Edition, Pharmaceutical Press (2014) and the documents referred to therein, the relevant disclosures in all of which documents are hereby incorporated by reference. Otherwise, the preparation of suitable formulations including compounds of the invention may be achieved non-inventively by the skilled person using routine techniques.

Compounds of the invention may be in the form of an aqueous formulation such as an emulsion, a suspension and/or a solution (e.g. an (optionally) buffered aqueous formulation (e.g. solution), such as a physiological saline-containing formulation (e.g. solution), a phosphate-containing formulation (e.g. solution), an acetate-containing formulation (e.g. solution) or a borate-containing formulation (e.g. solution), or a freeze-dried powder.

Active ingredient may further and/or in the alternative be combined with appropriate excipients to prepare:

gel formulations (for which suitable gel matrix materials include cellulose derivatives, carbomer and alginates, gummi tragacanthae, gelatin, pectin, carrageenan, gellan gum, starch, Xanthan gum, cationic guar gum, agar, noncellulosic polysaccharides, saccharides such as glucose, glycerin, propanediol, vinyl polymers, acrylic resins, polyvinyl alcohol, carboxyvinyl polymer and, particularly, hyaluronic acid);

lotions (for which suitable matrix materials include cellulose derivatives, glycerin, noncellulosic polysaccharides, polyethylene glycols of different molecular weights and propanediol);

pastes or ointments (for which suitable paste matrix materials include glycerin, vaseline, paraffin, polyethylene glycols of different molecular weights, etc.);

creams or foams (for which suitable excipients (e.g. foaming agents) include hydroxypropyl methyl cellulose, gelatin, polyethylene glycols of different molecular weights, sodium dodecyl sulfate, sodium fatty alcohol polyoxyethylene ether sulfonate, corn gluten powder and acrylamide);

powder aerosols (for which suitable excipients include mannitol, glycine, dextrin, dextrose, sucrose, lactose, sorbitol and polysorbates, e.g. a dry powder inhalant); and/or liquid, for example, water (aerosol) sprays for oral use or for inhalation (for which suitable excipients include viscosity modifiers, such as hyaluronic acid, sugars, such as glucose and lactose, emulsifiers, buffering agents, alcohols, water, preservatives, sweeteners, flavours, etc.);

injectable solutions or suspensions (which may be aqueous or otherwise and for which suitable excipients include solvents and co-solvents, solubilizing agents, wetting agents, suspending agents, emulsifying agents, thickening agents, chelating agents, antioxidants, reducing agents, antimicrobial preservatives, buffers and/or pH modifiers, bulking agents, protectants and tonicity-modifying agents).

Moisturizing agents, such as glycerol, glycerin, polyethylene glycol, trehalose, glycerol, petrolatum, paraffin oil, silicone oil, hyaluronic acid and salts (e.g. sodium and potassium salts) thereof, octanoic/caprylic triglyceride, and the like; and/or antioxidants, such as vitamins and glutathione; and/or pH modifiers, such as acids, bases and pH buffers, may also be included in such formulations, as appropriate. Furthermore, surfactants/emulsifiers, such as hexadecanol (cetyl alcohol), fatty acids (e.g. stearic acid), sodium dodecyl sulfate (sodium lauryl sulfate), sorbitan esters (e.g. sorbitan stearate, sorbitan oleate, etc.), monoacyl glycerides (such as glyceryl monostearate) polyethoxylated alcohols, polyvinyl alcohols, polyol esters, polyoxyethylene alkyl ethers (e.g. polyoxyethylene sorbitan monooleate), polyoxyethylene castor oil derivatives, ethoxylated fatty acid esters, polyoxylglycerides, lauryl dimethyl amine oxide, bile salts (e.g. sodium deoxycholate, sodium cholate), phospholipids, N,N-dimethyldodecylamine-N-oxide, hexadecyltrimethyl-ammonium bromide, poloxamers, lecithin, sterols (e.g. cholesterol), sugar esters, polysorbates, and the like; preservatives, such as phenoxyethanol, ethylhexyl glycerin, and the like; and thickeners, such as acryloyldimethyltaurate/VP copolymer, may be included. In particular stearic acid, glyceryl monostearate, hexadecanol, sorbitan stearate, cetyl alcohol, octanoic/capric glyceride etc. may be included, particularly in cream formulations.

Compounds of the invention, and (e.g. pharmaceutical) formulations (e.g. aqueous solutions, gels, creams, ointments, lotions, foams, pastes and/or dry powders as described above) including them, may further be combined with an appropriate matrix material to prepare a dressing or a therapeutic patch for application on a biological surface, such as the skin or a mucosal surface. Such formulations may thus be employed to impregnate a matrix material, such as gauze, non-woven cloth or silk paper. The therapeutic patch may alternatively be, for example, a band-aid, a facial mask, an eye mask, a hand mask, a foot mask, etc.

Vaseline may be employed for use in applying such dressings to wounds, but we have also found that ointments based on PEGs (e.g. PEG 400) may be combined with matrix materials to prepare dressings without the need to use vaseline.

Compounds of the invention may be administered for inhalation by way of suspension, a dry powder or a solution. Suitable inhalation devices include pressurized metered-dose inhalers (pMDIs), which may be hand- or breath-actuated and employed with or without a standard spacer device), dry powder inhalers (DPIs), which may be single-dose, multi-dose, and power-assisted, and soft mist inhalers (SMIs) or nebulizers, in which aerosol drug in a fine mist is delivered with slower velocity than a spray delivered using, for example, a pMDI.

In pMDIs, compounds of the invention may be administered as a pressurized suspension of micronized particles distributed in a propellant (e.g. HFA, along with excipients, such as mannitol, lactose, sorbitol, etc.), or as an ethanolic solutions, to deliver one or more metered dose of between about 20 and about 100 μL with each actuation. Actuation may be effected by hand (e.g pressing) or by inhalation (breath-actuation), involving a flow-triggered system driven by a spring In DPIs, compounds of the invention may be administered in the form of micronized drug particles (of a size between about 1 and about 5 μm), either alone or blended with inactive excipient of larger particle size (e.g. mannitol), inside a capsule, which may be pre-loaded or manually loaded into the device. Inhalation from a DPI may de-aggregate the medication particles and disperse them within the airways.

In SMIs, compounds of the invention may be stored as a solution inside a cartridge, which is loaded into the device. A spring may release the dose into a micropump, such that the dose is released when button is pressed, releasing jet streams of drug solution.

Various nebulizers may also be used to administer compounds of the invention in the form of a fine mist of aerosolized solution. Nebulizers may include breath-enhanced jet nebulizer (in which, with the assistance of a compressor, an air stream moves through jet causing drug solution to be aerosolized); breath-actuated jet nebulizers (in which, after a patient inhales, with the assistance of a compressor, an air stream moves through tube causing drug solution to be aerosolized); ultrasonic nebulizers (in which piezoelectric crystals vibrate causing aerosolization by heating causing nebulization); vibrating mesh nebulizers (in which piezoelectric crystals vibrate a mesh plate causing aerosolization to give very fine droplets without a significant change in temperature of the solution during nebulization).

According to a further aspect of the invention there is provided a process for the preparation of a pharmaceutical composition/formulation, as defined herein, which process comprises bringing into association a compound of the invention, as hereinbefore defined, with one or more pharmaceutically-acceptable excipient, as hereinbefore defined.

Compounds of the invention may also be combined in treatment with one or more growth factors selected from platelet-type growth factors (including platelet-derived growth factors, PDGFs); osteosarcoma-derived growth factors (ODGF), epidermal growth factors (EGFs), transforming growth factors (TGFα and TGFβ), fibroblast growth factors (αFGF, βFGF), insulin-like growth factors (IGF-I, IGF-II), nerve growth factors (NGF), interleukin-type growth factors (IL-1, IL-1, IL-3), erythropoietin (EPO), and colony stimulating factor (CSF).

According to a further aspect of the invention there is provided a (e.g. pharmaceutical) composition comprising a compound of the invention and one or more pharmaceutically-acceptable excipient, such as an adjuvant, diluent or carrier. Preferred formulations are suitable for application locally to e.g. the mucosa (including the oral and/or nasal mucosa, the lung, the anorectal area and/or the colon) or, more preferably, the skin and therefore comprise a topically-acceptable adjuvant, diluent or carrier.

There is thus further provided pharmaceutical compositions comprising compounds of the invention that are suitable for, adapted for, and/or packaged and presented for topical administration (e.g. to the mucosa, including the oral and/or nasal mucosa, the lung, the anorectal area and/or the colon, or, preferably, to the skin), as well as the use of such a formulation in the treatment of a disorder including inflammation, an inflammatory disorder and/or a condition characterized by inflammation (e.g. as a symptom) by way of direct topical administration of that formulation (e.g. to the mucosa, including the oral and/or nasal mucosa, the lung, the anorectal area and/or the colon, or, preferably, to the skin).

In relation to this aspect of the invention, for the avoidance of doubt, topical formulations comprising compounds of the invention may be used in any and all conditions described herein, including treatments of inflammation, in the treatment of any and all inflammatory disorder(s), and/or in the treatment of any and all condition(s) characterized by inflammation, as hereinbefore mentioned, defined or described. Similarly, topical formulations comprising compounds of the invention that may be mentioned include any and all of those mentioned, defined or described herein. Any and all of the relevant disclosures herein are hereby incorporated by reference in conjunction with this aspect of the invention.

Topical (e.g. liquid- or (e.g. aqueous) solution-based) formulations comprising compounds of the invention may be particularly useful in wound recovery, and may alleviate pain (including aching) and, particularly, pruritis/itching that is associated with the wound itself and the wound healing process. Such topical formulations comprising compounds of the invention may be particularly useful in the prevention and/or suppression of the exudation of body fluids from wounds, particularly during the acute inflammation stage, for example during the first 48 hours, after a burn or wound has been inflicted. This prevents the risk of infection, and other physiological reactions. Such topical formulations comprising compounds of the invention may also be particularly useful in the prevention and/or suppression of scarring and melanin pigmentation (vide supra), whether associated with wounds or otherwise.

Administration of active ingredients may be continuous or intermittent. The mode of administration may also be determined by the timing and frequency of administration, but is also dependent, in the case of the therapeutic treatment of inflammation, on the severity of the condition.

Depending on the disorder, and the patient, to be treated, as well as the route of administration, compounds of the invention may be administered at varying therapeutically effective doses to a patient in need thereof.

Similarly, the amount of active ingredient in a formulation will depend on the severity of the condition, and on the patient, to be treated, but may be determined by the skilled person.

In any event, the medical practitioner, or other skilled person, will be able to determine routinely the actual dosage, which will be most suitable for an individual patient, depending on the severity of the condition and route of administration. The dosages mentioned herein are exemplary of the average case; there can, of course, be individual instances where higher or lower dosage ranges are merited, and such are within the scope of this invention.

Doses may be administered between once and four (e.g. three) times daily.

Appropriate concentrations of compounds of the invention in an aqueous solution product may be about 0.01 (e.g. about 0.1) to about 15.0 mg/mL, in all cases calculated as the free (non-salt) compound.

Appropriate topical doses of compounds of the invention are in the range of about 0.05 to about 50 µg/cm$^2$ of treated area, such as about 0.1 (e.g. about 0.5) to about 20 µg/cm$^2$ of treated area, including about 1 to about 10 µg/cm$^2$) of treated area, such as about 5 µg/cm$^2$ of treated area, in all cases calculated as the free (non-salt) compound.

Appropriate doses of compounds of the invention for nasal administration (e.g. by inhalation) are in the range of about 0.01 µg to about 2000 mg, for example between about 0.1 µg to about 500 mg, or between 1 µg to about 100 mg. Particular doses for nasal administration that may be mentioned include between about 10 µg to about 1 mg, particularly a dose of about 0.1 mg (i.e. about 100 µg). Nasal administration of about 0.1 mg per day of compounds of the invention has been found to be particularly effective in the treatment of conditions associated with inflammation of the nasal passages and mucosae, such as rhinitis (e.g. allergic rhinitis).

Appropriate doses of compounds of the invention for pulmonary administration (e.g. by inhalation) are in the range of about 0.01 µg to about 2000 mg, for example between about 0.1 µg to about 500 mg, or between 1 µg to about 100 mg. Particular doses for pulmonary administration that may be mentioned include between about 10 µg to about 10 mg, particularly a dose of about 0.6 mg (i.e. 60 µg) to 6 mg (e.g. for use in treating COPD or idiopathic pulmonary fibrosis).

We prefer that pH values of formulations comprising compounds of the invention are in the range of about 1.0 to about 9.0 (for example about 3.0 to about 8.0).

In any event, the dose administered to a mammal, particularly a human, in the context of the present invention should be sufficient to effect a therapeutic response in the mammal over a reasonable timeframe (as described hereinbefore). One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease, as well as genetic differences between patients.

In the uses and methods described herein, compounds of the invention may also be combined with one or more active ingredients that are useful in the treatment of inflammation and/or inflammatory disorders (other antiinflammatory agents). Such patients may thus also (and/or already) be receiving therapy based upon administration of one or more of such other active ingredients, by which we mean receiving a prescribed dose of one or more of those active ingredients mentioned herein, prior to, in addition to, and/or following, treatment with a compound of the invention.

Such anti-inflammatory agents that may be used in combination with compounds of the invention in the treatment of inflammation include therapeutic agents that are useful in the treatment of inflammation and/or of diseases characterised by inflammation as one of its symptoms. Depending on the condition to be treated, such antiinflammatory agents may include NSAIDs, leukotriene receptor antagonists (e.g. montelukast itself), corticosteroids, analgesics and certain enzymes, such as trypsin, for example as described hereinafter. Compounds of the invention may also be combined with leukotriene B4 (LTB4).

In this context, compounds of the invention may also be combined for use in the treatment of inflammation with one or more mussel adhesive proteins (MAPs), which includes any adhesive protein that may be derived from mussel species, such as *Mytilus edulis* (blue mussel), including full length proteins, including all sub-types, that are or may be derived from mussels, such as the collagens pre-COL-P, pre-COL-D and pre-COL-NG, the mussel feet matrix proteins PTMP and DTMP, and, more preferably, mfps or mefps, such as mefp-2, mefp-3, mefp-4, mefp-5, mefp-6 and especially mefp-1, and includes mixtures or combinations of any of these proteins, such as mefps. Naturally-occurring MAPs may be prepared, for example by mixed adsorption chromatography (see Chinese Patent No. ZL200710179491.0), by carboxymethyl ion exchange chromatography (see Chinese Patent No. ZL200710179492.5), and/or by salting out and dialysis (Chinese Patent No. ZL200910087567.6). Commercial sources of MAPs include USUN Bio Co. (China; sold as MAP Medical Device®), BD Biosciences (USA), Kollodis (South Korea) and Biopolymer (Sweden). MAPs may alternatively be produced using known recombinant DNA methods.

Derivatives (e.g. pharmaceutically-acceptable derivatives) of MAPs may also be combined with compounds of the invention and include compounds with, for example, molecular weights in the range of about 500 Da to about 2,000 Da (e.g. about 1,500, such as about 1,200, including about 800 Da). Such derivatives may also include other compounds that comprise amino acid sequences that are the same as, or are (e.g. minor) variants (as hereinbefore defined) of, sequences that have been identified in naturally-occurring MAPs, and which may be synthesized by chemical and/or biological processes (e.g. chemical modifications of naturally-occurring MAPs, or direct synthesis).

For example, as discussed hereinbefore, the isolated decapeptide compounds of the sequences:

Ala-Lys-Pro-Ser-Tyr-Hyp-
    Hyp-Thr-DOPA-Lys    (mefp-1 decapeptide, SEQ ID No: 4); and Ala-Lys-Pro-Ser-Tyr-Hyp-Hyp-Thr-Tyr-Lys    (SEQ ID No: 12)

are pharmaceutically-acceptable low molecular weight derivatives of MAP that may be combined with a compound of the invention.

Other preferred agents that may be combined with compounds of the invention include LTB4 (to treat wounds and burns), montelukast (to treat inflammation generally) and trypsin (to treat inflammation of the mucosa associated with e.g. viral infections).

Compounds of the invention may also be combined with other therapeutic agents which, when administered, are known to give rise to inflammation as a side-effect.

When compounds of the invention may be "combined" with other therapeutic agents in this way, the active ingredients may be administered together in the same formulation, or administered separately (simultaneously or sequentially) in different formulations.

Such combination products provide for the administration of compounds of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention; another antiinflammatory agent, or agent known to give rise to inflammation as a side-effect; and a pharmaceutically-acceptable excipient (e.g. adjuvant, diluent or carrier), which formulation is hereinafter referred to as a "combined preparation"; and
(2) a kit of parts comprising components:
(A) a pharmaceutical formulation including a compound of the invention in admixture with a pharmaceutically-acceptable adjuvant, diluent or carrier; and
(B) a pharmaceutical formulation including another antiinflammatory agent, or agent known to give rise to inflammation as a side-effect, in admixture with a pharmaceutically-acceptable adjuvant, diluent or carrier,
which components (A) and (B) are each provided in a form that is suitable for administration in conjunction with the other.

In a further aspect of the invention, there is provided a process for the preparation of a combined preparation as hereinbefore defined, which process comprises bringing into association a compound of the invention, the other antiinflammatory agent, or agent known to give rise to inflammation as a side-effect, and at least one (e.g. pharmaceutically-acceptable) excipient.

In a further aspect of the invention, there is provided a process for the preparation of a kit-of-parts as hereinbefore defined, which process comprises bringing into association components (A) and (B). As used herein, references to bringing into association will mean that the two components are rendered suitable for administration in conjunction with each other.

Thus, in relation to the process for the preparation of a kit-of-parts as hereinbefore defined, by bringing the two components "into association with" each other, we include that the two components of the kit-of-parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(I) one of components (A) and (B) as defined herein; together with
(II) instructions to use that component in conjunction with the other of the two components.

The kits of parts described herein may comprise more than one formulation including an appropriate quantity/dose of a compound of the invention, and/or more than one formulation including an appropriate quantity/dose of another antiinflammatory agent, in order to provide for repeat dosing. If more than one formulation (comprising either active compound) is present, such formulations may be the same, or may be different in terms of the dose of either compound, chemical composition(s) and/or physical form(s).

With respect to the kits of parts as described herein, by "administration in conjunction with", we include that respective formulations comprising a compound of the invention and other antiinflammatory agent are administered, sequentially, separately and/or simultaneously, over the course of treatment of the relevant condition.

Thus, in respect of the combination product according to the invention, the term "administration in conjunction with" includes that the two components of the combination product (compound of the invention and other antiinflammatory agent) are administered (optionally repeatedly), either together, or sufficiently closely in time, to enable a beneficial effect for the patient, that is greater, over the course of the treatment of the relevant condition, than if either a formulation comprising compound of the invention, or a formulation comprising the other agent, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to the invention, the term "in conjunction with" includes that one or other of the two formulations may be administered (optionally repeatedly) prior to, after, and/or at the same time as, administration of the other component. When used in this context, the terms "administered simultaneously" and "administered at the same time as" include that individual doses of the relevant compound of the invention and other antiinflammatory agent are administered within 48 hours (e.g. 24 hours) of each other.

Wherever the word "about" is employed herein, for example in the context of amounts, such as concentrations and/or doses of active ingredients, molecular weights or pHs, it will be appreciated that such variables are approximate and as such may vary by ±10%, for example ±5% and preferably ±2% (e.g. ±1%) from the numbers specified herein. In this respect, the term "about 10%" means e.g. ±10% about the number 10, i.e. between 9% and 11%.

Compounds of the invention have the advantage that they may be used in variety of conditions characterised by inflammation, whether that condition is an organic inflammatory disease per se or is associated with, or is characterised by, inflammation (e.g. a wound, a burn or a viral infection).

The uses and methods described herein may also have the advantage that, in the treatment of the conditions mentioned hereinbefore, they may be more convenient for the physician and/or patient than, be more efficacious than, be less toxic than, have a broader range of activity than, be more potent than, produce fewer side effects than, or that it/they may have other useful pharmacological properties over, similar compounds or methods (treatments) known in the prior art, whether for use in the treatment of inflammation, inflammatory disorders, or disorders characterised by inflammation as a symptom (including wounds), or otherwise.

The invention is illustrated by the following examples, in which, for various compounds, including compounds of the invention, FIG. 1 shows the swelling rates in a mouse ear swelling model;

Figure 1:
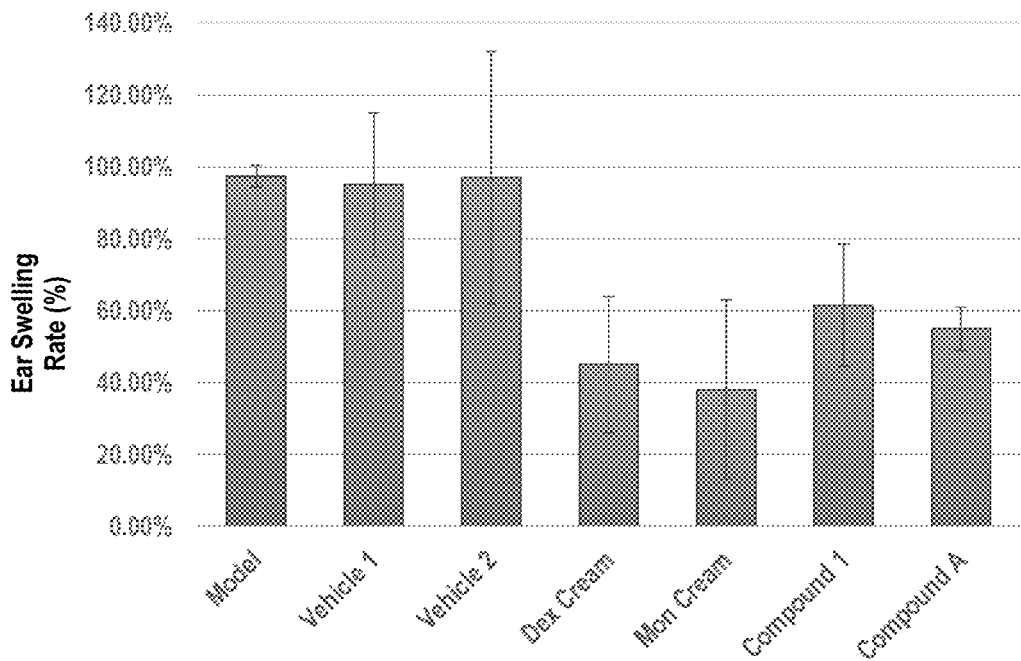
Figure 13:
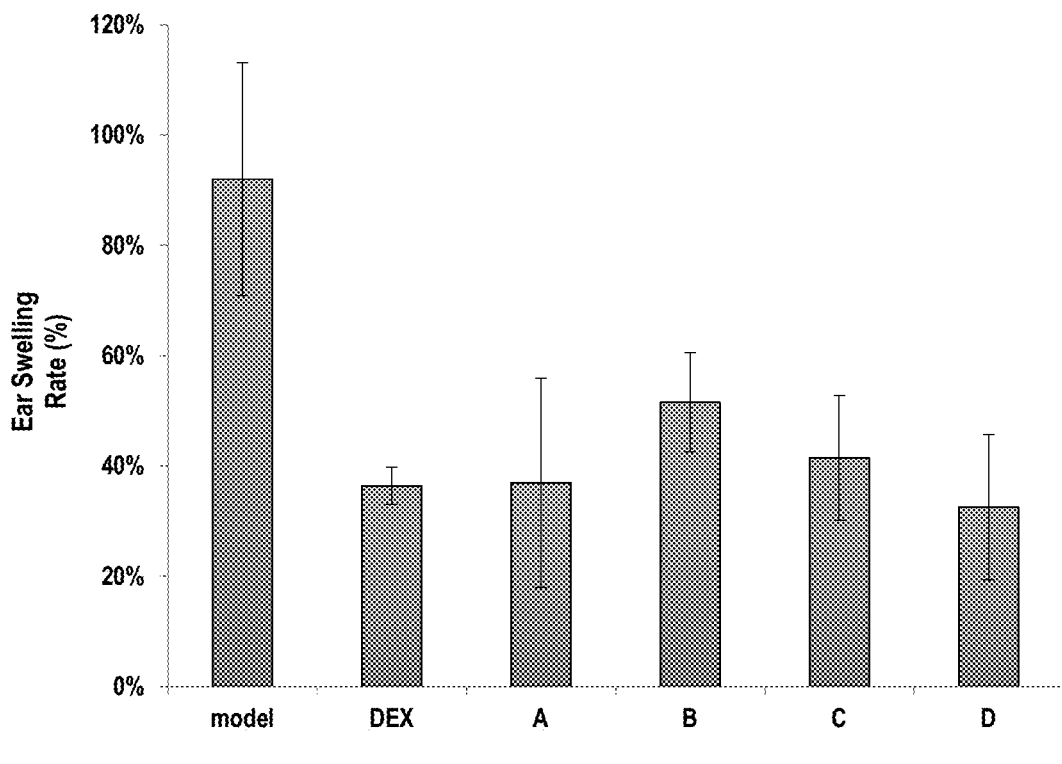
Figure 14:
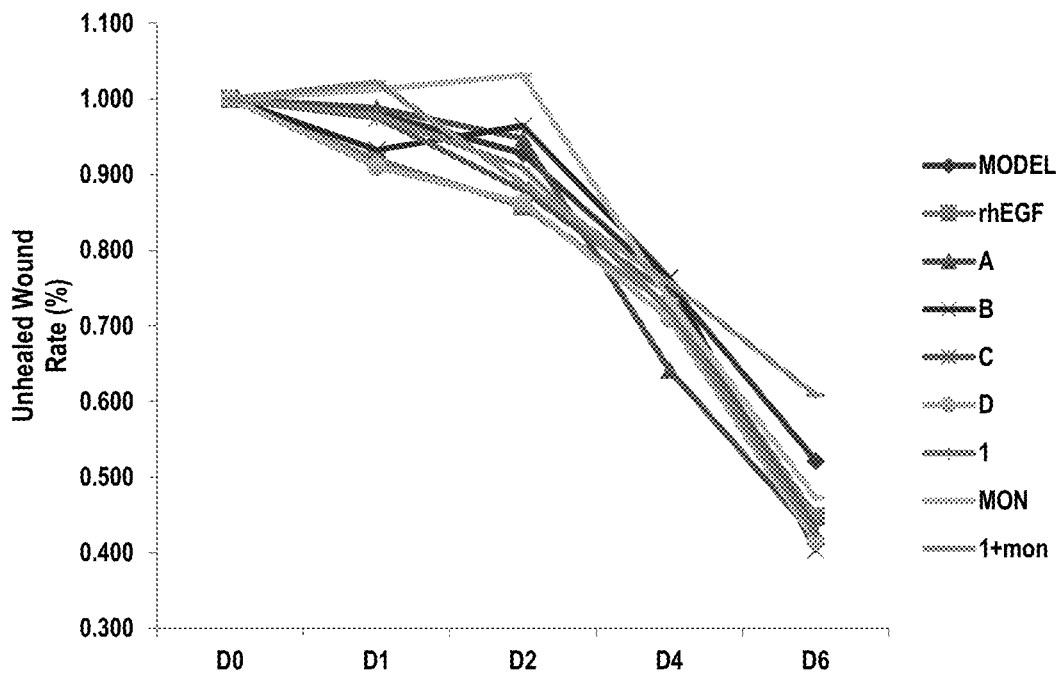
Figure 15:
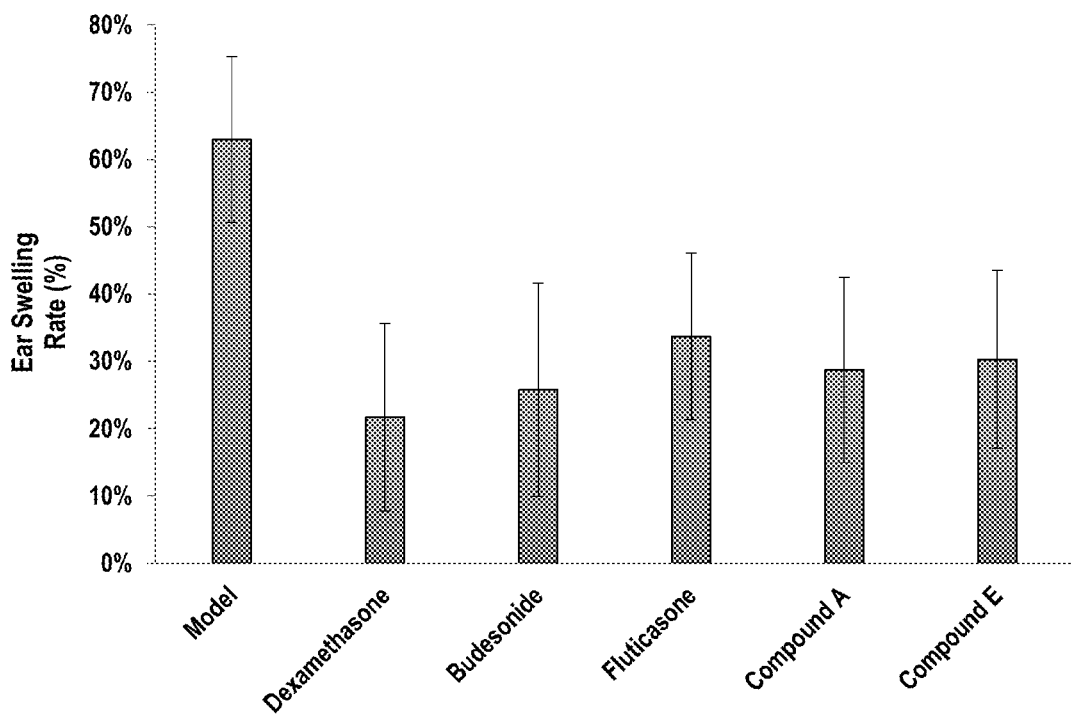
Figure 16:
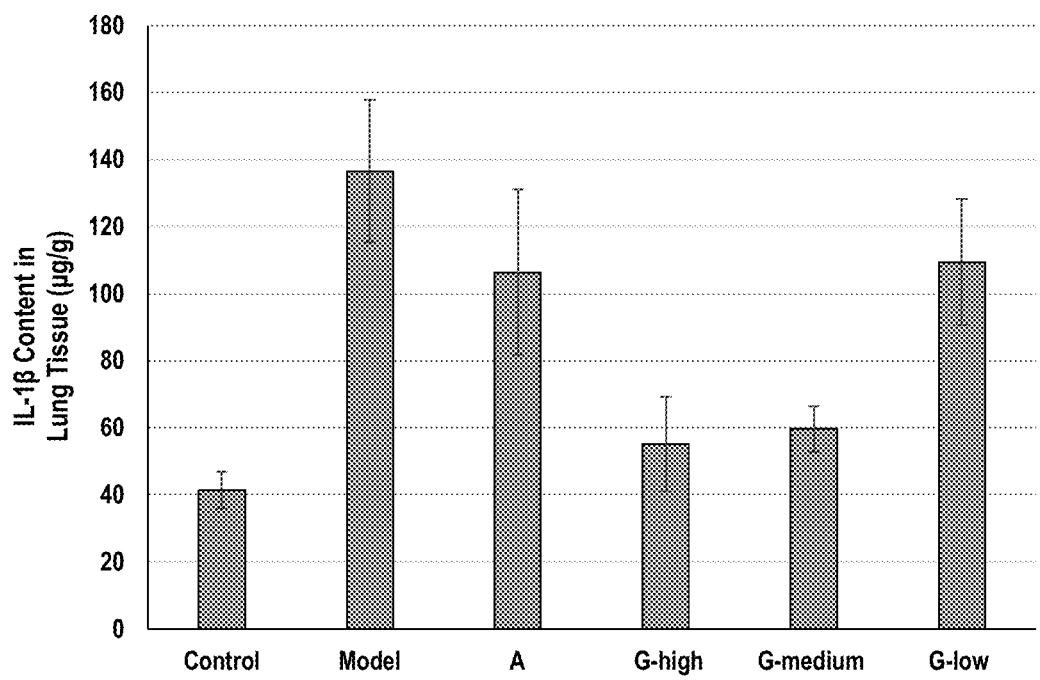
Figure 17:
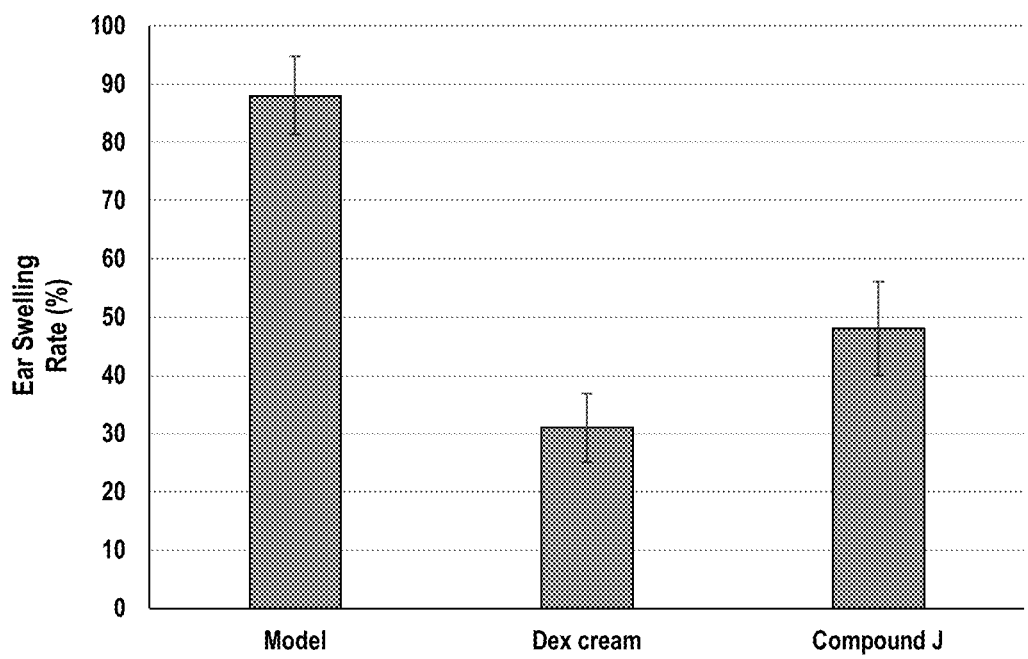

FIGS. 13 and 17 both show the effect of compounds of the invention on edema caused by acute inflammation in a further mouse ear swelling models;

FIG. 14 shows the unhealed wound rate in a further acute wound mouse model;

FIG. 15 shows a comparison between compounds of the invention and known antiinflammatory steroids in a mouse ear swelling model; and FIG. 16 shows FIG. 1 IL-1β content in lung tissues for different compounds of the invention in a mouse lung injury model.

EXAMPLES

Example 1

Synthesis of Montelukast Styrene-Ala-Lys-Pro-Ser-Tyr-Hyp-Hyp-Thr-Tyr-Lys (i.e. Montelukast Styrene Covalently Bonded to Amino Acid SEQ ID No: 12 at the N-Terminus)

To synthesise 3 mmol of peptide SEQ ID No: 12, the following procedure was followed.

Fmoc-Lys-Boc-Wang resin (9.15 g, GLS180322-41301, GL Biochem, Shanghai, China) was loaded into a glass reaction column.

Methylene chloride (DCM, 200 mL; Shandong Jinling Chemical Industry Co Ltd, Shandong, China) was added to the column and allowed to soak the resin for about half an hour. The DCM was then removed by vacuum filtration.

The resin was washed 3 times with N,N-dimethylformamide (DMF, 200 mL; Shandong Shitaifeng Fertilizer Industry Co Ltd, Shandong, China).

A 20% piperidine solution in DMF (200 mL; Shandong Shitaifeng Fertilizer Industry Co Ltd, Shandong, China) and was added as deprotection solution and reacted for 20 minutes. The solution was then removed by vacuum filtration and the column was washed with DMF six times.

Fmoc-Tyr(tBu)-OH (4.14 g; GLS170916-36901, GL Biochem, Shanghai, China) and 2-(1H-benzotriazole-1-yl)-1,1,3,3-tetramethylaminium tetrafluoroborate (TBTU, 2.89 g; GLS170805-00705, GL Biochem, Shanghai, China) were added to the resin. DMF (150 mL) was added to the reaction column, followed by N,N-diisopropylethylamine (DIPEA, 2.33 g; Suzhou Highfine Biotech Co. Ltd, Jiangsu, China). A colour reaction was detected in the resin after 30 minutes, indicating the reaction was complete. The solvent was removed by vacuum filtration.

The above coupling steps were repeated to couple the remaining amino acids in the same amounts (by mols): Fmoc-Thr(tBu)-OH, Fmoc-4-Hyp(tBu)-OH, Fmoc-4-Hyp (tBu)-OH, Fmoc-Tyr(tBu)-OH, Fmoc-Ser(tBu)-OH, Fmoc-Pro-OH, Fmoc-Lys(Boc)-OH and Fmoc-Ala-OH.

Finally, montelukast (5.47 g; MedChemExpress, MCE China, Shanghai, China) was added to the resin. The liquid was then drained after 15 minutes and the column washed with DMF, DCM and methanol, 3 times each, respectively.

91.5 mL (i.e. 10 mL per gram of resin) of lysate, which was comprised of 95% trifluoroacetic acid (TFA), 2.5% water and 2.5% triisopropylsilane (Tis), was added to immerse the resin-bounded peptide-containing compound. The side chains were also deprotected during cleavage. After cleavage the solid support was removed by filtration and the filtrate was concentrated under reduced pressure. The cleaved peptide was precipitated with diethyl ether and lyophilized to yield 600 mg of crude title compound.

1 mg of crude product was dissolved in 1 mL of an acetonitrile and water mixture (1:3) and detected using a P3000A HPLC pump and LC3000 semi-preparation equipment (preparation column model: GS-120-10-C18-AP 30 mm; Beijing Chuangxintongheng Science & Technology Co., Ltd., Beijing, China). The appropriate gradient for elution was calculated and the target peak was detected at 11.035 with LCMS (analysis column model: GS-120-5-C18-BIO, 4.6*250 mm; detection: UV at 220 nm; solvent A: 0.1% TFA in MeCN, solvent B: 0.1% TFA in water; flow rate 1.0 mL/min.; volume: 10 μL).

The crude compound was desalted using an anion exchange resin, analysed and freeze-dried. Approximately 50 mg of purified peptide was obtained after purification, which was re-tested for confirmation.

MS: m/z 866.90 $[M+2H]^{2+}$.

Based on the characterising data available and presented herein, it is understood that the compound prepared by way of this example is that identified above as the title compound. Otherwise, the compound that is prepared in Example 1 is a compound of the invention in which, in the compound of formula I, n is 0 and the compound of formula I is covalently bonded to amino acid SEQ ID No: 12 at the N-terminus. In any event, the compound of Example 1 is referred to hereinafter as "Compound A".

Example 2

Synthesis of Ala-Lys-Pro-Ser-Tyr-Hyp-Hyp-Thr-DOPA-Lys (Montelukast Styrene) (i.e. Montelukast Styrene Covalently Bonded to Amino Acid SEQ ID No: 4 on the C-Terminus A similar procedure to that described in Example 1 above was employed starting with Fmoc-Lys(Dde)-OH (CAS No.: 150629-67-7) on a Wang resin.

A 25% piperidine solution in DMF (200 mL; Shandong Shitaifeng Fertilizer Industry Co Ltd, Shandong, China) was added to remove the protective Fmoc group.

The second protected amino acid Fmoc-DOPA(acetonide)-OH was added, along with TBTU and DIPEA, until the reaction was completed.

The above coupling steps were repeated to couple the remaining amino acids in the same amounts (by mols): Fmoc-Thr(tBu)-OH, Fmoc-4-Hyp(tBu)-OH, Fmoc-4-Hyp(tBu)-OH, Fmoc-Tyr(tBu)-OH, Fmoc-Ser(tBu)-OH, Fmoc-Pro-OH, Fmoc-Lys(Boc)-OH and Fmoc-Ala-OH.

The peptidyl-resin was placed in a flask and treated with 2% hydrazine monohydrate in DMF (25 mL/g). The flask was stoppered, and mixture was left to stand at room temperature for 3 minutes. The resin was then washed with DMF. Montelukast (5.47 g; MedChemExpress, MCE China, Shanghai, China) was added to the resin, along with TBTU and DIPEA and the mixture was reacted for 1 hour.

The protected peptidyl-resin was treated with 91.5 mL of lysate (a mixture of 95% TFA, 2.5% water, and 2.5% Tis) for 1 hour. After cleavage the solid support was removed by filtration and the filtrate was concentrated under reduced pressure. The cleaved peptide was precipitated with diethyl ether and lyophilized to yield approximately 600 mg of crude title compound.

After purification, 50 mg of pure product was obtained.

MS: m/z 875.75 $[M+2H]^{2+}$.

Based on the characterising data available and presented herein it is understood that the compound prepared by way of this example is that identified above as the title compound. Otherwise, the compound that is prepared in Example 2 is a compound of the invention in which, in the compound of formula I, n is 0 and the compound of formula I is covalently bonded to amino acid SEQ ID No: 4 on the C-terminus Lys. In any event, the compound of Example 2 is referred to hereinafter as "Compound B".

Example 3

Synthesis of Montelukast Styrene-Ala-Lys-Pro-pSer-Tyr-Hyp-Hyp-Thr-Tyr-Lys (i.e. Montelukast Styrene Covalently Bonded to Amino Acid SEQ ID No: 13 at the N-Terminus)

A similar procedure to that described in Example 4 below was employed starting with Fmoc-Lys(Dde)-OH (CAS No.: 150629-67-7) on a Wang resin.

A 25% piperidine solution in DMF (200 mL; Shandong Shitaifeng Fertilizer Industry Co Ltd, Shandong, China) was added to remove the protective Fmoc group.

The second protected amino acid Fmoc-Tyr(tBu)-OH (GLS170916-36901, GL Biochem, Shanghai, China) was added, along with ByBOP and DIPEA, until the reaction was completed.

The above coupling steps were repeated to couple the remaining amino acids in the same amounts (by mols): Fmoc-Thr(tBu)-OH, Fmoc-4-Hyp(tBu)-OH, Fmoc-4-Hyp(tBu)-OH, Fmoc-Tyr(tBu)-OH, Fmoc-pSer(tBu)-OH, Fmoc-Pro-OH, Fmoc-Lys(Boc)-OH and Fmoc-Ala-OH.

The peptidyl-resin was placed in a flask and treated with 2% hydrazine monohydrate in DMF (25 mL/g). The flask was stoppered, and the mixture was left to stand at room temperature for 3 minutes. The resin was then washed with DMF. Montelukast (1.8 g;

MedChemExpress, MCE China, Shanghai, China) was added to the resin, along with TBTU and DIPEA and the mixture was reacted for 1 hour.

Lysate (10 mL per gram of resin), which was comprised of 95% trifluoroacetic acid (TFA), 2.5% water and 2.5% triisopropylsilane (Tis), was added to immerse the resin-bounded peptide-containing compound. The side chains were also deprotected during cleavage. After cleavage the solid support was removed by filtration and the filtrate was concentrated under reduced pressure. The cleaved peptide was precipitated with diethyl ether and lyophilized to yield 1.4 g of crude peptide.

1 mg of crude product was dissolved in 1 mL of an acetonitrile and water mixture (1:3) and detected using a P3000A HPLC pump and LC3000 semi-preparation equipment (preparation column model: GS-120-10-C18-AP 30 mm; Beijing Chuangxintongheng Science & Technology Co., Ltd., Beijing, China). The appropriate gradient for elution was calculated and the target peak was detected with LCMS (analysis column model: GS-120-5-C18-BIO, 4.6*250 mm).

The crude compound was desalted using an anion exchange resin, analysed and freeze-dried, which was re-tested for confirmation.

After purification, 98 mg of pure product was obtained (a yield rate of approximately 7% from the crude product).

MS: m/z 907.3 $[M+2H]^{2+}$.

Based on the characterising data available and presented herein it is understood that the compound prepared by way of this example is that identified above as the title compound. Otherwise, the compound that is prepared in Example 3 is a compound of the invention in which, in the compound of formula I, n is 0 and the compound of formula I is covalently bonded to amino acid SEQ ID No: 13 at the N-terminus. In any event, the compound of Example 3 is referred to hereinafter as "Compound C".

Example 4

Synthesis of Ala-Lys(montelukast styrene)-Pro-Ser-Tyr-Hyp-Hyp-Thr-Tyr-Lys(Montelukast Styrene) (i.e. Two Molecules of Montelukast Styrene Covalently Bonded Via the Lys Residues to Amino Acid SEQ ID No: 12)

To synthesise 1 mmol peptide SEQ ID No: 12, the following procedure was followed.

Fmoc-Lys(Dde)-OH (CAS No.: 150629-67-7) on a Wang resin (3 g, GL Biochem, Shanghai, China) was loaded into a glass reaction column.

Methylene chloride (DCM, 60 mL; Shandong Jinling Chemical Industry Co Ltd, Shandong, China) was added to the column and allowed to soak the resin for about half an hour. The DCM was then removed by vacuum filtration.

The resin was washed 3 times with N,N-dimethylformamide (DMF, 60 mL; Shandong Shitaifeng Fertilizer Industry Co Ltd, Shandong, China).

A 20% piperidine solution in DMF (30 mL; Shandong Shitaifeng Fertilizer Industry Co Ltd, Shandong, China) and was added as deprotection solution and reacted for 20 minutes. The solution was then removed by vacuum filtration and the column was washed with DMF six times.

Fmoc-Tyr(tBu)-OH (1.4 g; GLS170916-36901, GL Biochem, Shanghai, China) and benzotriazol-1-yloxy) tripyrrolidinophosphonium hexafluorophosphate (ByBOP, 1.56 g; Suzhou Highfine Biotech Co. Ltd, Jiangsu, China) were added to the resin, followed by DIPEA (1 mL; Suzhou Highfine Biotech Co. Ltd, Jiangsu, China). A colour reaction was detected in the resin after 30 minutes, indicating the reaction was complete. The solvent was removed by vacuum filtration.

The above coupling steps were repeated to couple the remaining amino acids in the same amounts (by mols): Fmoc-Thr(tBu)-OH, Fmoc-4-Hyp(tBu)-OH, Fmoc-4-Hyp (tBu)-OH, Fmoc-Tyr(tBu)-OH, Fmoc-Ser(tBu)-OH, Fmoc-Pro-OH, Fmoc-Lys(Dde)-OH and Boc-Ala-OH.

The peptidyl-resin was placed in a flask and treated with 2% hydrazine monohydrate in DMF (25 mL/g). The flask was stoppered, and the mixture was left to stand at room temperature for 3 minutes. The resin was then washed with DMF. Montelukast (3.6 g; MedChemExpress, MCE China, Shanghai, China) was added to the resin, along with TBTU and DIPEA and the mixture was reacted for 1 hour.

Lysate (30 mL; 10 mL per gram of resin), which was comprised of 95% trifluoroacetic acid (TFA), 2.5% water and 2.5% triisopropylsilane (Tis), was added to immerse the resin-bounded peptide-containing compound. The side chains were also deprotected during cleavage. After cleavage the solid support was removed by filtration and the filtrate was concentrated under reduced pressure. The cleaved peptide was precipitated with diethyl ether and lyophilized to yield 1.6 g of crude peptide.

1 mg of crude product was dissolved in 1 mL of an acetonitrile and water mixture (1:3) and detected using a P3000A HPLC pump and LC3000 semi-preparation equipment (preparation column model: GS-120-10-C18-AP 30 mm; Beijing Chuangxintongheng Science & Technology Co., Ltd., Beijing, China). The appropriate gradient for elution was calculated and the target peak was detected with LCMS (analysis column model: GS-120-5-C18-BIO, 4.6*250 mm).

The crude compound was desalted using an anion exchange resin, analysed and freeze-dried, which was retested for confirmation. 20 mg of purified peptide (90% to 95% purity) was obtained from 1.6 g of crude peptide.

MS: m/z 762.2 $[M+3H]^{3+}$.

Based on the characterising data available and presented herein it is understood that the compound prepared by way of this example is that identified above as the title compound. Otherwise, the compound that is prepared in Example 4 is a compound of the invention in which, in the compound of formula I, n is 0 and the compound of formula I is covalently bonded to amino acid SEQ ID No: 12 via the Lys residues. In any event, the compound of Example 4 is referred to hereinafter as "Compound D".

Example 5

Mouse Ear Swelling Model I 35 healthy male BALB/c mice of 6-8 weeks of age and average body weight of 18-25 g supplied by Changzhou Cvens Experimental Animal Co. Ltd. were housed and cared for about for 1 week prior to the experiment. The housing temperature was 25-27° C. with 74% humidity, with alternating 12 hour periods of light and darkness, and free access to food and water. The mice were randomly divided into 7 groups as described in Table 1 below, with 5 mice in each group The left ear of each mouse was used as autologous control. The right ear of each mouse was treated by various different treatments, as summarised in Table 1 below. 20 μL of xylene (Shanghai Aladdin Bio-Chem Technology Co., Ltd., Shanghai, China) was applied to the right ear of each mouse, both inside and outside. The ear started to swell in about 4 minutes. Then, 0.08 g of each study treatments or vehicles were applied to the right ears in each group. The mice were put back into their cages.

A cream based on montelukast sodium was made (Mon), consisting of the following components: montelukast sodium (200 mg; Arromax Pharmatech Co., Ltd, Suzhou, China), stearic acid (2 g), glycerin monostearate (2 g), hexadecanol (2 g), glycerin (5 g) and sodium hydroxide (0.25 g) (all Sinopharm Chemical Reagent Co. Ltd, Shanghai, China); ammonium acryloyldimethyltaurate/VP copolymer (0.13 g; Clariant Chemical (Guangzhou) Co., Ltd., Guangzhou, China); phenoxyethanol (0.3 g) and ethylhexyl glycerin (0.1 g) (both Shanghai Rayson Chemicals Co., Ltd., Shanghai, China); and purified water (88.42 g).

The stearic acid, glycerin monostearate and hexadecanol were mixed and heated to 85° C. with stirring until the mixture melted completely. The ammonium acryloyldimethyltaurate/VP copolymer, purified water and sodium hydroxide were mixed with stirring at 85° C. to form a homogenous colloidal suspension. Montelukast sodium, glycerin, phenoxyethanol and ethylhexyl glycerin were then combined with stirring until the montelukast completely dissolved.

The copolymer/water mixture was added to the stearic acid-containing mixture, which was emulsified by stirring quickly for five minutes using emulsification equipment. The resultant emulsion was cooled to 55° C., the montelukast-containing mixture was added with mixing. The resultant mixture was allowed to cool to room temperature to obtain the finished product.

Dexamethasone cream (DEX) was made using the same procedure, except that montelukast was replaced by 0.4 mg of dexamethasone (Shanghai Aladdin Bio-Chem Technology Co., LTD, Shanghai, China).

A gel including Compound A ("A gel") was made, which consisted of the following components: 0.5 g of Compound A powder (obtained from GL Biochem, Shanghai, China; prepared as described in Example 1 above), methyl cellulose (2.2 g; Shandong Guangda Technology Development Co., Ltd., ShanDong, China), glycerin (11 g) and propanediol 11 g (both Sinopharm Chemical Reagent Co. Ltd.), and purified water (75.3 g).

The methyl cellulose and water were mixed together and stirred until to a homogeneous colloidal suspension was formed. Then, the Compound A powder, glycerin and propanediol were added to the methyl cellulose/water mixture, and the resultant mixture quickly stirred for 5 minutes to obtain the finished product.

A gel based on Ala-Lys-Pro-Ser-Tyr-Hyp-Hyp-Thr-Tyr-Lys (Compound 1 (SEQ ID No: 12); 1.5 g; obtained as a powder from GL Biochem, Shanghai, China, and made by essentially the same process as that described in Example 1 above, without coupling montelukast at the end) was made by the same process as described above for Compound A ("1 gel").

Vehicle-1 in Table 1 below is the cream base without active ingredients. Vehicle-2 in Table 1 below is the gel base without active ingredients. Both were made using the same procedure as described above, without adding active ingredient.

TABLE 1

| Group | Drug concentration | Drug administration on right ear | Total amount of drugs (µg/mouse) |
|---|---|---|---|
| Model | / | Xylene | / |
| Vehicle-1 | / | xylene + cream without API | / |
| Vehicle-2 | / | xylene + gel without API | / |
| DEX | 10 µg/µL | xylene + Dex cream | 400 |
| Mon | 5 mg/g | xylene + Mon cream | 500 |
| 1 gel | 1.5 mg/g | xylene + Compound 1 gel | 120 |
| A gel | 0.5 mg/g | xylene + Compound A gel | 40 |

The mice were sacrificed by cervical dislocation after 40 minutes. The left and right ears were cut off. A skin pouch (Electron Microscopy Sciences, Hatfield, Pa., USA) with a diameter of 8 mm was used to take a piece of the ear from the same site of both ears. The weights were recorded and the swelling rates were calculated as follows:

Swelling rate=(right ear weight−left ear weight)/left ear weight×100% and the results showed in Table 2 below and FIG. 1.

TABLE 2

| Model | Vehicle 1 | Vehicle 2 | Dex Cream | Mon Cream | Compound 1 | Compound A |
|---|---|---|---|---|---|---|
| 97.4 0.03 | 95% 0.2 | 97% 0.35 | 45% 0.19 | 38% 0.25 | 61.5% 0.17 | 55% 0.06 |

The above results show that both test compounds reduce the xylene induced swelling.

Example 6

Acute Wound Model I 6-8 weeks old male C57BL/6 mice were supplied by Changzhou Cvens Experimental Animal Co. Ltd. Prior to any experiments being conducted, mice were housed under standardized conditions (at a constant temperature or 22±2° C., with alternating 12 hour periods of light and darkness), and were fed on a standard mouse diet with water, for about a week.

General anesthesia was induced using intraperitoneal 3% chloral hydrate (Sinopharm Chemical Reagent Co., Ltd.; 1 mL/10 g of body weight). The hair on the back was shaved by a baby hair shaver and depilated with cream. The skin area was wiped and sterilized with 75% alcohol twice.

EMS skin biopsy punch (Electron Microscopy Sciences, P.O. Box 550, 1560 Industry Road, Hatfield, Pa. 19440) with an 18 mm diameter was used to make a round wound on the midline of the back. Full thickness skin was removed, and the depth reached the fascia. The wounds left open without suture.

Different drugs were administered topically at 50 µL/wound, once daily from Day 0 to Day 7. The model group was given same amount of normal saline. There were 7 groups including 56 mice in this experiment, as shown in Table 3 below.

Recombinant Human Epidermal Growth Factor (rhEGF, Shanghai Haohai Biological Technology Co. Ltd, Shanghai, China) was purchased and prepared according to the manufacturer's instructions. Lyophilized rhEGF powder (100000 IU/vial) was dissolved in 20 mL of normal saline to make a solution with a 5000 IU/mL concentration. The working dose of rhEGF for this experiment was 1285 IU/wound.

Compound B was obtained as a powder from GL Biochem, and was prepared as described in Example 2 above). Ala-Lys-Pro-Ser-Tyr-Hyp-Hyp-Thr-DOPA-Lys (Compound 2; SEQ ID No: 4) was obtained as a powder from GL Biochem, and was prepared essentially as described in Example 2 above, but without coupling montelukast at the end. Powders were stored at −20° C. and dissolved in saline at the concentrations indicated in Table 3 below (L and H indicate low and high doses, respectively).

TABLE 3

| Group | Meaning | Number | Dose per wound per day |
|---|---|---|---|
| Control | C57 mice without wounds | / | / |
| Model | C57 mice with wounds/normal saline | 8 | Normal Saline |
| rhEGF | C57 mice with wounds/EGF | 8 | 1285 IU |
| 2 H | C57 mice with wounds/Compound 2 high dose | 8 | 77.15 µg |
| 2 L | C57 mice with wounds/Compound 2 low dose | 8 | 3.09 µg |
| B H | C57 mice with wounds/Compound B high dose | 8 | 112.53 µg |
| B L | C57 mice with wounds/Compound B low dose | 8 | 4.50 µg |

Figure 2:
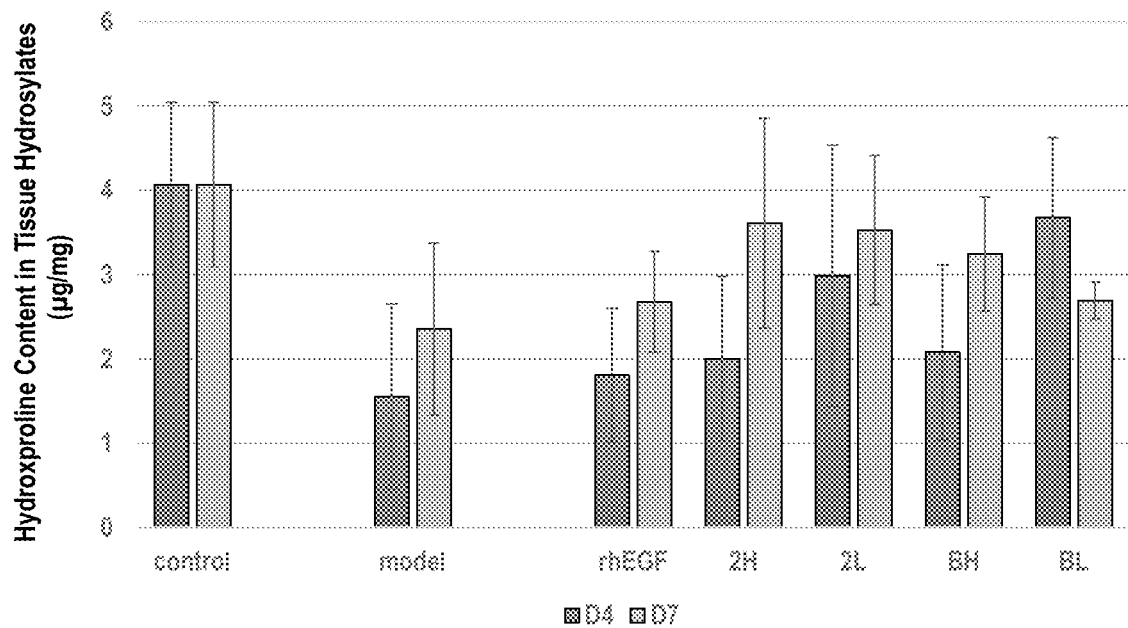
FIG. 2 shows Hyp content (and therefore level of recovery)

Hydroxyproline (Hyp) is a nonproteinogenic amino acid, found in collagen, containing approximately 12-14% Hyp by mass. Hyp content in tissue hydrolysates is thus a direct measure of the amount of collagen present, and the Hyp content presented in wound tissue indicates directly the level of recovery. The Hyp content in each group and Day 4 and Day 7 after commencement of treatment are shown in FIG. 2.

The results showed that test compounds improve Hyp content in all treatment groups. The lower dose of Compound 2 and Compound B both show effects at early stage (Day 4 (D4)). The higher doses of both test compounds also show accelerated effects on Hyp production at Day 7 (D7).

Figure 3:
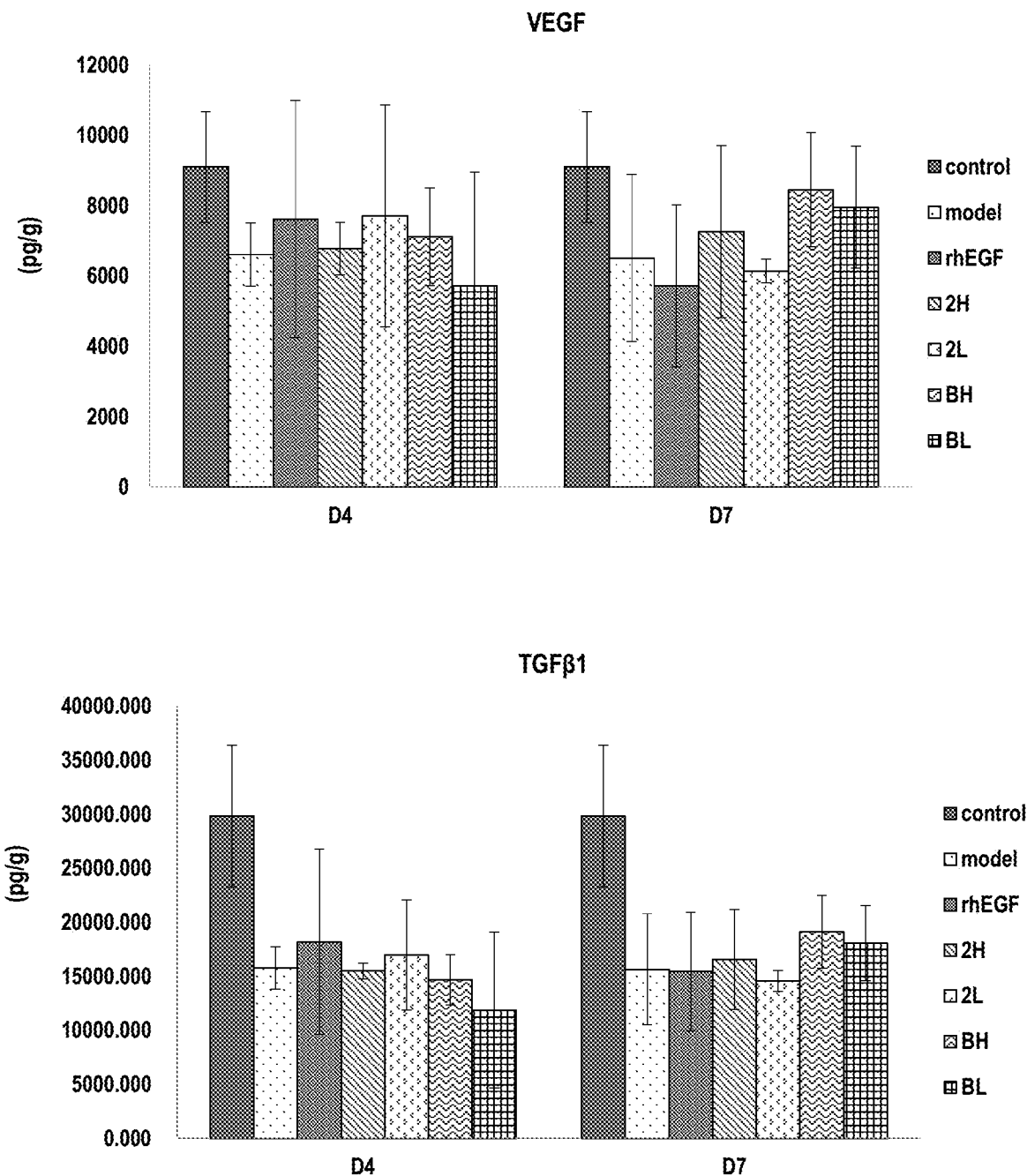
FIG. 3 shows vascular endothelial growth factor and transforming growth factor-beta 1 levels in wound tissues, in an acute wound mouse model.

Vascular endothelial growth factor (VEGF) and transforming growth factor-beta 1 (TGF-β1) play prominent roles in wound healing process. VEGF and TGF-β1 are often co-expressed in tissues in which angiogenesis occurs. The content of these two factors in wound tissues were also detected and are shown in FIG. 3.

The results showed that the two peptides could stimulate the production of VEGF and TGF-β1.

Example 7

Diabetic Wound Model I

A similar experiment with essentially the same protocol to that described in Example 6 above was carried out on 8 to 12 week-old male db/db mice (C57BL/KsJ-db/db), with a body weight of 35-45 g/mouse (Changzhou Cvens Experimental Animal Co. Ltd.).

An EMS skin biopsy punch with a 18 mm diameter was used to make wounds.

Different drugs were administered topically at 50 μL/wound, once daily from Day 0 to Day 12. The model group was given same amount of normal saline. There were 7 groups including 52 mice in this experiment shown in Table 4 below.

TABLE 4

| Group | Meaning | Dose/day | Concentration |
|---|---|---|---|
| Control | mice without wounds | / | / |
| Model | mice with wounds treated with normal saline | Normal Saline | / |
| rhEGF | mice with wounds treated with rhEGF | 1285 IU | 25.7 IU/μL |
| 1 L | mice with wounds treated with Compound 1 (low dose) | 3.05 μg | 0.061 μg/μL |
| A M | mice with wounds treated with Compound A (medium dose) | 22.3 μg | 0.446 μg/μL |
| Mon L | mice with wounds treated with montelukast (low dose) | 40 μg | 0.8 μg/μL |
| 1 + Mon | mice with wounds treated with half dose of Compound 1 and half dose of montelukast | 1.525 μg + 20 μg | 25 μg/μL + 25 μg/μL |

Photographs were taken for each wound every other day from Day 0. Photos were scanned into a computer, and wound areas calculated using ImageJ image analysis software (National Institute of Health, USA).

The unhealed wound area was expressed as a percentage of the original wound area:

$$A_t/A_0 \times 100\%,$$

where $A_0$ and $A_t$ refer to the initial area at Day 0 and the wound area at the date of measurement (time t), respectively.

Figure 4:
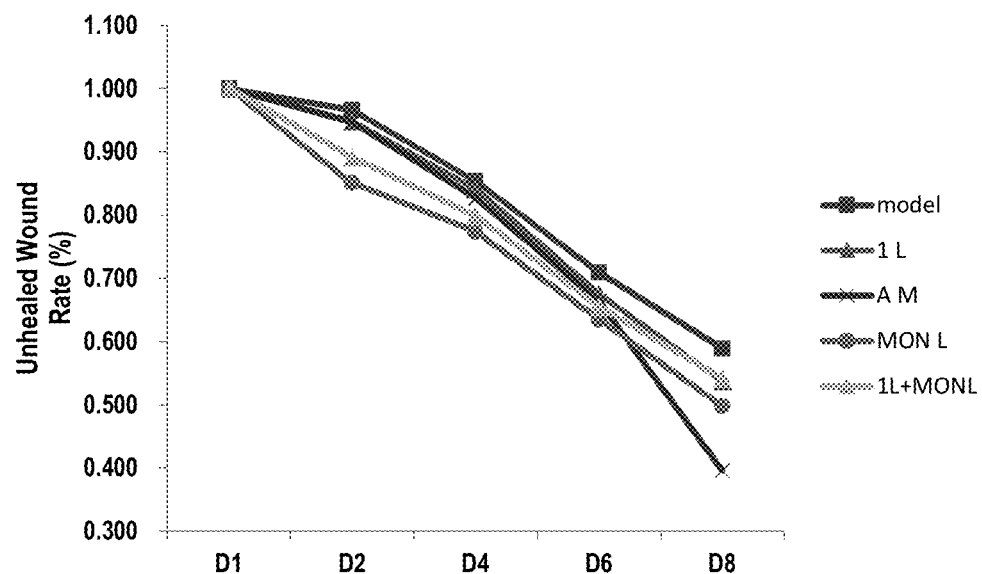
FIG. 4 shows unhealed wound rate.

The unhealed wound rate was showed in FIG. 4. The result showed that Compound A had the best effect on improving the wound recovery, and was better that of the combination of Compound 1 with montelukast.

Histological specimens were analyzed and skin regeneration, fibroblast proliferation, collagen regeneration scores (Masson score) and inflammation scores were estimated as follows.

Figure 5:
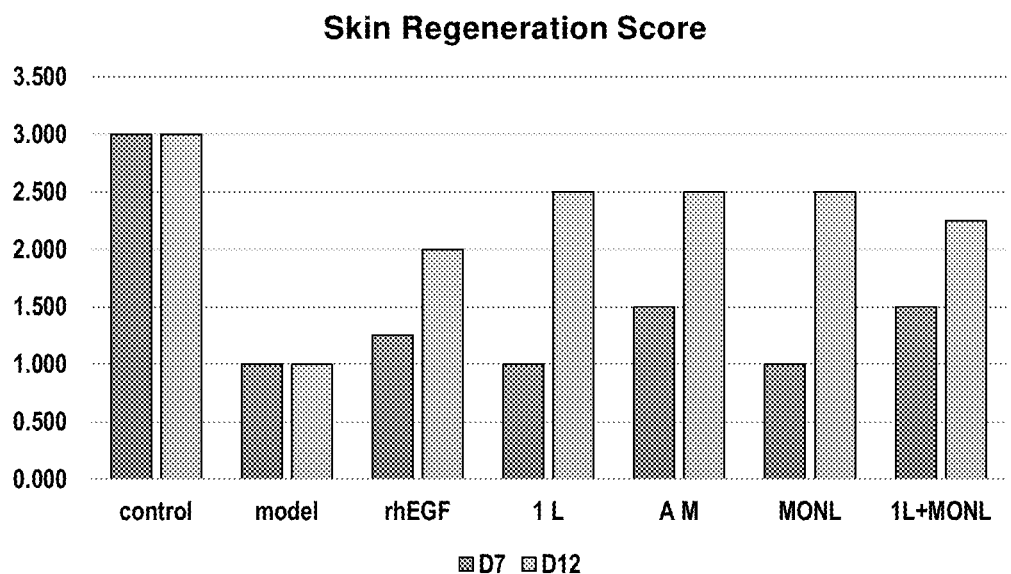
FIG. 5 shows skin regeneration.

The HE and Masson stained slices were observed under an optical microscope and were scored (1, 2 or 3 points) according to the following criteria. Skin regeneration score was 1 point when the newly generated skin covered area was no more than one third of the wound area; the score was 2 points when the newly generated skin covered an area greater than one third but less than two thirds of the wound area; and the score was 3 points when the newly generated skin covered area was at least two thirds of the wound area. The skin regeneration scores were showed in FIG. 5.

Figure 6:
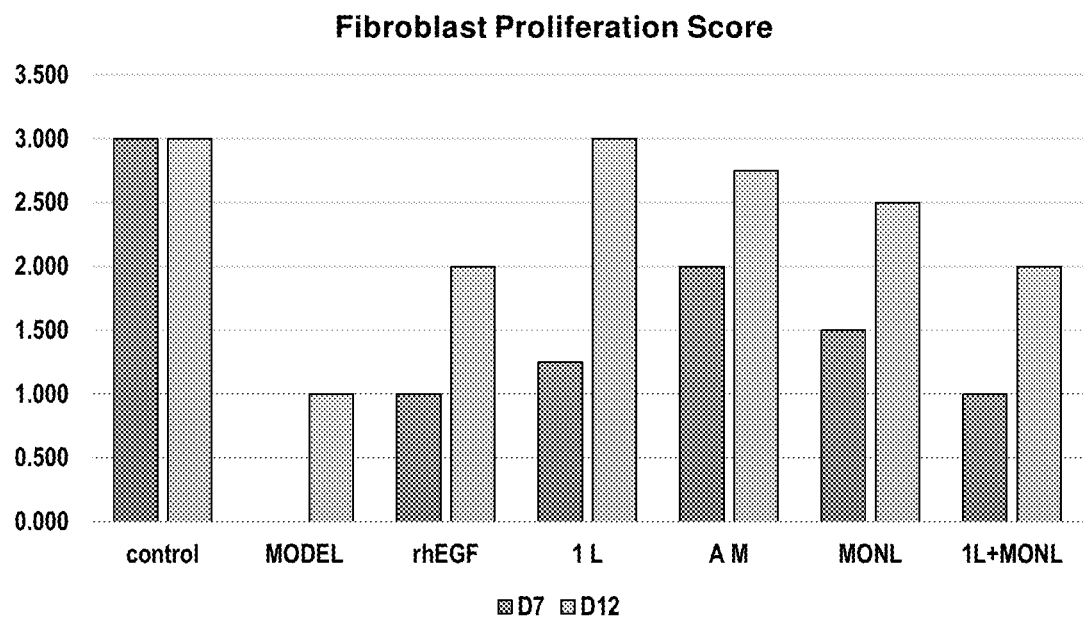
FIG. 6 shows fibroblast proliferation scores, in a diabetic wound mouse model.

Fibroblast proliferation was scored as the following criteria, and are presented in FIG. 6.

| Fibroblast proliferation score | |
|---|---|
| Collagen fiber hyperplasia | Score |
| Myofibroblastic proliferation | 1 |
| proliferation of fibrous tissue | 2 |
| Collagen appeared between the fibrous tissues | 3 |

The pathological analysis results showed that the Compound A and Compound 1 could promote the skin regeneration and fibroblast proliferation. The conjugate Compound A was slightly better, especially in relation to the fibroblast proliferation score.

Example 8

Diabetic Wound Model II

A similar experiment with essentially the same protocol to that described in Example 7 above was carried out on 8 to 12 week-old male db/db mice (C57BL/KsJ-db/db) with a body weight of 35-45 g/mouse (Changzhou Cvens Experimental Animal Co. Ltd.).

Different concentrations of Compound A and Compound 1 ("A" and "1" respectively, as indicated in the Table 5 below) were prepared in substantially the same way as described in Examples 6 and 7 above. Medium and low dosages of montelukast sodium ("Mon" in Table 5 below; MedChemExpress, MCE China, Shanghai, China) were dissolved in ultrapure water to obtain solutions with concentrations as described in Table 5 below (L, M and H indicate low, medium and high doses, respectively). In view of the low solubility of montelukast in water, the high dose montelukast test sample was prepared by dissolving montelukast in 100% ethanol, and then adding ultrapure water to form a solution with a concentration of 20 μg/μL in 20% ethanol.

Different drugs were administered topically at 50 μL/wound, once daily from Day 0 to Day 12, as show in in Table 5 below. The control group did not have wound inflicted.

TABLE 5

| Group | Meaning | Dose/day (μg) | Drug concentration (μg/μL) |
|---|---|---|---|
| Control | without wounds | / | / |
| Model | normal saline | Normal Saline | / |
| 1 H | Compound 1, 5× higher dose | 76.25 | 1.525 |
| 1 M | Compound 1, medium dose | 15.25 | 0.305 |
| 1 L | Compound 1, 5× lower dose | 3.05 | 0.061 |
| A H | Compound A, 5× higher dose | 111.51 | 2.2302 |
| A M | Compound A, medium dose | 22.3 | 0.446 |
| A L | Compound A, 5× lower dose | 4.46 | 0.0892 |
| Mon H | Mon, 5× higher dose | 1000 | 20 (20% ethanol) |

TABLE 5-continued

| Group | Meaning | Dose/day (μg) | Drug concentration (μg/μL) |
|---|---|---|---|
| Mon M | Mon, medium dose | 200 | 4 |
| Mon L | Mon, 5× lower dose | 40 | 0.8 |

The model group was given same amount of normal saline. There were 8 mice in each group. 4 mice were in the control group. The skin pieces taken during wound creation were used as the samples at Day 7 for the control group.

Figure 7:
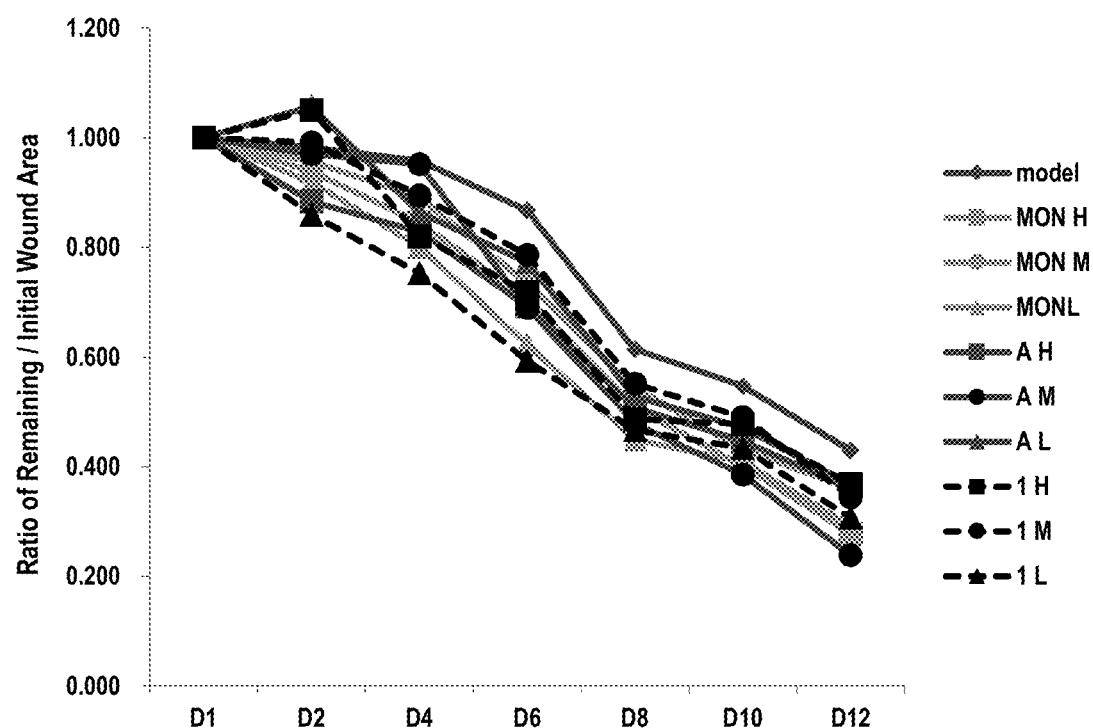
FIG. 7 shows the ratio of remaining wound area compared to the initial wound.
Figure 8:
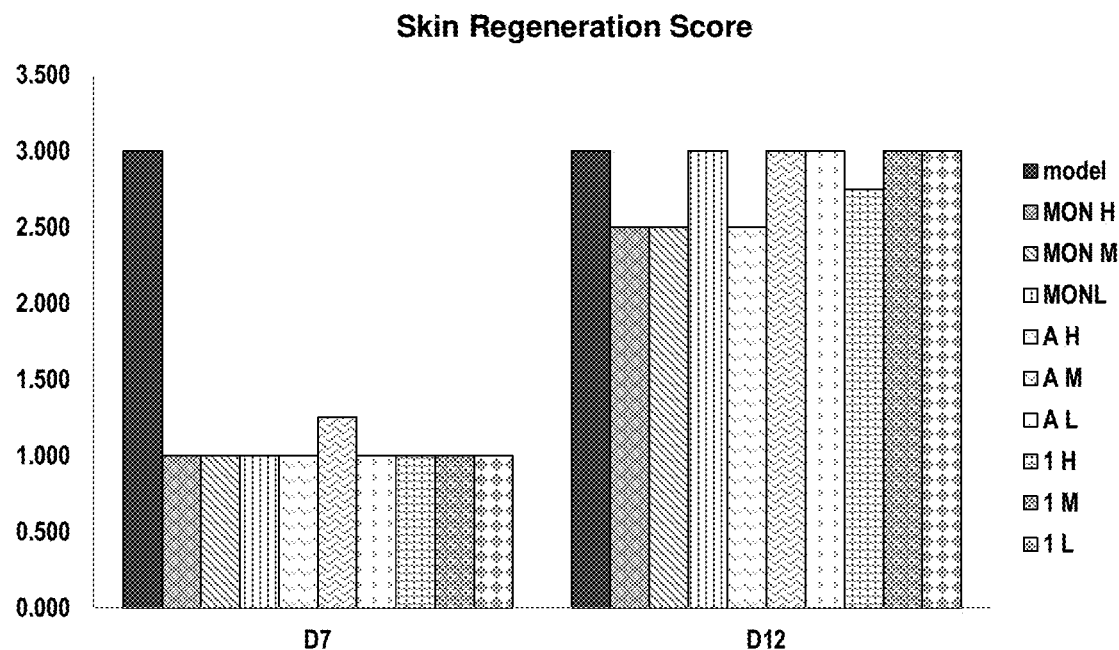
FIGS. 8 to 11 show the results of histopathological analyses in terms of various markers of wound healing (skin regeneration, fibroplastic proliferation, inflammation and Masson stain, respectively)
Figure 9:
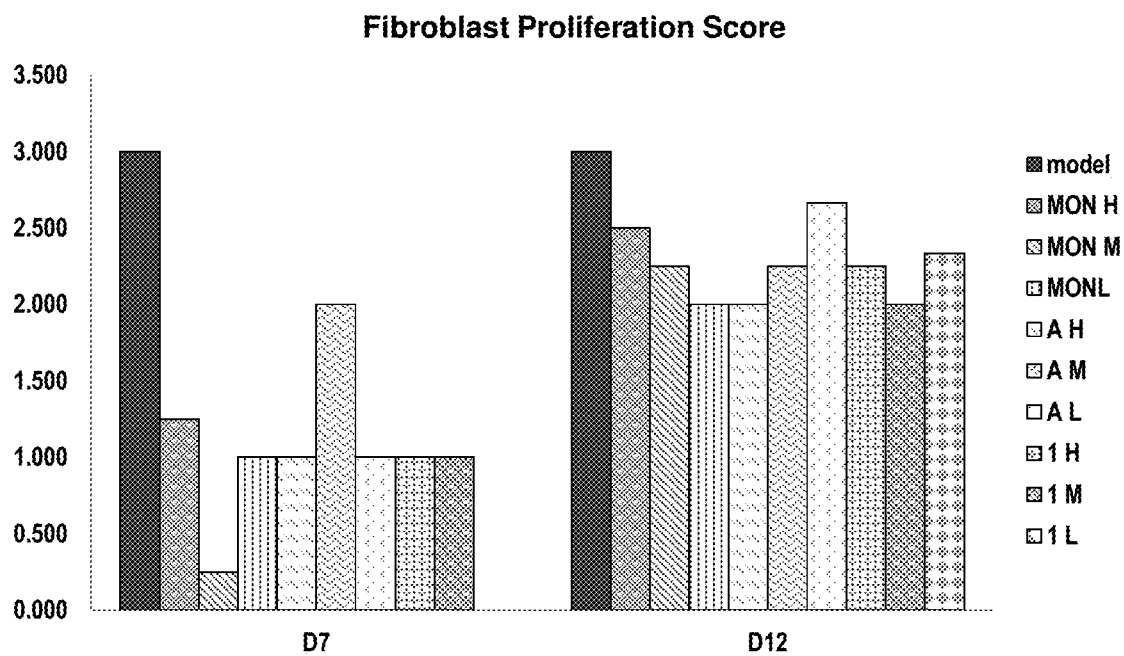
Figure 10:
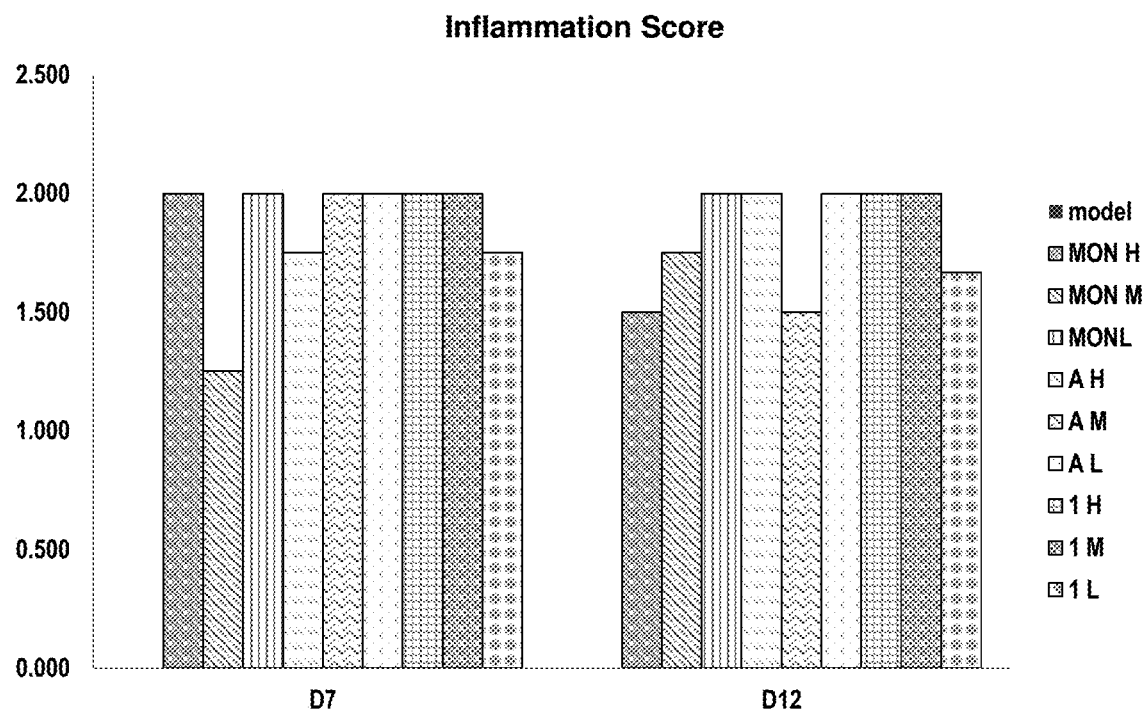
Figure 11:
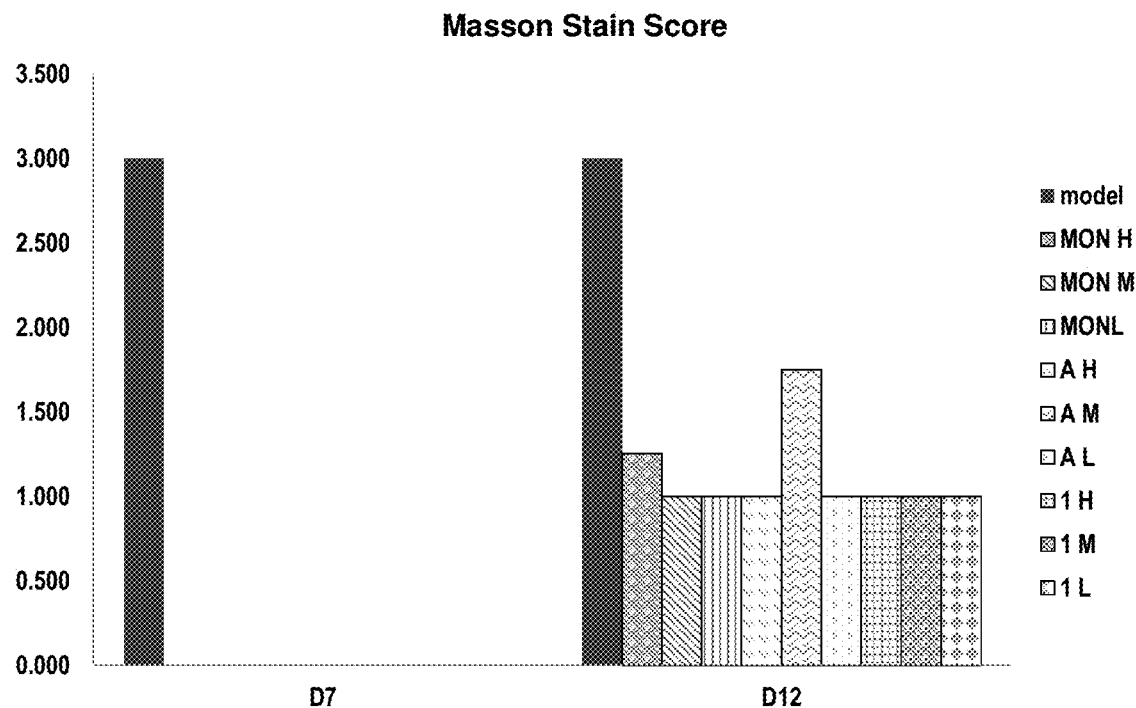

The effects of drugs on wound healing in the first 12 days were showed in Table 6 below and in FIG. 7, which show the ratio of remaining wound area of initial wound in different groups (±SD in the case of Table 6).

TABLE 6

| | | Model | Mon H | Mon M | Mon L | A H | A M | A L | 1 H | 1 M | 1 L |
|---|---|---|---|---|---|---|---|---|---|---|---|
| Mean | D1 | 1.000 | 1.000 | 1.000 | 1.000 | 1.000 | 1.000 | 1.000 | 1.000 | 1.000 | 1.000 |
| | D2 | 0.982 | 0.938 | 0.956 | 0.919 | 0.884 | 0.971 | 1.058 | 1.051 | 0.991 | 0.860 |
| | D4 | 0.958 | 0.845 | 0.891 | 0.802 | 0.829 | 0.952 | 0.864 | 0.821 | 0.895 | 0.753 |
| | D6 | 0.867 | 0.707 | 0.734 | 0.623 | 0.692 | 0.690 | 0.773 | 0.718 | 0.786 | 0.593 |
| | D8 | 0.614 | 0.508 | 0.543 | 0.449 | 0.508 | 0.479 | 0.527 | 0.486 | 0.552 | 0.467 |
| | D10 | 0.547 | 0.401 | 0.432 | 0.409 | 0.447 | 0.386 | 0.471 | 0.478 | 0.490 | 0.433 |
| | D12 | 0.429 | 0.277 | 0.359 | 0.292 | 0.361 | 0.238 | 0.368 | 0.368 | 0.344 | 0.306 |

The data show that the low dose of Compound 1 prompted wound healing in the earlier stages after wound infliction and that the medium dose of Compound A prompted better effects at the later stages.

Histological specimens were analyzed as described in Example 7 above, except that the collagen deposition score criterion for the Masson stained sample were as follows. A comparison was made with normal tissue. No clear blue staining was given 0 points; blue fiber appearing in a scattered pattern was scored as 1 points; if more blue fiber appeared, this was scored as 2 points, and a diffuse blue colour was given 3 points.

The results of histopathological analysis are shown in FIGS. 8 to 11 and show that all treatment groups accelerated wound healing, especially the medium dose of Compound A, which showed a significant promoting effect on collagen deposition.

Figure 12:
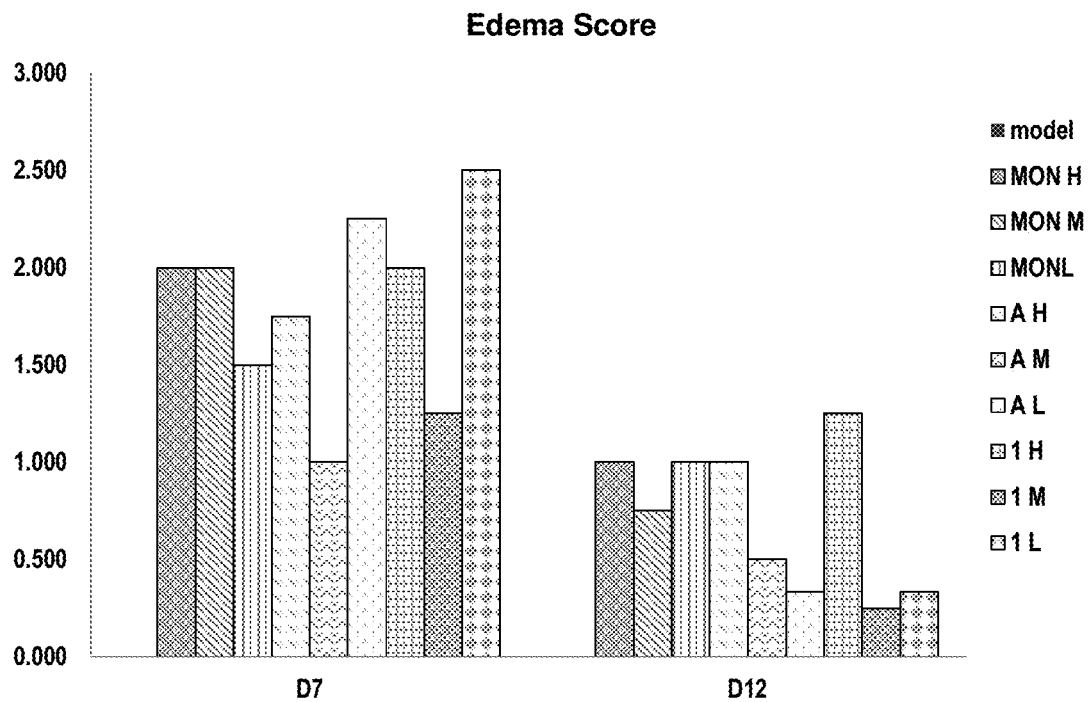
FIG. 12 shows levels of edema, in different groups in a further diabetic wound model.

The levels of edema in the different groups were also evaluated by histopathological analysis and the results are shown in FIG. 12. The data show that the medium dose of Compound A gave the best result.

Example 9

Mouse Ear Swelling Model II

A similar experiment with essentially the same protocol to that described in Example 5 above was carried out on 35 healthy male BALB/c mice. The mice were randomly divided into 7 groups as described in Table 7 below, with 5 mice in each group.

Compounds A, B, C and D were all obtained from GL Biochem Ltd.

In Table 7 below, hydrogels of Compounds A, B, C and D were prepared consisting of the amounts of active ingredients described, along with methyl cellulose (2.5%), propanediol (11%), glycerol (11%), acetic acid (pH regulator; 0 to 0.5 g). All excipients were obtained from Sinopharm Chemical Reagent Co. Ltd.). The gels were made up with water for injection.

Dexamethasone acetate cream (5 mg DEX in 10 g cream, Fuyuan Pharmaceutical Co. Ltd., Anhui, China) was used as positive control.

40 μL of the various treatments drugs were applied to the right ear of each group.

TABLE 7

| Group | Drug concentration | Drug administration on right ear | Total amount of drugs (μg/mouse) |
|---|---|---|---|
| Model | / | Xylene | / |
| Dex cream | 10 μg/μL | xylene + dexamethasone cream | 400 |
| A gel | 0.5 mg/g | xylene + Compound A gel | 20 |

TABLE 7-continued

| Group | Drug concentration | Drug administration on right ear | Total amount of drugs (μg/mouse) |
|---|---|---|---|
| B gel | 0.39 mg/g | xylene + Compound B gel | 16 |
| C gel | 0.52 mg/g | xylene + Compound C gel | 20.8 |
| D gel | 0.66 mg/g | xylene + Compound D gel | 26.4 |

The results are shown in FIG. 13. The conjugates all had a very good effect on eliminating the edema caused by acute inflammation.

Example 10

Acute Wound Model II

A similar experiment with essentially the same protocol to that described in Example 6 above was carried out on 6 to 8 week-old male C57BL/6 mice, EMS skin biopsy punch with a 12 mm diameter was used to make two round wounds on the midline of the back. The two circles were tangential to each other and the skin between the circles was cut along the upper and lower tangents. Scissors were used to trim the wound. The wound was an oval shape.

Different drugs were administrated topically at 50 μL/wound, once daily from Day 0 to Day 7. The model group was given same amount of normal saline. There were 10 groups including 80 mice in this experiment shown in Table 8 below.

TABLE 8

| Group | Meaning | Number | Dose (/wound/day) |
|---|---|---|---|
| Control | C57 mice without wounds | / | / |
| Model | C57 mice with wounds/normal saline | 8 | Normal Saline |
| rhEGF | C57 mice with wounds/EGF | 8 | 1285 IU |
| A | C57 mice with wounds/Compound A | 8 | 25 μg |
| B | C57 mice with wounds/Compound B | 8 | 19.64 μg |
| C | C57 mice with wounds/Compound C | 8 | 26.15 μg |
| D | C57 mice with wounds/Compound D | 8 | 32.93 μg |
| 1 | C57 mice with wounds/Compound 1 | 8 | 17 μg |
| Mon | C57 mice with wounds/montelukast | 8 | 8.5 μg |
| 1 + mon | C57 mice with wounds/Compound 1 and montelukast | 8 | 17 μg + 8.5 μg |

Photographs were taken for each wound every other day from Day 0, and the unhealed wound area expressed, as described in Example 6 above.

The unhealed wound rate is shown in FIG. 14. The results show that all four conjugates (A, B, C and D) had comparable effects on promoting the wound healing compared to the other groups.

Example 11

Cream Formulation

Sorbitan stearate (0.6 g), polysorbate-80 (1 g), hexadecanol (2 g), octanoic acid/decanoic acid glyceride (5 g), liquid paraffin (4 g), monostearate glyceride (2 g) and vaseline (5 g) (all Sinopharm Chemical Reagent Co. Ltd.) were mixed together, with stirring and heating to 85° C. until the mixture completely melted.

Methyl cellulose (0.5 g), glycerin (4 g), trehalose (0.5 g), polyethylene glycol 200 (4 g), phenoxyethanol (0.3 g) and ethylhexyl glycerol (0.1 g) (all Sinopharm Chemical Reagent Co. Ltd.) were mixed together with purified water (69.45 g), with stirring and heating to 85° C. to give a homogeneous colloidal suspension.

The two mixtures obtained above where mixed together with silicone oil (0.5 g) with quick stirring using emulsification equipment over 5 minutes. The resultant emulsion was cooled to 55° C.

Compound A (50 mg; see Example 1 above) was dissolved in purified water (1 g) and then combined with the emulsion mixture with stirring until it was uniform. The resultant mixture was allowed to cool to room temperature to obtain the finished product.

Example 12

Spray Formulation I

Hydroxypropyl methylcellulose (HPMC; 0.1 g), hydroxyethyl cellulose (0.1 g), glucose (5 g), phenoxy alcohol (0.5 g) (all Sinopharm Chemical Reagent Co., Ltd.) and purified water (93.25 g) were stirred together with heating to 85° C. to provide a homogeneous colloidal suspension. The mixture was then cooled to room temperature.

Compound A (50 mg; see Example 1 above) was dissolved in 1 g of purified water. This solution was added to the colloidal mixture. Uniform mixing gave the finished product.

Example 13

Spray Formulation II

A second spray was prepared using substantially the same procedure as that described in Example 12 above by adding the same aqueous solution of Compound A to a colloidal mixture made from slightly more HPMC and hydroxyethyl cellulose (0.2 g of each), along with the other components in the same amounts and 94.05 g of purified water.

Example 14

Gel Formulation I

This formulation was obtained using essentially the same procedure as that described in Examples 12 and 13 above, by adding the same aqueous solution of Compound A to a colloidal mixture made from 1 g each of HPMC and hydroxyethyl cellulose, along with the other components in the same amounts and 91.45 g of purified water.

Example 15

Gel Formulation II

A second gel was obtained using essentially the same procedure as described in Examples 12 to 14 above by adding the same aqueous solution of Compound A to a colloidal mixture made from 0.5 g of HPMC and 1.5 g of hydroxyethyl cellulose, along with the other components in the same amounts and 91.45 g of purified water.

Example 16

Gel Formulation III

A third gel was obtained using substantially the same procedure as described in Examples 12 to 15 above. Methyl cellulose (2.2 g) and propanediol 11 g (both Sinopharm Chemical Reagent Co., Ltd.), and glycerol (11 g) were first mixed with 74.75 g of purified water. Adding in the same aqueous solution of Compound A to the resultant colloidal mixture provided the finished product.

Example 17

Clinical Example I—Allergic Rhinitis Patient

A 45 year old female patient with allergic rhinitis had periodic snivels and nasal obstruction.

Spray formulation I (see Example 12 above), packed in a nasal spray bottle, was administered to each nostril separately, 2 to 3 times per day for 5 days.

The patient was instructed not to use her existing medication (oral montelukast sodium and budesonide) from the first dose of the spray formulation.

The snivels and nasal obstruction were apparently relieved as of the second administration. The patient found that she did not feel the need to take montelukast sodium orally over the course of the administration of the new formulation. The budesonide had been found to have lost efficacy within a couple of months of use.

Example 18

Clinical Example II—Burns Patient Symptom Relief

A male patent had a feeling of severe itch on his medial upper arm during the course of recovery from severe second degree burns with a VAS of 4 to 5.

Spray formulation I (see Example 12 above) was administrated to the wound and itch was relieved within one minute.

Example 19

Clinical Example III—Wounded Patient Symptom Relief

A patient was operated on and had severe pain from the surgical incision afterwards.

Spray formulation I (see Example 12 above) was administrated to the incision and pain was relieved within one minute.

Example 20

Clinical Example IV—Allergic Rhinitis Patients

38 Subjects enrolled in this study with seasonal and/or persistent allergic rhinitis. A majority of the subjects suffered with the disease for years and tried treatment with several medications, including steroids. The subjects were instructed not to use their existing medication from the first dose of the spray formulation.

Spray formulation I (see Example 12 above), packed in a nasal spray bottle, was administered to each nostril separately, 2 times per day for 7 days.

4 subjects did not complete the study. The feedback collected from the remaining 34 subjects is shown in Table 9 below.

Symptom incidence rate equals the number of subjects with the particular symptom, divided by the total number of subjects. Effective rate equals the number of subjects whose symptom was relieved, divided by the total number of subjects with the particular symptom.

TABLE 9

| Symptoms | Symptom incidence rate(%) | Effective rate(%) | Starting time of efficacy | Duration of efficacy |
| --- | --- | --- | --- | --- |
| Stuffy nose | 88.23 (30/34) | 66.57 (20/30) | Within 10 min | 2-5 hours |
| Running nose | 100 (34/34) | 67.65 (23/34) | Within 30 min | 2-4 hours |
| Itchy nose | 82.35 (28/34) | 60.71 (17/28) | Within 1 min | Half day |
| Sneeze | 94.12 (32/34) | 62.5 (20/30) | Within 1 min | Half day |
| Itchy eyes | 73.53 (25/34) | 68 (17/25) | Within 10 min | 2-4 hours |

The patient's found that the spray formulation was easy to administer and gave rise to no irritation. Nasal congestion was quickly relieved, along with the persistent sneezing and itchiness of the eyes. 16 of the subjects were checked by a clinician after using the spray for 7 days. 50% of the patients showed less turbinate swelling, 68.75% had less nasal secretions and 43% demonstrated reduced mucosal edema. No side effects were reported.

Example 21

Clinical Example V—Sore Throat Relieved by Atomization Inhalation

An 80-year-old Caucasian male had feelings associated with the onset of the common cold. Symptoms included an itchy and achy throat, and nasal congestion. 5 mL of spray formulation I (see Example 12 above) was loaded into a portable nebulizer (Feellife Medical INC, Sehnzhen, China). The suction nozzle of the nebulizer was placed in the mouth and the device turned on. The treatment lasted approximately 10 minutes. The inhalation was carried out only once. The following morning, all the symptoms of a cold had gone.

Example 22

Clinical Example VI—Operation Pain Relief in Burn Patient

A patient with large, deep second-degree burns covering the whole of his back was hospitalised in the burn department of Beijing Jishuitan Hospital. He was treated for severe burns and suffered from what he described as unbearable operation pain every time his dressing was changed, with a VAS of 7 to 9.

Spray formulation I (see Example 12 above), packed in a spray bottle, was sprayed directly onto the surface of the burn wound. After 5 minutes, the dressing was removed and changed for a new one. After use of the spray, the operation pain was reduced by about two thirds, according to the clinician's evaluation.

Example 23

Clinical Example VII—Operation Pain Relief in Laser Surgery Patients

Two subjects were tested in this study. The subjects received skin pigmentation removal surgery by fractional laser treatment.

Spray formulation I (see Example 12 above), packed in a spray bottle, was sprayed onto the surface of operation area. After 10 minutes, the laser operation started. Following use of the spray, the operating pain was reduced by about one third, according to the clinician's evaluation.

It is also normal for subjects that receive such laser surgery experience a burning pain for approximately 30 minutes after the treatment. However, in this study, the subjects did not feel any burning pain afterwards.

Example 24

Clinical Example VIII—Fever and Cough Relief

A 5-year-old boy caught a cold and developed a bad cough. His body temperature reached 38° C. during the night and he complained of a sore throat.

A spray formulation I (see Example 12 above), packed in a spray bottle, was administered as an oral spray, 4 times per day. The symptoms of fever and sore throat disappeared the following day. The cough disappeared after 3 days.

Example 25

Clinical Example IX—Contact Dermatitis Relief

A 53-year-old female had contact dermatitis on her neck. Rashes and an itchiness appeared upon the wearing a metal necklace.

Spray formulation I (see Example 12 above), packed in a spray bottle, was sprayed on the affected area. The feeling of itchiness was relieved within 5 minutes. After 2 doses (one in the evening and one the following morning), all symptoms had disappeared.

Example 26

Clinical Example X—Cold Relief

The patients were a 42-year-old female and her 10-year-old son. They had both caught a cold, suffering from a sore throat and runny nose.

Spray formulation I (see Example 12 above), packed in a spray bottle, was administered as an oral spray. After 2 doses (one in the evening and one in the next morning), all symptoms had disappeared.

Example 27

Clinical Example XI—Allergic Skin Disorder

A 27 years old female with sensitive skin had an acne-like allergic skin disorder with slight itchiness on her face. She also had patches of redness and swelling on her face.

Spray formulation I (see Example 12 above), packed in a spray bottle, was administered directly on to the affected areas on the face, 2 sprays at a time, 3 times per day. The feeling of itchiness was relieved within 30 minutes. The lesions completely disappeared after two weeks.

Example 28

Animal Model I—Idiopathic Pulmonary Fibrosis (IPF)

Experimental animals and grouping: 72 adult male Sprague Dawley rats, after 7 days of adaptive feeding, were divided into 6 groups: sham-operation (no infection and no treatment) group, IPF model group (no treatment), test group of high drug dose, test group of medium drug dose, test group of low drug dose and positive control group.

The dosages of Compound A (Example 1) were set at 0.5 mg/mL, 0.1 mg/mL and 0.02 mg/mL, as the high, medium and low doses, respectively. Oral administration of pirfenidone (Etuary®, Beijing Continent Pharmaceutical Co., Ltd., Beijing, China) as a 30 mg/kg single-bolus dose served as the positive control drug.

Modelling and administration: A pulmonary fibrosis model is established by intratracheal instillation of bleomycin. The rats were anaesthetised and placed on an operating table in the supine position, to expose the trachea. Bleomycin (5 mg/kg) saline solution was injected into the trachea through the gap between the tracheal cartilage rings. The sham-operation group were given an equal volume of normal saline. Quickly after administration, the rates were lifted vertically and rotated to evenly disperse the drug. Once the rats had recovered, after approximately 5 days, they were administrated different drugs according to the model plan for 28 days, consecutively. The experimental plan is shown in Table 10 below.

TABLE 10

| Group | Treatment | Dose |
| --- | --- | --- |
| Sham-operation | Saline | 50 μl |
| IPF model group | Saline | 50 μl |
| Positive control | pirfenidone | 250 mg/kg |
| Compound A high | Compound A | 975 μg/Rat |
| Compound A medium | Compound A | 195 μg/Rat |
| Compound A low | Compound A | 39 μg/Rat |

The following observation indicators were investigated.
1) Daily, general observation of the rats' activity, sensitivity to external stimuli, fur luster, hair colour, mouth, lip, nose, weight, diet, breathing and mortality.
2) Determination of the rats' lung organ coefficient and lung dry-wet weight ratio (i.e. the ratio of the animal's lung weight organ to the animal's body weight, i.e. the ratio of viscera to body weight).
3) During the formation of pulmonary fibrosis, the expression of growth factor (TGF-β), tumour necrosis factor-α (TNF-α) and other cytokines which are involved in the onset of fibrosis were measured. Standard ELISA methods were used to detect the contents of TGF-β, TNF-α, IL-1β, malondialdehyde (MDA) and the activity of superoxide dismutase (SOD) in lung tissue.
4) Detection of the content of collagen and fibrin metabolite (hydroxyproline) in the lungs, as specific indicators for evaluating the degree of pulmonary fibrosis.
5) Detection of histopathological changes in lung tissue, which is the most important and objective indicator for evaluating pulmonary fibrosis.

The results show that Compound A inhibits the overproduction of TGF-β and inflammatory cytokines. The results also show that the test drug has an antioxidation effect, by increasing SOD production and reducing lipid oxidation.

Example 29

Animal model II—Antitussive Experiment: Ammonia Induced Cough Method in Mice.

60 mice were randomly divided into 5 groups according to their body weight: CMC-Na negative control group, dextromethorphan hydrobromide positive control group and high, medium and low doses (of Compound A, Example 1) groups. Each group contained 12 mice, 6 males and 6 females.

The test drug was administered via atomization inhalation (0.15 mL/min) for 1 min, once daily for 5 days. The positive control drug was administered once daily by intragastric administration at 10 mg/kg for 5 days.

The mice were placed in an inverted beaker 1, 2, and 4 hours after the last drug administration (either Compound A or the positive control drug). 1 mL of aqueous ammonia (25.0 to 28.0%) was placed on top of a boiling water bath and was evaporated into the beaker. The mice were stimulated by ammonia vapor for a predetermined time of 63.1, 50.1, 39.8, 31.6, 25.1, 20.0, 15.9 or 12.6 seconds. The difference in the logarithm of two adjacent stimulating times was set at 0.1, and being 1.8, 1.7, 1.6, 1.5, 1.4, 1.3, 1.2 and 1.1. The mice were then quickly moved to a bell jar. The number of coughs within 1 minute was detected with a stethoscope. Typical coughs occurring three or more times in one minute are called 'cough' and those occurring less than three times in one minute are 'cough free'.

The ammonia stimulation time for the next mouse was determined according to the principle of the sequential method, i.e. if the first mouse was 'coughing', the next mouse was stimulated for a shorter period of time. Conversely, if the first mouse was 'coughless', the next mouse was stimulated for a longer period of time.

The $EDT_{50}$ was defined as the ammonia stimulating time at which half mice developed a "cough" and calculated by the equation:

$$EDT_{50} = lg^{-1} c/n$$

(c equals the sum of r and x, r is the number of animals in each stimulating time group, x is the logarithm of stimulation time and n was the number of animals in each group). The results are shown in Table 11 below.

TABLE 11

| group | dose | 1 h after administration | | 2 h after administration | | 4 h after administration | |
|---|---|---|---|---|---|---|---|
| | | $EDT_{50}$/s | R1/% | $EDT_{50}$/s | R1/% | $EDT_{50}$/s | R1/% |
| control | | 20.7 | | 21.5 | | 22.4 | |
| positive | 10 mg/kg | 50.1 | 241.7 | 44.7 | 207.3 | 41.4 | 184.8 |
| Compound A High | 39 μg/mouse | 28.2 | 135.9 | 29.3 | 135.9 | 26.1 | 116.6 |
| Compound A Medium | 195 μg/mouse | 34.1 | 164.7 | 39.8 | 184.8 | 39.8 | 177.8 |
| Compound A Low | 975 μg/mouse | 43.0 | 207.3 | 46.4 | 215.4 | 43.0 | 192.0 |

Where R1=($EDT_{50}$ in treatment group/$EDT_{50}$ in control group)×100%, R>130% indicates an antitussive effect. R>150% indicates a strong antitussive effect.

The results show that Compound A has a positive effect on cough relief.

Example 30

Animal Model III—Expectorant Experiment—Phenol Red Excretion Method in Mice.

50 Mice were randomly divided into 5 groups according to body weight: Normal saline, negative control group, ammonium chloride positive control group and high, medium and low dose of test drug (either Compound A, above, or Compound E, below). 10 mice in each group, 5 males and 5 females.

Compound A was administered via atomization inhalation (0.15 mL/min) for 1 min, once daily for 5 days and the positive control drug was administered by intragastric administration for 5 days.

Half an hour after the last administration of Compound A, 5% phenol red solution was injected into the abdominal cavity. The mice were sacrificed after a further half an hour. The skin of the neck was removed and the trachea from the thyroid cartilage to the bifurcation was separated, soaked it in 5% sodium bicarbonate solution with constant shaking. The sodium bicarbonate solution was used to detect the phenol red content.

The absorbance at 558 nm was detected by spectrophotometry (721G Spectrophotometer, Shanghai Jingke, Shanghai, China). The optical density value was used to calculate the phenol red content In the trachea by reference to the phenol red standard curve. The results of each group and the negative control group were tested for significant t-test. The results of the expectorant experiment are showed in Table 12 below.

TABLE 12

| Group | Treatment | Dose | Phenol red concentration (μg/ml) |
|---|---|---|---|
| Negative control | Normal saline | | 6.970 ± 0.339 |
| Positive control | $NH_4Cl$ | 0.15 g/kg | 10.335 ± 0.337** |
| High | Compound A | 39 μg/mouse | 9.001 ± 0.637 |
| Medium | Compound A | 195 μg/mouse | 10.480 ± 0.550*** |
| Low | Compound A | 975 μg/mouse | 10.489 ± 0.610*** |

Comparison with the negative control: *P < 0.05, P < 0.01, *P < 0.001

The results show that Compound A reduces mucus production, and therefore, reduces sputum.

Example 31

Effect of Compound a on the Activity of Human Herpes Simplex Virus, Type-II (HSV-II)

A serum free 1640 medium was prepared using RPM1640 powder (1000 mL dosage; Thermo Fisher Scientific China), L-glutamine (0.29 g; Sinopharm Chemical Reagent Co. Ltd, Shanghai, China), sodium bicarbonate (2.2 g; Sinopharm Chemical Reagent Co.), HEPEs (2.39 g; Thermo Fisher Scientific China) and deionized water (1000 mL).

The reagents were mixed until they dissolved, and the solution was sterilised by filtration. The mixture was formulated as either a complete medium containing 10% serum by adding 10% neonatal bovine serum before use or the mixture was formulated as a maintenance solution by adding 2% of neonatal bovine serum.

20 mg of Compound A (Example 1) was dissolved in 1 ml of 0.9% aqueous sodium chloride solution to prepare a 20 μg/μL stock solution. 0.05 mL of the stock solution was added to 1.95 mL of the complete (10%) medium to formulate a 500 μg/mL drug solution. The maintenance solution (2%) was used instead of the complete medium in antivirus tests Nos. 3 and 4, below.

Working solutions with concentrations of 250, 125, 62.5, 31.25, 15.625, 7.8125, 3.9063, 1.9531 and 0.9766 μg/mL were prepared by double dilution.

20.34 mg of sodium lauryl sulfonate (SDS; manufactured by AMRESCO LLC, Solon, Ohio, USA and packed by Biosharp Company, Hefei, China; purity: 99%) was dissolved in 10.17 mL of the complete culture medium to produce a 2000 μg/mL stock solution. A similar stock solution was also prepared in the same way using the maintenance solution for the antivirus tests. Working solutions, with concentrations as described above, were then prepared by double dilution.

2.25 mg of acyclovir (ACV; Zhiyuan Pharmaceutical Co., Ltd, Wuxi City, China; purity: 99.3%) was dissolved in 2.25 mL of the complete culture medium to form a 1000 g/mL stock solution. A similar stock solution was also prepared in the same way using the maintenance solution for the antivirus tests. 0.8 mL of each stock solution was double diluted to provide working solutions with concentrations of 500, 250 and 125 μg/mL. 0.2 mL of each stock solution was added to 1.95 mL of the complete culture medium to provide a concentration of 100 μg/mL, which was then diluted provide to solutions with concentrations of 50, 25 and 12.5 μg/mL.

1. HSV-2 Viral Toxicity Test 0.5 mL of a suspension of human herpes simplex virus type-II (HSV-2; SAV strain; Shanghai Institute of Cell Biology) was inoculated into the monolayer culture of Vero cells (Shanghai Institute of Cell Biology) and the virus suspension was removed after 1 hour of adsorption.

The maintenance solution was added and cultured at 37° C., under 5% $CO_2$, until more than 95% of the cells showed obvious pathological changes under a microscope (Nikon ECLIPSE TS100 inverted phase control microscope, with imaging system). The cells were harvested, repeatedly frozen and thawed (3 cycles) and then centrifuged at 3000 rpm for 10 minutes in a Model 400C Medical Low Speed Centrifuge (Beijing Baiyang Centrifuge Co., Ltd.). The supernatant was collected as viral solution.

The Vero cell suspension with a density of 2×10⁵ (cell number) was inoculated into a 96 well culture plate (Costar, Corning Inc., Oneonta, N.Y., USA) at 0.1 mL/well and cultured at 37° C., under 5% $CO_2$ in a Thermo Scientific CO₂ incubator for 18 hours, until a monolayer was visible under a microscope. The virus that was collected above was inoculated into the monolayer Vero cells with a 10-fold dilution in the maintenance solution in each 0.1 mL/well. The maintenance solution was replenished and cultured at 37° C., under 5% $CO_2$. Pathological changes of the cells were observed under a microscope after culturing for 24 hours. Each dilution was repeated in 3 wells. Normal cells were used as a control for the experiment. The virus virulence test was repeated 3 times.

Three visual fields were observed for each well. The average percentage of pathological cells (P) in the field of vision was determined.

The median infectious dose ($TCID_{50}$, 50% tissue culture infectious dose of a virus) of the virus was calculated according to the Reed and Muench conventional method, that is $TCID_{50}$, which is the logarithm of dilution showing a mortality next above 50%–(difference of logarithms× logarithm of dilution factor). Generally, the following formula is used to calculate "difference of logarithms" (difference of logarithms is also known as "proportionate distance" or "interpolated value"): Difference of logarithms=[(mortality at dilution next above 50%)−50%]/[(mortality next above 50%)−(mortality next below 50%)].

2. Cytotoxicity of Compound A and Control Drugs

Vero cells were inoculated on a 96-well culture plate and grew into monolayers. 0.2 mL of either Compound A solution (Example 1) or control drugs (20.34 mg of sodium lauryl sulfonate or 2.25 mg of acyclovir, as described above) was added to each well that contained a different concentration of complete medium correct (as described above). This was repeated in 3 wells for each concentration.

The solvent and normal cell cultures were used as a negative control. Cells were cultured at 37° C., under 5% $CO_2$, and growth and morphological changes of the cells were observed under the microscope for 2 days. Three visual fields under a microscope were selected for each well, the percentage of pathological cells was counted, and the average values were calculated. The evaluation time point of the test was set as 24 hours and the median toxic concentration ($TC_{50}$) and maximum non-toxic concentration ($TC_0$) were calculated. The experiment was repeated 3 times.

Cells were inoculated as described above. The solvent and normal cell cultures were used as negative controls. 24 hours after adding Compound A or the control drug, 5 mg/mL of 3-(4,5-dimethyl-2-thiazolyl)-2,5-diphenyl-2-H-tetrazolium bromide (MTT, Sigma-Aldrich (China), Shanghai, China) in PBS (diluted from a 10× stock solution, Sigma-Aldrich (China)) was introduced (20 μL/well), and cultivation continued for 4 hours. The supernatant in each well was then discarded and 150 μL of dimethyl sulfoxide (DMSO; Sigma-Aldrich (China)) was added, followed by 10 minutes of shaking in the dark at room temperature.

The optical absorption value ($OD_{550}$) at 550 nm was measured by an enzyme-linked immunosorbent meter (Multiskan Spectrum; Thermo Scientific, Shanghai, China).

3. Effect of Test Drug and SDS on the Cytopathic Effect of Viruses after Directly Acting on HSV-2

HSV-2 virus, preserved at −80° C. (in a Haier DW-86L486 ultra-low temperature freezer) with a determined $TCID_{50}$ was diluted to 200 $TCID_{50}$ at the determined titer (the $TCID_{50}$ value was initially determined each time, allowing the 200 $TCID_{50}$ to be determined). The 200 $TCID_{50}$ solutions were mixed with an equal volume of either Compound A or SDS liquid at which the viral titer was 100 $TCID_{50}$. The mixed solution was incubated in a water bath (DK-8B constant temperature electrothermal water bath; Shanghai Jinghong Biotech Co., Ltd.) at 37° C. for 1 hour, and then inoculated in a 96-well culture plate containing monolayer Vero cells. To each well was added 0.1 mL of the mixed solution.

The supernatant containing virus and drug was discarded after 1 hour of adsorption. The monolayer Vero cells were then washed twice with the maintenance solution. Finally, 0.2 mL of the maintenance solution was added to each well. The resultant mixture was continuously cultured at 37° C., under 5% $CO_2$, until the cytopathic rate of the drug free culture reached 95% under the microscope. The evaluating time point of the test was set as 24 hours.

Beside the experimental groups, three control groups were tested in parallel: solvent, no drug control (virus control) and normal cell control. Each group was made up of 3 wells and the experiment was repeated 4 times.

The virus culture was diluted to 0.1, 1, 10, 100 and 1000 $TCID_{50}$ and inoculated into monolayer cell cultures. Each dilution was conducted in triplicate. The cytopathic rates were observed for each well. There should no cytopathic effects at 0.1 $TCID_{50}$, whereas a cytopathic effect should be seen at 100 $TCID_{50}$; otherwise the neutralisation tests were not established.

The evaluation indicators were the same as that of the virus toxicity test. Three visual fields under a microscope were observed for each well. The average percentage of pathological cells (P) in the field of vision was determined and the median infective dose ($TCID_{50}$) of the virus was calculated according to the Reed and Muencl method (as described above).

The drug toxicity to the Vero cells was determined by the cell morphology method, while antiviral tests were carried out at non-toxic concentrations. After incubation with different concentrations of test drug and SDS for 1 hour, 100 $TCID_{50}$ HSV-2 (SAV strain) were inoculated into monolayer Vero cell culture.

The results show that the cytopathic effect of the cells caused by viral infection was inhibited to varying degrees, suggesting that Compound A has an inhibitory effect on HSV-2.

4. Effect of Test Drug and ACV on HSV-2 (Direct Method)

The virus was diluted to 100 $TCID_{50}$ and inoculated into monolayer Vero cells culture at 0.1 mL in each well. The supernatant was discarded after 1 hour of adsorption and the culture was washed 2 times with the maintenance solution. Solutions different concentrations of Compound A or control drug (acyclovir) were then added at 0.2 mL/well. The cultures were continuously cultivated at 37° C., under 5% $CO_2$. Each concentration was repeated in triplicate.

Beside the experimental groups, three control groups were tested in parallel: solvent, no drug control (virus control) and normal cell control.

During the culture period, the pathological changes were observed under a microscope and the tests were terminated when the cytopathic rate of the virus control reached >95%. The evaluation time point of the test was 24 hours and the experiments were repeated 3 times.

The judgment criteria were the same as those used in the virus toxicity test, i.e. three visual fields were selected for the microscopic examination of each well, the average percentage of pathological cells (P) in the field of vision was determined, taking the average of the three visual fields.

The linear regression equation was calculated according to the percentage of cytopathic effect for each reagent concentration group towards the drug concentration. The $IC_{50}$ values were calculated and the significance test of correlation coefficient was also calculated.

The results show that Compound A has an anti-virus effect.

Example 32

Synthesis of Montelukast-Ala-Lys-Pro-Ser-Tyr-Hyp-Hyp-Thr-Tyr-Lys (i.e. Montelukast Covalently Bonded to Amino Acid SEQ ID No: 12 at the N-Terminus)

The procedure as described in Example 1 was repeated. A second product peak was detected at 5.813 minutes by LCMS (analysis column model: GS-120-5-C18-BIO, 4.6*250 mm; detection: UV at 220 nm; solvent A: 0.1% TFA in MeCN, solvent A: 0.1% TFA in water; flow rate 1.0 mL/min.; volume: 10 µL) and the compound.

MS: m/z 875.90 $[M+2H]^{2+}$.

Based on the characterising data available and presented herein, it is understood that the compound isolated by way of this example is that identified above as the title compound. The compound of Example 32 is referred to hereinafter as "Compound E".

The yield ratio of Compound E to Compound A was 1:9.

Example 33

Synthesis of Hydrogenated Montelukast Styrene-Ala-Lys-Pro-Ser-Tyr-Hyp-Hyp-Thr-Tyr-Lys (i.e. Hydrogenated Montelukast Styrene Covalently Bonded to Amino Acid SEQ ID No: 12 at the N-Terminus)

The synthesis of the above-mentioned compound was exactly the same as the procedure for Compound A as described in Example 1, except that montelukast styrene was used as a reagent in place of montelukast.

MS: m/z 867.91 $[M+2H]^{2+}$.

Based on the characterising data available and presented herein, it is understood that the compound prepared by way of this example is that identified above as the title compound. Otherwise, the compound that is prepared in Example 33 is a compound of the invention in which, in the compound of formula I, and n is 0 and the compound of formula I is covalently bonded to amino acid SEQ ID No: 12 at the N-terminus. In any event, the compound of Example 33 is referred to hereinafter as "Compound F".

Example 34

Clinical Example XII—Fever Relief

An 11 year old boy showed symptoms of a fever, with a temperature at 39° C. at 2100 hours. The subject was also coughing intermittently and had a runny nose.

A spray formulation of Compound E (2 mg; see Example 32 above) in normal saline solution (5 mL) was administered to each nostril as a mist by atomisation (device: handheld nebulizer, Lifetrons Beaute NS-400) at 2200 hours, over a period of 5 minutes.

At 2215 hours the subject fell asleep. Around midnight, the subject began to sweat and his temperature fell a little. A second dose of Compound E (1 mg) in normal saline solution (2.5 mL) was administered in the same way, at 0030.

By 0330, the subject's temperature decreased to 37.0° C. By 0800, the subject had a normal temperature. Thus, between 2215 hours the previous day and 0800 hours the following day, a cough was only observed for half a minute in total. During sleep that night, there was no observable nasal obstruction. In the morning, although a runny nose had returned, it had improved significantly compared to 11 hours previously.

The subject received a third dose of Compound E (1 mg) in normal saline solution (2.5 mL), which was administered in the same way, at 0830 hours the same morning. Two hours later, his nose had stopped running. After that and up until 1500 hours on the same day, the subject had no fever, cough or runny nose.

At 1530 hours on the second day, the subject received a forth dose of Compound E (1 mg) in normal saline solution (10 mL) by atomisation (apparatus: Yuyue, Air-compressing Nebulizer, 403 M). At 2045 hours, the subject had a temperature of 37.1° C. At 2100 hours, the subject received a fifth dose of Compound E (1 mg) in normal saline solution (10 mL) by atomisation. By 2215 hours, the subject's temperature was 36.8° C.

Example 35

Comparison of Compounds A and E in a Mouse Ear Swelling Model (III)

A similar experiment with essentially the same protocol to that described in Example 5 above was carried out on 30 healthy male BALB/c mice. The mice were randomly divided into 6 groups as described in Table 13 below, with 5 mice in each group.

TABLE 13

| Group | Drug concentration | Drug administration on right ear | Total amount of drug |
|---|---|---|---|
| Model | / | Xylene | / |
| Dexamethasone cream | 5 mg/g | xylene + Dexamethasone cream | 0.8 g |
| Budesonide Nasal spray | 0.64 mg/ml | xylene + Budesonide Nasal Spray | 40 µl |
| Fluticasone Propionate Nasal Spray | 50 µg/100 ml | xylene + Fluticasone Propionate Nasal Spray | 40 µl |
| Compound A | 0.5 mg/ml | xylene + Compound A | 40 µl |
| Compound E | 0.5 mg/ml | xylene + Compound E | 40 µl |

Compounds A and E were obtained from GL Biochem Ltd and synthesized as described in Examples 1 and 32, respectively. Aqueous solutions of Compounds A and E were prepared in by dissolving 0.5 mg of powder in 1 mL normal saline (0.9% w/v NaCl solution). 40 µL of the prepared solution was applied to the right ear of each group.

Dexamethasone acetate cream (5 mg DEX in10 g cream, Fuyuan Pharmaceutical Co. Ltd., Anhui, China), Budesonide Nasal Spray (32 µg/spray×120 spray, 0.64 mg/ml, AstraZeneca AB, SE-151 85, Södertälje, Sweden) and fluticasone propionate nasal spray (50 mcg/spray, 0.05% w/w, Glaxo Wellcome, S.A., Avenida de Extremadura n° 3-09400, Aranda de Duero, Burgos, Spain) were used as positive control. The cream was put into a 1 mL syringe to measure the dose based on calibration of weight and volume. The bottles of the spray were opened and 40 µL of the liquid was pipetted and applied to the right ear of each group.

The results are shown in FIG. 15.

The conjugates all had a very good effect on eliminating the edema caused by acute inflammation. The anti-inflammatory effects of Compounds A and E were equivalent.

Example 36

Synthesis of Montelukast-Ala-Lys-Pro-Ser-Tyr-Hyp-Thr-Tyr-Hyp-Lys (i.e. montelukast covalently bonded to amino acid SEQ ID No: 24 at the N-terminus) and Montelukast Styrene-Ala-Lys-Pro-Ser-Tyr-Hyp-Thr-Tyr-Hyp-Lys (i.e. montelukast styrene covalently bonded to amino acid SEQ ID No: 24 at the N-terminus)

Essentially the same procedure as that described in Example 1 above, but in which the order of the coupling steps were adjusted to provide according to the above amino acid sequence, was employed to synthesise a modified peptide with SEQ ID No: 24.

Following this, montelukast was coupled onto the N-terminal of Ala. The two title compounds were separated and thereby purified by LCMS, in a similar manner to that described in Example 32 above. The compounds are referred to hereinafter as Compound G (that comprising montelukast) and Compound H (that comprising montelukast styrene), respectively.

The ratio for the yield of Compounds G:H 1:7
MS (Compound G): m/z 876.6[M+2H]$2^+$
MS (Compound H): m/z 867.6 [M+2H]$2^+$

Example 37

In Vitro CysLTR1 FLIPR Antagonist Test

The in vitro antagonist effect of Compounds A and E (see Examples 1 and 32 above, respectively) on a CYSLTR1 cell line was measured using Fluo-4 Direct™ Calcium Assay Kit [Cat #F10471, Thermo Fisher Scientific]. As a comparison, montelukast sodium and montelukast styrene were also tested and pranlukast was used as a positive control. 10 different concentrations were tested in duplicate for each compound.

A CYSLTR1/HEK293 cell line was used. The cells were prepared and 20 µL of the cell suspension were added to the 384-well plates (20K/well; poly-D-Lysine protein coating plate, Greiner #781946). The plate was placed at 37° C. in a 5% $CO_2$ incubator overnight.

A probenecid in FLIPR assay buffer was prepared from the relevant starter pack (Cat. no. F10471): A 250 mM stock solution of water-soluble probenecid was prepared by adding 1 mL of Fluo-4 Direct™ calcium assay buffer to 77 mg vials containing probenecid (Component B for Cat. nos. F10471). 10 mL of Fluo-4 Direct™ calcium assay buffer and 200 µL of the 250 mM probenecid stock solution was added to one bottle of Fluo-4 Direct™ calcium reagent (Component A). This 2× Fluo-4 Direct™ calcium reagent loading solution was sufficient for two microplates. The solution was vortexed allowed to sit for 5 minutes (protected from light), to ensure that the reagent was completely dissolved. The reagent was prepared fresh each day All of the compounds were dissolved and serially diluted in Fluo-4 Direct™ calcium assay buffer (without probenecid). The cell plate was removed from the incubator and the medium was decanted gently. 20 µL of the compounds were transferred to the cell plate, and 20 µL of 2× Fluo-4 Direct™ No-wash Loading Buffer was added. The final concentrations of each compound were 100, 30, 10, 3, 1, 0.3, 0.1 and 0.03 µM. The plate was incubated for 50 minutes at 37° C. in a 5% $CO_2$ incubator for 10 minutes at room temperature. Fluorescence was measured using the instrument settings appropriate for excitation at 494 nm and emission at 516 nm.

The data were analysed using Prism (GraphPad Software, USA) and IC50s calculated for each compound. The results are shown in Table 14 below.

TABLE 14

| Compound ID | IC50 (nM) | Max Dose (nM) |
|---|---|---|
| Compound A | 474.7 | 100000 |
| montelukast styrene | 158.5 | 100000 |
| Compound E | 90.55 | 100000 |
| montelukast sodium | 13.74 | 100000 |
| Pranlukast | 0.2178 | 1000 |

The results show that montelukast has 11 times the affinity to CysLTR1 than montelukast styrene. Therefore, Compound E had 5 times higher affinity than that of Compound A and the affinity for the tested compounds to CysLTR1 was largely determined by the structure of the compound of formula I.

Example 38

In Vitro CysLTR1 FLIPR Antagonist Test

The assay procedure described in Example 37 above was repeated for Compound G (see Example 36 above), and further Compound E (see Example 32 above) as a comparison. The results are shown in Table 15.

TABLE 15

| Compound ID | IC50 (nM) | Max Dose (nM) |
|---|---|---|
| Compound G | 99.55 | 50000 |
| Compound E | 140.5 | 50000 |
| montelukast sodium | 7.300 | 50000 |
| Pranlukast | 0.2496 | 4000 |

The results show that Compounds G and H had the same level of affinity to CysLTR1, which indicated that the change on amino acid sequence of the peptide had little impact on the affinity of the conjugate.

Example 38

Lipopolysaccharide-Induced Lung Injury in Mice

36 BALB/c male mice, with a body weight of between 20 to 22 g, were housed in an animal facility at between 22 to 26° C. and between 55 and 75% relative humidity and a 12/12 hour day/night cycle with food and water ad libitum.

Mice were randomly divided into 6 groups as indicated in Table 16 below.

TABLE 16

| Group | Dose | Administration |
|---|---|---|
| Control | / | / |
| Model | Saline | Inhalation |
| Compound A | 2 mg/kg | Inhalation |
| Compound G (high dose) | 10 mg/kg | Inhalation |
| Compound G (medium dose) | 2 mg/kg | Inhalation |
| Compound G (low dose) | 0.4 mg/kg | Inhalation |

Compound A was prepared analogously to the procedure described in Example 1 above and Compound G was prepared analogously to the procedure described in Example 36 above.

The mice were anesthetized by intraperitoneal injection of 3% chloral hydrate (0.1 mL/10 g). Tongues were pulled aside with tweezers. Lipopolysaccharide (LPS, 1 mg/mL, 50 µL) administered by pipetted to the back wall of the pharynx. Tongues were released and noses pinched immediately for 30 seconds. Then, mice were released from retention and placed back into cages wake naturally. Mice in the control group were treated with the same volume of saline.

Test compounds were administered via atomization/inhalation for 30 minutes after LPS induction. 24 hours later, mice were sacrificed.

The thoracic cavity was quickly opened and whole lung was stripped. A piece of lung tissue weight was accurately weighed, and saline was added at a ratio of 9 mL saline to 1 g of lung tissue. Then, the tissue was homogenized and centrifuged for 10 minutes at 3000 rpm. The homogenate was used to detect TGF-β1 using ELISA kit (Beijing 4A Biotech Co., Ltd, China) and the results showed in FIG. 16.

The results showed that both compounds of the invention reduce inflammatory cytokines in lung tissues. The IL-1β concentration in lung tissue in Compound A group was the same level as in low dose group for Compound G. Compound G also shows dose dependent efficacy in reducing inflammatory cytokines.

Thus, although both compounds of the invention have been shown to be efficacious in treating LPS-induced acute lung injury in mice, the potency of Compound G was about 5 times higher than that of Compound A.

Example 39

Idiopathic Pulmonary Fibrosis (IPF) Model in Rats 60 adult SD rats (30 male, 30 female) were purchased from Zhejiang Experimental Animal Center, China. Animals were housed at between 21 and 26° C. and at between 40 and 70% relative humidity with free access to food and water.

After 7 days of adaptive feeding, rats were randomly divided into 6 groups as showed in Table 17 below.

TABLE 17

| Group | Drug | Dose | Administration Method |
| --- | --- | --- | --- |
| Sham | / | / | inhalation |
| Model | normal saline | 0.15 mL | inhalation |
| pirfenidone | pirfenidone | 240 mg/kg | Gavage |
| Compound A | Compound A | 2 mg/kg | inhalation |
| Compound E | Compound E | 2 mg/kg | inhalation |
| Compound H | Compound H | 2 mg/kg | inhalation |

The rats were anaesthetized and placed on an operating table in the supine position, to expose the trachea. Bleomycin (5 mg/kg, Bleomycin Hydrochloride for Injection, Haizheng Pfizer Pharmaceutical Co., Ltd.) and saline solution were injected into the trachea through the gap between the tracheal cartilage rings.

The sham-operation group was given an equal volume of normal saline instead of bleomycin. The rats were lifted vertically immediately after administration and were rotated to allow bleomycin to evenly disperse.

Once the rats had recovered, after approximately 7 days, they were administrated different drugs according to the model plan. 6.5 mg of test compounds of the invention in powdered form was accurately dissolved in 5 mL saline to make a 1.3 mg/mL solution. 0.15 mL of the solution was atomized and inhaled by each rat. Inhalation was carried out once a day.

For the pirfenidone group, 12 pirfenidone capsules (Beijing Contini Pharmaceutical Co., Ltd., Beijing, China; 100 mg) were opened and the contents were fully suspended in 25 mL of 0.5% CMC-Na solution to obtain 48 mg/mL suspension. The dosage of pirfenidone was 1.0 mL/200 g in rats, i.e. 240 mg/kg, and was given by oral gavage.

After 28 days of administration, rats were anesthetized by intraperitoneal injection of chloral hydrate and then sacrificed. The thoracic cavity was quickly opened and whole lung tissue was removed. The lung wet weight was weighed, and the lung coefficient was calculated (lung wet weight/rat weight×1000) and are shown in Table 18 below.

TABLE 18

| Group | Lung coefficient (%) |
| --- | --- |
| Sham | 6.272 ± 0.496 |
| Model | 13.484 ± 1.395 |
| Compound A | 8.771 ± 0.897 |
| Compound E | 9.462 ± 1.123 |
| Compound H | 9.825 ± 0.647 |
| pirfenidone | 10.218 ± 0.984 |

The results show that Compounds A, E and H reduce lung edema caused by bleomycin induction.

The right bronchus was ligated, and the left lung was perfused with formalin solution in vitro. The left lung was cut and fixed in formalin solution for pathological examination. The remaining tissue was stored in a refrigerator at −80° C. for later use.

The fixed lung tissue was embedded in paraffin and sequential 4 µm sections were stained with haematoxylin-eosin (HE) and modified Masson's trichrome. Fibrotic lung injury was assessed morphologically by semiquantitative parameters. All morphological changes were scored according to the severity of damages. The scores were given as 1-4 according to light, mild, moderate and severe degree, respectively. No lesion was scored as 0. Evaluation from HE stained sections were the sum of degree of fibrosis and inflammation. Evaluation from Masson stained sections were the degree of collagen deposition in pulmonary interstitium. The results are shown in Table 19 below.

TABLE 19

| | HE evaluation | | Masson evaluation | |
| --- | --- | --- | --- | --- |
| Group | Mean | SD | Mean | SD |
| Sham | 1.78 | 1.20 | 0.22 | 0.44 |
| Model | 5.50 | 0.84 | 2.67 | 0.52 |
| pirfenidone | 5.50 | 0.52 | 2.50 | 0.5 |
| Compound A | 4.00 | 0.45 | 2.25 | 0.4 |
| Compound E | 4.29 | 0.29 | 1.86 | 0.37 |
| Compound H | 4.00 | 0.14 | 1.88 | 0.13 |

The results showed that, compared with the sham-operated group, pulmonary fibrosis and bronchial pneumonia in the model group were more serious. Compared with the Model group, the pathological changes in the drug-treated group were similar, and the degree of pathological changes were less. The order of pathological changes was as follows: Model, pirfenidone>Compound E>Compound A>Compound H>sham. These results indicated that Compounds A, E and H prevent bleomycin-induced lung fibrosis in mice and their efficacy was stronger than that of the pirfenidone.

Example 40

Synthesis of Montelukast-Ala-Lys-Pro-Ser-Tyr-Hyp-Hyp-Thr-Tyr-Hyp-Lys (i.e. Montelukast Styrene Covalently Bonded to Amino Acid SEQ ID No: 20 at the N-Terminus)

Essentially the same procedure as that described in Example 1 above, but in which the order of the coupling steps were adjusted to provide according to the above amino acid sequence, was employed to synthesize a modified peptide with SEQ ID No: 20.

Following this, montelukast was coupled onto the N-terminal of Ala. The compound was purified by LCMS, in a similar manner to that described in Example 32 above. The title compound is are referred to hereinafter as Compound J.

MS: m/z 924.15 [M+2H]2+

Example 41

Mouse Ear Swelling Model IV

Essentially the same protocol to that described in Example 5 above was carried out on 15 healthy male BALB/c mice, using Compounds J (see Example 40 above) as test compound. The mice were randomly divided into 3 groups as described in Table 20 below, with 5 mice in each group.

A hydrogel of Compound J was prepared comprising 0.5 mg/g of active ingredient and methyl cellulose (2.5%), propanediol (11%), glycerol (11%), acetic acid (pH regulator; 0 to 0.5 g). All excipients were obtained from Sinopharm Chemical Reagent Co. Ltd. The gel was made up with water for injection.

Dexamethasone acetate cream (DEX cream; 5 mg of dexamethasone in 10 g of cream; Fuyuan Pharmaceutical Co. Ltd., Anhui, China) was used as a positive control. 40 μL of the various treatments drugs were applied to the right ear of each group.

TABLE 20

| Group | Drug concentration | Drug administration on right ear | Total amount of drugs (μg/mouse) |
|---|---|---|---|
| Model | / | Xylene | / |
| Dex cream | 10 μg/μL | xylene + dexamethasone cream | 400 |
| Compound J | 0.5 mg/g | xylene + Compound J gel | 20 |

The results are shown in FIG. 17. Compound J showed a very good effect on eliminating the edema caused by acute inflammation.

Example 42

Clinical Example—Allergic Conjunctivitis

A 52 year old female patient was diagnosed with allergic conjunctivitis and experienced with swollen eyelids, itching, and a watery nose.

0.5 mg/mL of Compound G in saline solution was packed in a spray bottle. The spray was administered to each eye, 2 to 3 times per day for 7 days.

The patient felt relief from itchy eyes after one treatment. At the second day of treatment, her eyelids were less swollen. Full recovery of all symptoms took place within a week.

Example 43

Clinical Example—Ulcerative Colitis

A hospitalized patient with ulcerative colitis suffered from severe symptoms including bad abdominal pain and cramping, frequent diarrhea (more than 20 time a day), and did not respond to over-the-counter medications. The patient experience rectal bleeding, passing small amounts of blood with stools, an urgency to defecate and fever.

A hydrogels of Compound G was prepared consisting of 0.5 mg/g of active ingredient, methyl cellulose (2.5%), propanediol (11%), glycerol (11%), acetic acid (pH regulator; 0 to 0.5 g). All excipients were obtained from Sinopharm Chemical Reagent Co. Ltd. The gel was made up with water for injection.

The patient was given 2 g of the above gel by anal administration, once daily. On the second day after administration, the diarrhea reduced to only 5-6 times daily, with less bleeding.

The patient continued to use the gel with a view to determining long-term efficacy.

The invention claimed is:

1. A peptide-containing compound that comprises: a peptide component comprising the amino acid sequence X-Pro-Y-Z (SEQ ID NO: 5) wherein:
   X represents 1 to 2 amino acid residues each independently selected from the group consisting of Ala and Lys;
   Y is selected from the group consisting of Ser and pSer;
   Z represents 1 to 7 amino acid residues each independently selected from the group consisting of Tyr, pTyr, 3Hyp, 4Hyp, Thr, pThr, DOPA and Lys; and
   at least one of the Ala and/or Lys residues is covalently bonded to one or more compounds of formula I by an amide bond formed by reaction of the carboxylic acid group in formula I and one or more free amino groups in the Ala and/or Lys residues:

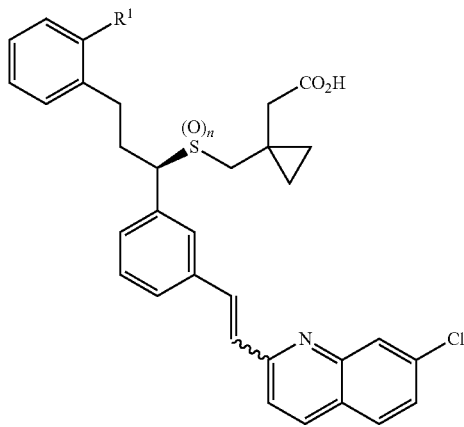

wherein:
   the squiggly bond represents cis or trans orientation relative to the carbon-carbon double bond;
   $R^1$ is selected from the group consisting of —C(CH$_3$)$_2$OH, —COCH$_3$, —C(CH$_3$)=CH$_2$ and —C(CH$_3$)$_2$H; and
   n is 0, 1 or 2,
as well as regioisomers, stereoisomers, and pharmaceutically- or cosmetically-acceptable salts of said peptide-containing compound.

2. The peptide-containing compound as claimed in claim 1, wherein the peptide component consists of a sequence of 6 to 12 amino acids.

3. The peptide-containing compound as claimed in claim 1, wherein the peptide component is covalently bonded to at least one compound of formula I through a primary amide linkage formed at the N-terminal of said peptide component.

4. The peptide-containing compound as claimed in claim 1, wherein the peptide component is covalently bonded to at least one compound of formula I through a primary amide linkage formed through at least one free —NH$_2$ group in one or more amino acids in the sequence that is not the N-terminal amino acid.

5. The peptide-containing compound as claimed in claim 1, wherein at least one of the amino acids in the peptide component is lysine.

6. The peptide-containing compound as claimed in claim 5, wherein at least about 5% of the amino acids are lysine.

7. The peptide-containing compound as claimed in claim 1, wherein at least about 5% of the amino acids of the peptide component contain an aromatic group.

8. The peptide-containing compound as claimed in claim 7, wherein at least about 10% of the amino acids contain an aromatic group.

9. The peptide-containing compound as claimed in claim 7, wherein the amino acids that contain an aromatic group are selected from the group consisting of tyrosine and 3,4-dihydroxyphenylalanine.

10. The peptide-containing compound as claimed in claim 1, wherein the peptide component consists of the amino acid sequence X-Pro-Y-Z (SEQ ID NO: 5).

11. The peptide-containing compound as claimed in claim 1, wherein the peptide component comprises or consists of the amino acid sequence:

G$^1$-Lys-Pro-G$^2$-T-Hyp-G$^3$-Lys       (SEQ ID NO: 7), wherein
   G$^1$ is absent or represents Ala;
   G$^2$ is selected from the group consisting of Ser and pSer;
   T is selected from the group consisting of DOPA, Tyr and pTyr;
   Hyp is selected from the group consisting of 3Hyp and 4Hyp;
   G$^3$ represents 1 to 4 amino acid residues each independently selected from the group consisting of Tyr, pTyr, 3Hyp, 4Hyp, Thr, pThr and DOPA.

12. The peptide-containing compound as claimed in claim 11, wherein the peptide component comprises or consists of the amino acid sequence:

Lys-Pro-G$^2$-T-Hyp-G$^3$-Lys       (SEQ ID NO: 8).

13. The peptide-containing compound as claimed in claim 11, wherein G$^1$ represents Ala.

14. The peptide-containing compound as claimed in claim 11, wherein the peptide component comprises or consists of the amino acid sequence:

Ala-Lys-Pro-G$^2$-T-Hyp-Hyp-Thr-G$^4$-Lys       (SEQ ID NO: 9), wherein G$^4$ is selected from the group consisting of Tyr, pTyr, 3Hyp, 4Hyp, Thr, pThr and DOPA.

15. The peptide-containing compound as claimed in claim 11, wherein G$^2$ represents Ser.

16. The peptide-containing compound as claimed in claim 11, wherein T represents Tyr.

17. The peptide-containing compound as claimed in claim 14, wherein G$^4$ represents Tyr or DOPA.

18. The peptide-containing compound as claimed in claim 17, wherein the peptide component comprises or consists of the amino acid sequence:

Ala-Lys-Pro-Ser-Tyr-Hyp-Hyp-Thr-DOPA-Lys       (SEQ ID NO: 4);

Ala-Lys-Pro-pSer-Tyr-Hyp-Hyp-Thr-DOPA-Lys   (SEQ ID NO: 11);

Ala-Lys-Pro-Ser-Tyr-Hyp-Hyp-Thr-Tyr-Lys   (SEQ ID NO: 12); and

Ala-Lys-Pro-pSer-Tyr-Hyp-Hyp-Thr-Tyr-Lys       (SEQ ID NO: 13).

19. The peptide-containing compound as claimed in claim 18, wherein the peptide component comprises or consists of the amino acid sequence:

Ala-Lys-Pro-Ser-Tyr-Hyp-Hyp-Thr-Tyr-Lys       (SEQ ID NO: 12).

20. The peptide-containing compound as claimed in claim 11, wherein G$^3$ represents -V$^1$-Thr-Tyr-V$^2$-, wherein V$^1$ is covalently bonded to Hyp and V$^2$ is covalently bonded to Lys, and V$^1$ and V$^2$ are, independently, either absent or represent one Hyp residue.

21. The peptide-containing compound as claimed in claim 20, wherein -V$^1$-Thr-Tyr-V$^2$- represents -Hyp-Thr-Tyr-, -Hyp-Thr-Tyr-Hyp-, or -Thr-Tyr-Hyp-.

22. The peptide-containing compound as claimed in claim 11, wherein the peptide component comprises or consists of the amino acid sequence:

| | |
|---|---|
| Ala-Lys-Pro-Ser-Tyr-Hyp-Hyp-Thr-DOPA-Hyp-Lys | (SEQ ID NO: 18); |
| Ala-Lys-Pro-pSer-Tyr-Hyp-Hyp-Thr-DOPA-Hyp-Lys | (SEQ ID NO: 19); |
| Ala-Lys-Pro-Ser-Tyr-Hyp-Hyp-Thr-Tyr-Hyp-Lys | (SEQ ID NO: 20); |
| Ala-Lys-Pro-pSer-Tyr-Hyp-Hyp-Thr-Tyr-Hyp-Lys | (SEQ ID NO: 21); |
| Ala-Lys-Pro-Ser-Tyr-Hyp-Thr-DOPA-Hyp-Lys | (SEQ ID NO: 22), |
| Ala-Lys-Pro-pSer-Tyr-Hyp-Thr-DOPA-Hyp-Lys | (SEQ ID NO: 23); |
| Ala-Lys-Pro-Ser-Tyr-Hyp-Thr-Tyr-Hyp-Lys | (SEQ ID NO: 24); and |
| Ala-Lys-Pro-pSer-Tyr-Hyp-Thr-Tyr-Hyp-Lys | (SEQ ID NO: 25). |

23. The peptide-containing compound as claimed in claim 22, wherein the peptide component comprises or consists of the amino acid sequence:

Ala-Lys-Pro-Ser-Tyr-Hyp-Thr-Tyr-Hyp-Lys (SEQ ID NO: 24).

24. The peptide-containing compound as claimed in claim 1, wherein one or more compounds of formula I is/are covalently bonded through an N-terminal Ala or Lys residue and/or a C-terminal Lys residue.

25. The peptide-containing compound as claimed in claim 1, wherein one or two compounds of formula I is/are covalently bonded to the peptide component.

26. The peptide-containing compound as claimed in claim 25, wherein one compound of formula I is covalently bonded to the peptide component.

27. The peptide-containing compound as claimed in claim 1, wherein R$^1$ is selected from the group consisting of —C(CH$_3$)$_2$OH, —C(CH$_3$)=CH$_2$ and —C(CH$_3$)$_2$H; and/or n is 0 in the one or more compounds of formula I.

28. The peptide-containing compound as claimed in claim 1, wherein the one or more compounds of formula I is selected from the group consisting of montelukast, montelukast styrene, or hydrogenated montelukast styrene.

29. The peptide-containing compound according to claim 1, wherein the peptide component comprises the amino acid sequence of Ala-Lys-Pro-Ser-Tyr-Hyp-Thr-Tyr-Hyp-Lys (SEQ ID NO: 24), the compound of formula I is montelukast, and wherein the montelukast is covalently bonded to the N-terminal Ala residue.

30. The peptide-containing compound as claimed in claim 12, wherein the peptide component comprises or consists of the amino acid sequence:

| | |
|---|---|
| Lys-Pro-Ser-Tyr-Hyp-DOPA-Lys | (SEQ ID NO: 14); or |
| Lys-Pro-Ser-pTyr-Hyp-DOPA-Lys | (SEQ ID NO: 15). |

31. A pharmaceutical formulation comprising the peptide-containing compound as defined in claim 1, or a pharmaceutically- or cosmetically-acceptable salt thereof, and a pharmaceutically- or cosmetically-acceptable, adjuvant, diluent or carrier.

32. The pharmaceutical formulation as claimed in claim 31 wherein the pharmaceutically- or cosmetically-acceptable adjuvant, diluent or carrier is a topical adjuvant, diluent or carrier for topical administration.

33. The pharmaceutical formulation as claimed in claim 32, which is in the form of a gel, a spray, a cream, an ointment or a dry powder.

34. The pharmaceutical formulation as claimed in claim 32, which further includes an antiinflammatory agent.

35. A kit of parts comprising components:
(A) a pharmaceutical formulation as defined in claim 32; and
(B) a pharmaceutical formulation including an antiinflammatory agent in admixture with a pharmaceutically-acceptable adjuvant, diluent or carrier,
wherein components (A) and (B) are each provided in a form for co-administration together or separately as different formulations.

36. A method of treatment of idiopathic pulmonary fibrosis, comprising administering the peptide-containing compound of claim 1, or a pharmaceutically- or cosmetically-acceptable salt thereof, or a formulation comprising said compound or salt, to a patient in need of such treatment.

37. The method as claimed in claim 36, wherein the method comprises administering compound(s) by oral, inhalation, intravenous, cutaneous or subcutaneous, nasal, intramuscular, intraperitoneal, pulmonary or anorectal delivery.

38. The method as claimed in claim 37, wherein the method comprises pulmonary administering by way of a spray comprising a powder aerosol or an aqueous mist for atomization.

39. The method as claimed in claim 38, wherein the spray is liquid comprising a water (aerosol) spray and excipients comprise one or more of a viscosity modifier, a sugar, an emulsifier, a buffering agent, an alcohol and a preservative.

40. The method as claimed in claim 38, comprising an inhalation device selected from the group consisting of a pressurized metered-dose inhaler, a dry powder inhaler, a soft mist inhaler, and a nebulizer.

* * * * *

```
                        SEQUENCE LISTING

<160> NUMBER OF SEQ ID NOS: 48

<210> SEQ ID NO 1
<211> LENGTH: 37
<212> TYPE: PRT
<213> ORGANISM: Hyalophora cecropia
<220> FEATURE:
<221> NAME/KEY: MOD_RES
<222> LOCATION: 1
<223> OTHER INFORMATION: Lysine residue with N-terminal hydrogen
<220> FEATURE:
<223> OTHER INFORMATION: Cecropin A
<220> FEATURE:
<221> NAME/KEY: MOD_RES
<222> LOCATION: 37
<223> OTHER INFORMATION: Lysine residue with C-terminal carboxamide

<400> SEQUENCE: 1
```

```
Xaa Trp Lys Leu Phe Lys Lys Ile Glu Lys Val Gly Gln Asn Ile Arg
1               5                   10                  15

Asp Gly Ile Ile Lys Ala Gly Pro Ala Val Ala Val Val Gly Gln Ala
                20                  25                  30

Thr Gln Ile Ala Xaa
                35

<210> SEQ ID NO 2
<211> LENGTH: 35
<212> TYPE: PRT
<213> ORGANISM: Hyalophora cecropia
<220> FEATURE:
<221> NAME/KEY: MOD_RES
<222> LOCATION: 1
<223> OTHER INFORMATION: Lysine residue with N-terminal hydrogen
<220> FEATURE:
<223> OTHER INFORMATION: Cecropin B
<220> FEATURE:
<221> NAME/KEY: MOD_RES
<222> LOCATION: 35
<223> OTHER INFORMATION: Lysine residue with C-terminal carboxamide

<400> SEQUENCE: 2

Xaa Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
                20                  25                  30

Lys Ala Xaa
        35

<210> SEQ ID NO 3
<211> LENGTH: 37
<212> TYPE: PRT
<213> ORGANISM: Homo sapiens
<220> FEATURE:
<221> NAME/KEY: MOD_RES
<222> LOCATION: 1
<223> OTHER INFORMATION: Lysine residue with N-terminal hydrogen
<220> FEATURE:
<223> OTHER INFORMATION: LL-37
<220> FEATURE:
<221> NAME/KEY: MOD_RES
<222> LOCATION: 37
<223> OTHER INFORMATION: Lysine residue with C-terminal carboxamide

<400> SEQUENCE: 3

Xaa Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Xaa
                35

<210> SEQ ID NO 4
<211> LENGTH: 10
<212> TYPE: PRT
<213> ORGANISM: Artificial Sequence
<220> FEATURE:
<223> OTHER INFORMATION: Synthetic mefp-1 decapeptide
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine
```

```
<400> SEQUENCE: 4

Ala Lys Pro Ser Tyr Xaa Xaa Thr Xaa Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: VARIANT
<222> LOCATION: 1
<223> OTHER INFORMATION: Wherein Xaa is alanine or lysine or is absent
<220> FEATURE:
<221> NAME/KEY: VARIANT
<222> LOCATION: 2
<223> OTHER INFORMATION: Wherein Xaa is alanine or lysine
<220> FEATURE:
<221> NAME/KEY: VARIANT
<222> LOCATION: 4
<223> OTHER INFORMATION: Wherein Xaa is serine or phosphoserine
<220> FEATURE:
<221> NAME/KEY: VARIANT
<222> LOCATION: 5
<223> OTHER INFORMATION: Wherein Xaa is selected from the group
      consisting of tyrosine, phosphotyrosine, 3-hydroxyproline,
      4-hydroxyproline, threonine, phosphothreonine,
      3,4-dihydroxyphenylalanine or lysine
<220> FEATURE:
<221> NAME/KEY: VARIANT
<222> LOCATION: 6..11
<223> OTHER INFORMATION: Wherein Xaa is selected from the group
      consisting of tyrosine, phosphotyrosine, 3-hydroxyproline,
      4-hydroxyproline, threonine, phosphothreonine,
      3,4-dihydroxyphenylalanine or lysine or is absent

<400> SEQUENCE: 5

Xaa Xaa Pro Xaa Xaa Xaa Xaa Xaa Xaa Xaa Xaa
1               5                   10

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4,5
<223> OTHER INFORMATION: Wherein Xaa is 3- or 4-hydroxyproline

<400> SEQUENCE: 6

Ala Pro Ser Xaa Xaa Thr
1               5

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: VARIANT
<222> LOCATION: 1
<223> OTHER INFORMATION: Wherein Xaa is absent or represents alanine
<220> FEATURE:
<221> NAME/KEY: SITE
<222> LOCATION: 4
<223> OTHER INFORMATION: Wherein Xaa is serine or phosphoserine
<220> FEATURE:
<221> NAME/KEY: SITE
<222> LOCATION: 5
```

```
<223> OTHER INFORMATION: Wherein Xaa is selected from the group
      consisting of 3,4-dihydroxyphenylalanine, tyrosine and
      phosphotyrosine
<220> FEATURE:
<221> NAME/KEY: SITE
<222> LOCATION: 6
<223> OTHER INFORMATION: Wherein Xaa is 3- or 4-hydroxyproline
<220> FEATURE:
<221> NAME/KEY: VARIANT
<222> LOCATION: 7
<223> OTHER INFORMATION: Wherein Xaa is selected from the group
      consisting of tyrosine, phosphotyrosine, 3-hydroxyproline,
      4-hydroxyproline, threonine, phosphothreonine and
      3,4-dihydroxyphenylalanine
<220> FEATURE:
<221> NAME/KEY: VARIANT
<222> LOCATION: 8..10
<223> OTHER INFORMATION: Wherein Xaa is absent or is selected from the
      group consisting of tyrosine, phosphotyrosine, 3-hydroxyproline,
      4-hydroxyproline, threonine, phosphothreonine and
      3,4-dihydroxyphenylalanine

<400> SEQUENCE: 7

Xaa Lys Pro Xaa Xaa Xaa Xaa Xaa Xaa Xaa Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 3
<223> OTHER INFORMATION: Wherein Xaa is serine or phosphoserine
<220> FEATURE:
<221> NAME/KEY: SITE
<222> LOCATION: 4
<223> OTHER INFORMATION: Wherein Xaa is selected from the group
      consisting of 3,4-dihydroxyphenylalanine, tyrosine and
      phosphotyrosine
<220> FEATURE:
<221> NAME/KEY: SITE
<222> LOCATION: 5
<223> OTHER INFORMATION: Wherein Xaa is 3- or 4-hydroxyproline
<220> FEATURE:
<221> NAME/KEY: VARIANT
<222> LOCATION: 6
<223> OTHER INFORMATION: Wherein Xaa is selected from the group
      consisting of tyrosine, phosphotyrosine, 3-hydroxyproline,
      4-hydroxyproline, threonine, phosphothreonine and
      3,4-dihydroxyphenylalanine
<220> FEATURE:
<221> NAME/KEY: VARIANT
<222> LOCATION: 7..9
<223> OTHER INFORMATION: Wherein Xaa is selected from the group
      consisting of tyrosine, phosphotyrosine, 3-hydroxyproline,
      4-hydroxyproline, threonine, phosphothreonine and
      3,4-dihydroxyphenylalanine, or is absent

<400> SEQUENCE: 8

Lys Pro Xaa Xaa Xaa Xaa Xaa Xaa Xaa Lys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is serine or phosphoserine
```

```
<220> FEATURE:
<221> NAME/KEY: SITE
<222> LOCATION: 5
<223> OTHER INFORMATION: Wherein Xaa is selected from the group
      consisting of 3,4-dihydroxyphenylalanine, tyrosine and
      phosphotyrosine
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: VARIANT
<222> LOCATION: 9
<223> OTHER INFORMATION: Wherein Xaa is tyrosine, phosphotyrosine,
      3-hydroxyproline, 4-hydroxyproline, threonine, phosphothreonine or
      3,4-dihydroxyphenylalanine

<400> SEQUENCE: 9

Ala Lys Pro Xaa Xaa Xaa Xaa Thr Xaa Lys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is serine or phosphoserine
<220> FEATURE:
<221> NAME/KEY: SITE
<222> LOCATION: 5
<223> OTHER INFORMATION: Wherein Xaa is selected from the group
      consisting of 3,4-dihydroxyphenylalanine, tyrosine and
      phosphotyrosine
<220> FEATURE:
<221> NAME/KEY: SITE
<222> LOCATION: 6
<223> OTHER INFORMATION: Wherein Xaa is 3- or 4-hydroxyproline
<220> FEATURE:
<221> NAME/KEY: VARIANT
<222> LOCATION: 8
<223> OTHER INFORMATION: Wherein Xaa is tyrosine, phosphotyrosine,
      3-hydroxyproline, 4-hydroxyproline, threonine, phosphothreonine or
      3,4-dihydroxyphenylalanine
<220> FEATURE:
<221> NAME/KEY: SITE
<222> LOCATION: 9
<223> OTHER INFORMATION: Wherein Xaa is 3- or 4-hydroxyproline

<400> SEQUENCE: 10

Ala Lys Pro Xaa Xaa Xaa Thr Xaa Xaa Lys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine
```

```
<400> SEQUENCE: 11

Ala Lys Pro Xaa Tyr Xaa Xaa Thr Xaa Lys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline

<400> SEQUENCE: 12

Ala Lys Pro Ser Tyr Xaa Xaa Thr Tyr Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7
<223> OTHER INFORMATION: Wherein Xaa is 3- or 4-hydroxyproline

<400> SEQUENCE: 13

Ala Lys Pro Xaa Tyr Xaa Xaa Thr Tyr Lys
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 5
<223> OTHER INFORMATION: Wherein Xaa is 3- or 4-hydroxyproline
<220> FEATURE:
<221> NAME/KEY: SITE
<222> LOCATION: 6
<223> OTHER INFORMATION: Wherein Xaa is 3,4-dihydroxyphenylalanine

<400> SEQUENCE: 14

Lys Pro Ser Tyr Xaa Xaa Lys
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphotyrosine
<220> FEATURE:
<221> NAME/KEY: SITE
<222> LOCATION: 5
<223> OTHER INFORMATION: Wherein Xaa is 3- or 4-hydroxyproline
```

```
<220> FEATURE:
<221> NAME/KEY: SITE
<222> LOCATION: 6
<223> OTHER INFORMATION: Wherein Xaa is 3,4-dihydroxyphenylalanine

<400> SEQUENCE: 15

Lys Pro Ser Xaa Xaa Xaa Lys
1               5

<210> SEQ ID NO 16
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 16

Ala Lys Pro Ser Tyr Xaa Xaa Xaa Xaa Lys
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine

<400> SEQUENCE: 17

Ala Lys Pro Ser Tyr Xaa Xaa Xaa Tyr Lys
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 18

Ala Lys Pro Ser Tyr Xaa Xaa Thr Xaa Xaa Lys
1               5                   10

<210> SEQ ID NO 19
```

```
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 19

Ala Lys Pro Xaa Tyr Xaa Xaa Thr Xaa Xaa Lys
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline

<400> SEQUENCE: 20

Ala Lys Pro Ser Tyr Xaa Xaa Thr Tyr Xaa Lys
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7,10
<223> OTHER INFORMATION: Wherein Xaa is 3- or 4-hydroxyproline

<400> SEQUENCE: 21

Ala Lys Pro Xaa Tyr Xaa Xaa Thr Tyr Xaa Lys
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,9
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 22
```

```
Ala Lys Pro Ser Tyr Xaa Thr Xaa Xaa Lys
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,9
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 23

Ala Lys Pro Xaa Tyr Xaa Thr Xaa Lys
1               5

<210> SEQ ID NO 24
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,9
<223> OTHER INFORMATION: Wherein Xaa is 3- or 4-hydroxyproline

<400> SEQUENCE: 24

Ala Lys Pro Ser Tyr Xaa Thr Tyr Xaa Lys
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,9
<223> OTHER INFORMATION: Wherein Xaa is 3- or 4-hydroxyproline

<400> SEQUENCE: 25

Ala Lys Pro Xaa Tyr Xaa Thr Tyr Xaa Lys
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
```

```
<222> LOCATION: 8
<223> OTHER INFORMATION: Wherein Xaa is phosphothreonine
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 26

Ala Lys Pro Ser Tyr Xaa Xaa Xaa Xaa Xaa Lys
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine

<400> SEQUENCE: 27

Ala Lys Pro Ser Tyr Xaa Xaa Xaa Tyr Xaa Lys
1               5                   10

<210> SEQ ID NO 28
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 28

Ala Lys Pro Ser Tyr Xaa Xaa Thr Xaa
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 29

Ala Lys Pro Xaa Tyr Xaa Xaa Thr Xaa
1               5
```

```
<210> SEQ ID NO 30
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline

<400> SEQUENCE: 30

Ala Lys Pro Ser Tyr Xaa Xaa Thr Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7
<223> OTHER INFORMATION: Wherein Xaa is 3- or 4-hydroxyproline

<400> SEQUENCE: 31

Ala Lys Pro Xaa Tyr Xaa Xaa Thr Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 5
<223> OTHER INFORMATION: Wherein Xaa is 3- or 4-hydroxyproline
<220> FEATURE:
<221> NAME/KEY: SITE
<222> LOCATION: 6
<223> OTHER INFORMATION: Wherein Xaa is 3,4-dihydroxyphenylalanine

<400> SEQUENCE: 32

Lys Pro Ser Tyr Xaa Xaa
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphotyrosine
<220> FEATURE:
<221> NAME/KEY: SITE
<222> LOCATION: 5
<223> OTHER INFORMATION: Wherein Xaa is 3- or 4-hydroxyproline
<220> FEATURE:
<221> NAME/KEY: SITE
<222> LOCATION: 6
<223> OTHER INFORMATION: Wherein Xaa is 3,4-dihydroxyphenylalanine
```

```
<400> SEQUENCE: 33

Lys Pro Ser Xaa Xaa Xaa
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 34

Ala Lys Pro Ser Tyr Xaa Xaa Xaa Xaa
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine

<400> SEQUENCE: 35

Ala Lys Pro Ser Tyr Xaa Xaa Xaa Tyr
1               5

<210> SEQ ID NO 36
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 36

Ala Lys Pro Ser Tyr Xaa Xaa Thr Xaa Xaa
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthetic peptide component
```

```
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 9
<223> OTHER INFORMATION: Wherein Xaa is 3,4-dihydroxyphenylalanine

<400> SEQUENCE: 37

Ala Lys Pro Xaa Tyr Xaa Xaa Thr Xaa Xaa
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline

<400> SEQUENCE: 38

Ala Lys Pro Ser Tyr Xaa Xaa Thr Tyr Xaa
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,7,10
<223> OTHER INFORMATION: Wherein Xaa is 3- or 4-hydroxyproline

<400> SEQUENCE: 39

Ala Lys Pro Xaa Tyr Xaa Xaa Thr Tyr Xaa
1               5                   10

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,9
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 40

Ala Lys Pro Ser Tyr Xaa Thr Xaa Xaa
1               5

<210> SEQ ID NO 41
```

-continued

```
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,9
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is 3,4-dihydroxyphenylalanine

<400> SEQUENCE: 41

Ala Lys Pro Xaa Tyr Xaa Thr Xaa Xaa
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,9
<223> OTHER INFORMATION: Wherein Xaa is 3- or 4-hydroxyproline

<400> SEQUENCE: 42

Ala Lys Pro Ser Tyr Xaa Thr Tyr Xaa
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 4
<223> OTHER INFORMATION: Wherein Xaa is phosphoserine
<220> FEATURE:
<221> NAME/KEY: SITE
<222> LOCATION: 6,9
<223> OTHER INFORMATION: Wherein Xaa is 3- or 4-hydroxyproline

<400> SEQUENCE: 43

Ala Lys Pro Xaa Tyr Xaa Thr Tyr Xaa
1               5

<210> SEQ ID NO 44
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine
<220> FEATURE:
<221> NAME/KEY: SITE
<222> LOCATION: 9
```

```
<223> OTHER INFORMATION: Wherein Xaa is 3,4-dihydroxyphenylalanine

<400> SEQUENCE: 44

Ala Lys Pro Ser Tyr Xaa Xaa Xaa Xaa Xaa
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7,10
<223> OTHER INFORMATION: Wherein Xaa is 3- or 4-hydroxyproline
<220> FEATURE:
<221> NAME/KEY: SITE
<222> LOCATION: 8
<223> OTHER INFORMATION: Wherein Xaa is phosphothreonine

<400> SEQUENCE: 45

Ala Lys Pro Ser Tyr Xaa Xaa Xaa Tyr Xaa
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6,7
<223> OTHER INFORMATION: Wherein Xaa is 3- or 4-hydroxyproline

<400> SEQUENCE: 46

Ala Lys Pro Ser Tyr Xaa Xaa
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide component
<220> FEATURE:
<221> NAME/KEY: SITE
<222> LOCATION: 6
<223> OTHER INFORMATION: Wherein Xaa is 3- or 4-hydroxyproline

<400> SEQUENCE: 47

Ala Lys Pro Ser Tyr Xaa
1               5

<210> SEQ ID NO 48
<211> LENGTH: 4
<212> TYPE: PRT
<213> ORGANISM: Artificial Sequence
<220> FEATURE:
<221> NAME/KEY: SITE
<222> LOCATION: 1,4
<223> OTHER INFORMATION: Wherein Xaa is 3- or 4-hydroxyproline
<220> FEATURE:
<223> OTHER INFORMATION: Synthetic peptide component

<400> SEQUENCE: 48

Xaa Thr Tyr Xaa
1
```